(12) United States Patent
Poeze et al.

(10) Patent No.: US 10,299,708 B1
(45) Date of Patent: *May 28, 2019

(54) MULTI-STREAM DATA COLLECTION SYSTEM FOR NONINVASIVE MEASUREMENT OF BLOOD CONSTITUENTS

(71) Applicant: MASIMO CORPORATION, Irvine, CA (US)

(72) Inventors: Jeroen Poeze, Rancho Santa Margarita, CA (US); Marcelo Lamego, Cupertino, CA (US); Sean Merritt, Lake Forest, CA (US); Cristiano Dalvi, Lake Forest, CA (US); Hung Vo, Fountain Valley, CA (US); Johannes Bruinsma, Opeinde (NL); Ferdyan Lesmana, Irvine, CA (US); Massi Joe E. Kiani, Laguna Niguel, CA (US); Greg Olsen, Trabuco Canyon, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/261,366

(22) Filed: Jan. 29, 2019

Related U.S. Application Data

(63) Continuation of application No. 16/212,537, filed on Dec. 6, 2018, which is a continuation of application
(Continued)

(51) Int. Cl.
*A61B 5/1455* (2006.01)
*A61B 5/00* (2006.01)
*A61B 5/145* (2006.01)

(52) U.S. Cl.
CPC ........ *A61B 5/1455* (2013.01); *A61B 5/14532* (2013.01); *A61B 5/14546* (2013.01);
(Continued)

(58) Field of Classification Search
CPC . A61B 5/0205; A61B 5/1455; A61B 5/14551; A61B 5/14552; A61B 5/14532;
(Continued)

(56) References Cited

U.S. PATENT DOCUMENTS 3,910,701 A 10/1975 Henderson et al.
4,114,604 A 9/1978 Shaw et al.
(Continued)

FOREIGN PATENT DOCUMENTS

EP 419223 3/1991
EP 1 518 494 3/2005
(Continued)

OTHER PUBLICATIONS

US 8,845,543 B2, 09/2014, Diab et al. (withdrawn)
(Continued)

*Primary Examiner* — Eric F Winakur
*Assistant Examiner* — Chu Chuan Liu
(74) *Attorney, Agent, or Firm* — Knobbe Martens Olson & Bear LLP

(57) ABSTRACT

The present disclosure relates to noninvasive methods, devices, and systems for measuring various blood constituents or analytes, such as glucose. In an embodiment, a light source comprises LEDs and super-luminescent LEDs. The light source emits light at least wavelengths of about 1610 nm, about 1640 nm, and about 1665 nm. In an embodiment, the detector comprises a plurality of photodetectors arranged in a special geometry comprising one of a substantially linear substantially equal spaced geometry, a substantially linear substantially non-equal spaced geometry, and a substantially grid geometry.

29 Claims, 65 Drawing Sheets

Related U.S. Application Data

No. 14/981,290, filed on Dec. 28, 2015, which is a continuation of application No. 12/829,352, filed on Jul. 1, 2010, now Pat. No. 9,277,880, which is a continuation of application No. 12/534,827, filed on Aug. 3, 2009, now abandoned, and a continuation-in-part of application No. 12/497,523, filed on Jul. 2, 2009, now Pat. No. 8,437,825, and a continuation-in-part of application No. 12/497,528, filed on Jul. 2, 2009, now Pat. No. 8,577,431, which is a continuation-in-part of application No. 29/323,409, filed on Aug. 25, 2008, now Pat. No. Des. 621,516, said application No. 12/497,523 is a continuation-in-part of application No. 29/323,408, filed on Aug. 25, 2008, now Pat. No. Des. 606,659, and a continuation-in-part of application No. 29/323,409, filed on Aug. 25, 2008, now Pat. No. Des. 621,516, said application No. 12/497,528 is a continuation-in-part of application No. 29/323,408, filed on Aug. 25, 2008, now Pat. No. Des. 606,659.

(60) Provisional application No. 61/091,732, filed on Aug. 25, 2008, provisional application No. 61/086,060, filed on Aug. 4, 2008, provisional application No. 61/086,057, filed on Aug. 4, 2008, provisional application No. 61/086,108, filed on Aug. 4, 2008, provisional application No. 61/086,063, filed on Aug. 4, 2008, provisional application No. 61/078,228, filed on Jul. 3, 2008, provisional application No. 61/078,207, filed on Jul. 3, 2008.

(52) U.S. Cl.
CPC ........ *A61B 5/14552* (2013.01); *A61B 5/6816* (2013.01); *A61B 5/6826* (2013.01); *A61B 5/6829* (2013.01); *A61B 5/6838* (2013.01); *A61B 5/6843* (2013.01); *A61B 2562/0233* (2013.01); *A61B 2562/04* (2013.01); *A61B 2562/046* (2013.01); *A61B 2562/146* (2013.01)

(58) Field of Classification Search
CPC . A61B 5/14546; A61B 5/6829; A61B 5/6843; A61B 5/6826; A61B 5/6816; A61B 5/6838
See application file for complete search history.

(56) References Cited

U.S. PATENT DOCUMENTS

| | | |
|---|---|---|
| 4,258,719 A | 3/1981 | Lewyn |
| 4,267,844 A | 5/1981 | Yamanishi |
| 4,438,338 A | 3/1984 | Stitt |
| 4,444,471 A | 4/1984 | Ford et al. |
| 4,653,498 A | 3/1987 | New, Jr. et al. |
| 4,655,225 A | 4/1987 | Dahne et al. |
| 4,684,245 A | 8/1987 | Goldring |
| 4,709,413 A | 11/1987 | Forrest |
| 4,755,676 A | 7/1988 | Gaalema et al. |
| 4,781,195 A | 11/1988 | Martin |
| 4,805,623 A | 2/1989 | Jöbsis |
| 4,880,304 A | 11/1989 | Jaeb et al. |
| 4,960,128 A | 10/1990 | Gordon et al. |
| 4,964,408 A | 10/1990 | Hink et al. |
| 5,028,787 A | 7/1991 | Rosenthal et al. |
| 5,035,243 A | 7/1991 | Muz |
| 5,041,187 A | 8/1991 | Hink et al. |
| 5,043,820 A | 8/1991 | Wyles et al. |
| 5,069,213 A | 12/1991 | Polczynski |
| 5,069,214 A | 12/1991 | Samaras et al. |
| 5,077,476 A | 12/1991 | Rosenthal |
| 5,086,229 A | 2/1992 | Rosenthal et al. |
| D326,715 S | 6/1992 | Schmidt |
| 5,122,925 A | 6/1992 | Inpyn |
| 5,131,391 A | 7/1992 | Sakai et al. |
| 5,137,023 A | 8/1992 | Mendelson et al. |
| 5,159,929 A | 11/1992 | McMillen et al. |
| 5,163,438 A | 11/1992 | Gordon et al. |
| 5,222,295 A | 6/1993 | Dorris, Jr. |
| 5,222,495 A | 6/1993 | Clarke et al. |
| 5,222,496 A | 6/1993 | Clarke et al. |
| 5,249,576 A | 10/1993 | Goldberger et al. |
| 5,250,342 A | 10/1993 | Lang |
| 5,278,627 A | 1/1994 | Aoyagi et al. |
| 5,297,548 A | 3/1994 | Pologe |
| 5,319,355 A | 6/1994 | Russek |
| 5,337,744 A | 8/1994 | Branigan |
| 5,337,745 A | 8/1994 | Benaron |
| 5,341,805 A | 8/1994 | Stavridi et al. |
| 5,362,966 A | 11/1994 | Rosenthal et al. |
| D353,195 S | 12/1994 | Savage et al. |
| D353,196 S | 12/1994 | Savage et al. |
| 5,377,676 A | 1/1995 | Vari et al. |
| D356,870 S | 3/1995 | Ivers et al. |
| D359,546 S | 6/1995 | Savage et al. |
| 5,427,093 A | 6/1995 | Ogawa et al. |
| 5,431,170 A | 7/1995 | Mathews |
| D361,840 S | 8/1995 | Savage et al. |
| 5,437,275 A | 8/1995 | Amundsen et al. |
| 5,441,054 A | 8/1995 | Tsuchiya |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,034 A | 1/1996 | Lewis et al. |
| 5,482,036 A | 1/1996 | Diab et al. |
| 5,490,505 A | 2/1996 | Diab et al. |
| 5,490,506 A | 2/1996 | Takatani et al. |
| 5,494,043 A | 2/1996 | O'Sullivan et al. |
| 5,511,546 A | 4/1996 | Hon |
| 5,533,511 A | 7/1996 | Kaspari et al. |
| 5,534,851 A | 7/1996 | Russek |
| 5,551,422 A | 9/1996 | Simonsen et al. |
| 5,553,615 A | 9/1996 | Carim et al. |
| 5,553,616 A | 9/1996 | Ham et al. |
| 5,561,275 A | 10/1996 | Savage et al. |
| 5,562,002 A | 10/1996 | Lalin |
| 5,590,649 A | 1/1997 | Caro et al. |
| 5,601,079 A * | 2/1997 | Wong ............... A61B 5/14532 356/39 |
| 5,602,924 A | 2/1997 | Durand et al. |
| D378,414 S | 3/1997 | Allen et al. |
| 5,625,458 A | 4/1997 | Alfano et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,676,143 A | 10/1997 | Simonsen et al. |
| 5,685,299 A | 11/1997 | Diab et al. |
| D390,666 S | 2/1998 | Lagerlof |
| D393,830 S | 4/1998 | Tobler et al. |
| 5,743,262 A | 4/1998 | Lepper, Jr. et al. |
| 5,750,927 A | 5/1998 | Baltazar |
| 5,752,914 A | 5/1998 | Delonzor et al. |
| 5,758,644 A | 6/1998 | Diab et al. |
| 5,760,910 A | 6/1998 | Lepper, Jr. et al. |
| 5,766,131 A | 6/1998 | Kondo et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,792,052 A | 8/1998 | Isaacson et al. |
| 5,810,734 A | 9/1998 | Caro et al. |
| 5,823,950 A | 10/1998 | Diab et al. |
| 5,826,885 A | 10/1998 | Helgeland |
| 5,830,131 A | 11/1998 | Caro et al. |
| 5,833,618 A | 11/1998 | Caro et al. |
| D403,070 S | 12/1998 | Maeda et al. |
| 5,851,178 A | 12/1998 | Aronow |

(56) References Cited

U.S. PATENT DOCUMENTS

| | | |
|---|---|---|
| 5,860,919 A | 1/1999 | Kiani-Azarbayjany et al. |
| 5,890,929 A | 4/1999 | Mills et al. |
| 5,902,235 A | 5/1999 | Lewis et al. |
| 5,903,357 A | 5/1999 | Colak |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,957,840 A | 9/1999 | Terasawa et al. |
| D414,870 S | 10/1999 | Saltzstein et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,049,727 A | 4/2000 | Crothall |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,866 A | 11/2000 | Miesel et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,172,743 B1 | 1/2001 | Kley et al. |
| 6,181,958 B1 | 1/2001 | Steuer et al. |
| 6,184,521 B1 | 2/2001 | Coffin, IV et al. |
| 6,206,830 B1 | 3/2001 | Diab et al. |
| 6,223,063 B1 | 4/2001 | Chaiken et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,278,889 B1 | 8/2001 | Robinson |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| D452,012 S | 12/2001 | Phillips |
| 6,325,761 B1 | 12/2001 | Jay |
| 6,334,065 B1 | 12/2001 | Al-Ali et al. |
| 6,343,223 B1 | 1/2002 | Chin et al. |
| 6,343,224 B1 | 1/2002 | Parker |
| 6,345,194 B1 | 2/2002 | Nelson et al. |
| 6,349,228 B1 | 2/2002 | Kiani et al. |
| 6,353,750 B1 | 3/2002 | Kimura et al. |
| 6,360,113 B1 | 3/2002 | Dettling |
| 6,360,114 B1 | 3/2002 | Diab et al. |
| 6,360,115 B1 | 3/2002 | Greenwald et al. |
| D455,834 S | 4/2002 | Donars et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| D463,561 S | 9/2002 | Fukatsu et al. |
| 6,463,311 B1 | 10/2002 | Diab |
| 6,470,199 B1 | 10/2002 | Kopotic et al. |
| RE37,922 E | 12/2002 | Sharan |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,522,521 B2 | 2/2003 | Mizuno et al. |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,509 B2 | 8/2003 | Schmitt |
| 6,606,511 B1 | 8/2003 | Ali et al. |
| D481,459 S | 10/2003 | Nahm |
| 6,632,181 B2 | 10/2003 | Flaherty et al. |
| 6,636,759 B2 | 10/2003 | Robinson |
| 6,639,668 B1 | 10/2003 | Trepagnier |
| 6,639,867 B2 | 10/2003 | Shim |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,668,185 B2 | 12/2003 | Toida |
| 6,671,531 B2 | 12/2003 | Al-Ali et al. |
| 6,678,543 B2 | 1/2004 | Diab et al. |
| 6,681,133 B2 | 1/2004 | Chaiken et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,748,254 B2 | 6/2004 | O'Neil et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,010 B2 | 11/2004 | Seetharaman et al. |
| 6,816,241 B2 | 11/2004 | Grubisic et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| D502,655 S | 3/2005 | Huang |
| 6,861,639 B2 | 3/2005 | Al-Ali |
| 6,898,452 B2 | 5/2005 | Al-Ali et al. |
| 6,912,413 B2 | 6/2005 | Rantala et al. |
| 6,920,345 B2 | 7/2005 | Al-Ali et al. |
| D508,862 S | 8/2005 | Behar et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| D510,625 S | 10/2005 | Widener et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| D514,461 S | 2/2006 | Harju |
| 6,995,400 B2 | 2/2006 | Mizuyoshi |
| 6,996,427 B2 | 2/2006 | Ali et al. |

(56) References Cited

U.S. PATENT DOCUMENTS

| | | |
|---|---|---|
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,047,054 B2 | 5/2006 | Benni |
| 7,067,893 B2 | 6/2006 | Mills et al. |
| 7,092,757 B2 | 8/2006 | Larson et al. |
| 7,096,052 B2 | 8/2006 | Mason et al. |
| 7,096,054 B2 | 8/2006 | Abdul-Hafiz et al. |
| 7,113,815 B2 * | 9/2006 | O'Neil ............... A61B 5/14552 600/310 |
| 7,132,641 B2 | 11/2006 | Schulz et al. |
| 7,142,901 B2 | 11/2006 | Kiani et al. |
| 7,149,561 B2 | 12/2006 | Diab |
| D535,031 S | 1/2007 | Barrett et al. |
| D537,164 S | 2/2007 | Shigemori et al. |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,230,227 B2 | 6/2007 | Wilcken et al. |
| D547,454 S | 7/2007 | Hsieh |
| 7,239,905 B2 | 7/2007 | Kiani-Azarbayjany et al. |
| 7,245,953 B1 | 7/2007 | Parker |
| D549,830 S | 8/2007 | Behar et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| D550,364 S | 9/2007 | Glover et al. |
| D551,350 S | 9/2007 | Lorimer et al. |
| 7,272,425 B2 | 9/2007 | Al-Ali |
| 7,274,955 B2 | 9/2007 | Kiani et al. |
| D553,248 S | 10/2007 | Nguyen |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| D562,985 S | 2/2008 | Brefka et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| D567,125 S | 4/2008 | Okabe et al. |
| 7,355,512 B1 | 4/2008 | Al-Ali |
| 7,356,365 B2 | 4/2008 | Schurman |
| 7,365,923 B2 | 4/2008 | Hargis et al. |
| D569,001 S | 5/2008 | Omaki |
| D569,521 S | 5/2008 | Omaki |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,189 B2 | 7/2008 | Qing et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,153 B2 | 3/2009 | Blank et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,519,327 B2 | 4/2009 | White |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,601,123 B2 | 10/2009 | Tweed et al. |
| 7,606,606 B2 | 10/2009 | Laakkonen |
| D603,966 S | 11/2009 | Jones et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| 7,657,294 B2 | 2/2010 | Eghbal et al. |
| 7,657,295 B2 | 2/2010 | Coakley et al. |
| 7,657,296 B2 | 2/2010 | Raridan et al. |
| D614,305 S | 4/2010 | Al-Ali et al. |
| RE41,317 E | 5/2010 | Parker |
| 7,726,209 B2 | 6/2010 | Ruotoistenmäki |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,809,418 B2 | 10/2010 | Xu |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,862,523 B2 | 1/2011 | Ruotoistenmaki |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,506 B2 | 3/2011 | Xu et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |

(56) References Cited

U.S. PATENT DOCUMENTS

| | | |
|---|---|---|
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,044,998 B2 | 10/2011 | Heenan |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,126,531 B2 | 2/2012 | Crowley |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,219,170 B2 | 7/2012 | Hausmann et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,289,130 B2 | 10/2012 | Nakajima et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,332,006 B2 | 12/2012 | Naganuma et al. |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,364,389 B2 | 1/2013 | Dorogusker et al. |
| 8,374,665 B2 | 2/2013 | Lamego |
| 8,380,272 B2 | 2/2013 | Barrett et al. |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,421,022 B2 | 4/2013 | Rozenfeld |
| 8,423,106 B2 | 4/2013 | Lamego et al. |
| 8,428,674 B2 | 4/2013 | Duffy et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,602,971 B2 | 12/2013 | Farr |
| 8,606,342 B2 | 12/2013 | Diab |
| 8,615,290 B2 | 12/2013 | Lin et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,655,004 B2 | 2/2014 | Prest et al. |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,111 B2 | 4/2014 | LeBoeuf et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,760,517 B2 | 6/2014 | Sarwar et al. |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |

(56) References Cited

U.S. PATENT DOCUMENTS

| | | |
|---|---|---|
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,437 B2 | 7/2015 | Paalasmaa |
| 9,072,474 B2 | 7/2015 | Al-Ali et al. |
| 9,078,560 B2 | 7/2015 | Schurman et al. |
| 9,081,889 B2 | 7/2015 | Ingrassia, Jr. et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,210,566 B2 | 12/2015 | Ziemianska et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,311,382 B2 | 4/2016 | Varoglu et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,357,665 B2 | 5/2016 | Myers et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,489,081 B2 | 11/2016 | Anzures et al. |
| 9,497,534 B2 | 11/2016 | Prest et al. |
| 9,526,430 B2 | 12/2016 | Srinivas et al. |
| 9,553,625 B2 | 1/2017 | Hatanaka et al. |
| 9,591,975 B2 | 3/2017 | Dalvi et al. |
| 9,593,969 B2 | 3/2017 | King |
| 9,651,405 B1 | 5/2017 | Gowreesunker et al. |
| 9,668,676 B2 | 6/2017 | Culbert |
| 9,668,680 B2 | 6/2017 | Bruinsma et al. |
| 9,699,546 B2 | 7/2017 | Qian et al. |
| 9,716,937 B2 | 7/2017 | Qian et al. |
| 9,717,425 B2 | 8/2017 | Kiani et al. |
| 9,723,997 B1 | 8/2017 | Lamego |
| 9,781,984 B2 | 10/2017 | Baranski et al. |
| 9,838,775 B2 | 12/2017 | Qian et al. |
| 9,848,823 B2 | 12/2017 | Raghuram et al. |
| 9,866,671 B1 | 1/2018 | Thompson et al. |
| 9,867,575 B2 | 1/2018 | Maani et al. |
| 9,898,049 B2 | 2/2018 | Myers et al. |
| 9,918,646 B2 | 3/2018 | Singh Alvarado et al. |
| 9,952,095 B1 | 4/2018 | Hotelling et al. |
| 10,039,080 B2 | 7/2018 | Miller et al. |
| 10,055,121 B2 | 8/2018 | Chaudhri et al. |
| 10,066,970 B2 | 9/2018 | Gowreesunker et al. |
| 10,076,257 B2 | 9/2018 | Lin et al. |
| 10,078,052 B2 | 9/2018 | Ness et al. |
| 2002/0099279 A1 | 7/2002 | Pfeiffer et al. |
| 2006/0005944 A1 | 1/2006 | Wang et al. |
| 2006/0025659 A1 | 2/2006 | Kiguchi et al. |
| 2006/0076473 A1 | 4/2006 | Wilcken et al. |
| 2007/0149864 A1 | 6/2007 | Laakkonen |
| 2007/0238955 A1 | 10/2007 | Tearney et al. |
| 2007/0293792 A1 | 12/2007 | Sliwa et al. |
| 2008/0130232 A1 | 6/2008 | Yamamoto |
| 2008/0139908 A1 | 6/2008 | Kurth |
| 2009/0030327 A1 | 1/2009 | Chance |
| 2009/0043180 A1 | 2/2009 | Tschautscher et al. |
| 2009/0129102 A1 | 5/2009 | Xiao et al. |
| 2009/0247984 A1 | 10/2009 | Lamego et al. |
| 2009/0259114 A1 | 10/2009 | Johnson et al. |
| 2009/0275844 A1 | 11/2009 | Al-Ali |
| 2009/0306487 A1 | 12/2009 | Crowe et al. |
| 2010/0004518 A1 | 1/2010 | Vo et al. |
| 2010/0030040 A1 | 2/2010 | Poeze et al. |
| 2010/0217102 A1 | 8/2010 | LeBoeuf et al. |
| 2011/0001605 A1 | 1/2011 | Kiani et al. |
| 2011/0004082 A1 | 1/2011 | Poeze et al. |
| 2011/0082711 A1 | 4/2011 | Poeze et al. |
| 2011/0105854 A1 | 5/2011 | Kiani et al. |
| 2011/0105865 A1 | 5/2011 | Yu et al. |
| 2011/0208015 A1 | 8/2011 | Welch et al. |
| 2011/0213212 A1 | 9/2011 | Al-Ali |

(56) References Cited

U.S. PATENT DOCUMENTS

| | | |
|---|---|---|
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171146 A1 | 6/2014 | Ma et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |
| 2015/0173671 A1 | 6/2015 | Paalasmaa et al. |
| 2015/0255001 A1 | 9/2015 | Haughay et al. |
| 2015/0281424 A1 | 10/2015 | Vock et al. |
| 2015/0318100 A1 | 11/2015 | Rothkopf et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0019360 A1 | 1/2016 | Pahwa et al. |
| 2016/0023245 A1 | 1/2016 | Zadesky et al. |
| 2016/0029932 A1 | 2/2016 | Al-Ali |
| 2016/0029933 A1 | 2/2016 | Al-Ali et al. |
| 2016/0038045 A1 | 2/2016 | Shapiro |
| 2016/0045118 A1 | 2/2016 | Kiani |
| 2016/0051157 A1 | 2/2016 | Waydo |
| 2016/0051158 A1 | 2/2016 | Silva |
| 2016/0051205 A1 | 2/2016 | Al-Ali et al. |
| 2016/0058302 A1 | 3/2016 | Raghuram et al. |
| 2016/0058309 A1 | 3/2016 | Han |
| 2016/0058312 A1 | 3/2016 | Han et al. |
| 2016/0058338 A1 | 3/2016 | Schurman et al. |
| 2016/0058347 A1 | 3/2016 | Reichgott et al. |
| 2016/0058356 A1 | 3/2016 | Raghuram et al. |
| 2016/0058370 A1 | 3/2016 | Raghuram et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0071392 A1 | 3/2016 | Hankey et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0154950 A1 | 6/2016 | Nakajima et al. |
| 2016/0157780 A1 | 6/2016 | Rimminen et al. |
| 2016/0166183 A1 | 6/2016 | Poeze et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0213309 A1 | 7/2016 | Sannholm et al. |
| 2016/0256058 A1 | 9/2016 | Pham et al. |
| 2016/0256082 A1 | 9/2016 | Ely et al. |
| 2016/0267238 A1 | 9/2016 | Nag |
| 2016/0287181 A1 | 10/2016 | Han et al. |
| 2016/0296173 A1 | 10/2016 | Culbert |
| 2016/0296174 A1 | 10/2016 | Isikman et al. |
| 2016/0310027 A1 | 10/2016 | Han |
| 2016/0378069 A1 | 12/2016 | Rothkopf |
| 2016/0378071 A1 | 12/2016 | Rothkopf |
| 2017/0007183 A1 | 1/2017 | Dusan et al. |
| 2017/0010858 A1 | 1/2017 | Prest et al. |
| 2017/0074897 A1 | 3/2017 | Mermel et al. |
| 2017/0084133 A1 | 3/2017 | Cardinali et al. |
| 2017/0086689 A1 | 3/2017 | Shui et al. |
| 2017/0086742 A1 | 3/2017 | Harrison-Noonan et al. |
| 2017/0086743 A1 | 3/2017 | Bushnell et al. |
| 2017/0094450 A1 | 3/2017 | Tu et al. |
| 2017/0164884 A1 | 6/2017 | Culbert et al. |
| 2017/0248446 A1 | 8/2017 | Gowreesunker et al. |
| 2017/0273619 A1 | 9/2017 | Alvarado et al. |
| 2017/0281024 A1 | 10/2017 | Narasimhan et al. |
| 2017/0293727 A1 | 10/2017 | Klaassen et al. |
| 2017/0325698 A1 | 11/2017 | Allec et al. |
| 2017/0325744 A1 | 11/2017 | Allec et al. |
| 2017/0340209 A1 | 11/2017 | Klaassen et al. |
| 2017/0340219 A1 | 11/2017 | Sullivan et al. |

(56) References Cited

U.S. PATENT DOCUMENTS

| | | |
|---|---|---|
| 2017/0347885 A1 | 12/2017 | Tan et al. |
| 2017/0354332 A1 | 12/2017 | Lamego |
| 2017/0354795 A1 | 12/2017 | Blahnik et al. |
| 2017/0358239 A1 | 12/2017 | Arney et al. |
| 2017/0358240 A1 | 12/2017 | Blahnik et al. |
| 2017/0358242 A1 | 12/2017 | Thompson et al. |
| 2017/0360306 A1 | 12/2017 | Narasimhan et al. |
| 2017/0366657 A1 | 12/2017 | Thompson et al. |
| 2018/0014781 A1 | 1/2018 | Clavelle et al. |
| 2018/0025287 A1 | 1/2018 | Mathew et al. |
| 2018/0056129 A1 | 1/2018 | Narasimha Rao et al. |
| 2018/0042556 A1 | 2/2018 | Shahparnia et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055390 A1 | 3/2018 | Kiani |
| 2018/0055439 A1 | 3/2018 | Pham et al. |
| 2018/0078151 A1 | 3/2018 | Allec et al. |
| 2018/0078182 A1 | 3/2018 | Chen et al. |
| 2018/0110469 A1 | 4/2018 | Maani et al. |
| 2018/0153418 A1 | 6/2018 | Sullivan et al. |
| 2018/0164853 A1 | 6/2018 | Myers et al. |
| 2018/0196514 A1 | 7/2018 | Allec et al. |
| 2018/0228414 A1 | 8/2018 | Shao et al. |
| 2018/0238734 A1 | 8/2018 | Hotelling et al. |
| 2018/0279956 A1 | 10/2018 | Waydo et al. |

FOREIGN PATENT DOCUMENTS

| | | |
|---|---|---|
| JP | 05-325705 A | 12/1993 |
| JP | 08-185864 | 7/1996 |
| JP | 2001-66990 | 3/2001 |
| JP | 2001-087250 A | 4/2001 |
| JP | 2002-500908 A | 1/2002 |
| JP | 2003-024276 A | 1/2003 |
| JP | 2003-508104 A | 3/2003 |
| JP | 2003-265444 A | 9/2003 |
| JP | 2006-177837 A | 7/2006 |
| JP | 2006-198321 A | 8/2006 |
| JP | 2007-389463 A | 11/2007 |
| JP | 2008-099222 A | 4/2008 |
| JP | 5756752 | 6/2015 |
| WO | WO 1993/12712 | 7/1993 |
| WO | WO 1999/000053 | 1/1999 |
| WO | WO 1999/01704 | 7/1999 |
| WO | WO 2000/25112 | 5/2000 |
| WO | WO 2001/09589 | 2/2001 |
| WO | WO 2010/003134 | 1/2010 |
| WO | WO 2014/149781 | 9/2014 |
| WO | WO 2014/158820 | 10/2014 |

OTHER PUBLICATIONS

U.S. Appl. No. 12/534,827, filed Aug. 3, 2009, Multi-Stream Data Collection System for Noninvasive Measurement of Blood Constituents.
U.S. Appl. No. 14/981,290, filed Dec. 28, 2015, Multi-Stream Data Collection System for Noninvasive Measurement of Blood Constituents.
U.S. Appl. No. 16/212,440, filed Dec. 6, 2018, Multi-Stream Data Collection System for Noninvasive Measurement of Blood Constituents.
U.S. Appl. No. 16/212,537, filed Dec. 6, 2018, Multi-Stream Data Collection System for Noninvasive Measurement of Blood Constituents.
U.S. Appl. No. 16/261,326, filed Jan. 29, 2019, Multi-Stream Data Collection System for Noninvasive Measurement of Blood Constituents.
U.S. Appl. No. 14/064,055, filed Oct. 25, 2013, Multi-Stream Sensor for Noninvasive Measurement of Blood Constituents.
U.S. Appl. No. 15/660,743, filed Jul. 26, 2017, Noise Shielding for a Noninvasive Device.
U.S. Appl. No. 12/497,506, filed Jul. 2, 2009, Heat Sink for Noninvasive Medical Sensor.
PCT International Search Report, App. No. PCT/US2010/047899, Date of Actual Completion of Search: Jan. 26, 2011, 4 pages.
International Search Report and Written Opinion for PCT/US2009/049638, dated Jan. 7, 2010.
International Search Report issued in Application No. PCT/US2009/052756, dated Feb. 10, 2009 in 14 pages.
International Preliminary Report on Patentability and Written Opinion of the International Searching Authority issued in Application No. PCT US2009/049638, dated Jan. 5, 2011 in 9 pages.
International Preliminary Report on Patentability and Written Opinion of the International Searching Authority issued in Application No. PCT/US2009/052756, dated Feb. 8, 2011 in 8 pages.
Burritt, Mary F.; Current Analytical Approaches to Measuring Blood Analytes; vol. 36; No. 8(B); 1990.
Hall, et al., Jeffrey W.; Near-Infrared Spectrophotometry: A New Dimension in Clinical Chemistry; vol. 38; No. 9; 1992.
Kuenstner, et al., J. Todd; Measurement of Hemoglobin in Unlysed Blood by Near-Infrared Spectroscopy; vol. 48; No. 4, 1994.
Manzke, et al., B., Multi Wavelength Pulse Oximetry in the Measurement of Hemoglobin Fractions; SPIE, vol. 2676, Apr. 24, 1996.
Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.
Schmitt, Joseph M.; Simple Photon Diffusion Anaylsis of the Effects of Multiple Scattering on Pulse Oximetry; Mar. 14, 1991; revised Aug. 30, 1991.
Schmitt, et al., Joseph M.; Measurement of Blood Hematocrit by Dual-Wavelength near-IR Photoplethysmography; vol. 1641; 1992.
Schnapp, et al., L.M.; Pulse Oximetry. Uses and Abuses.; Chest 1990; 98; 1244-1250 DOI 10.1378/Chest.98.5.1244.
http://www.masimo.com/rainbow/pronto.htm Noninvasive & Immediate Hemoglobin Testing, printed on Aug. 20, 2009.
http://www.masimo.com/pulseOximeter/Rad5.htm; Signal Extraction Pulse Oximeter, printed on Aug. 20, 2009.
http://blogderoliveira.blogspot.com/2008_02_01_archive.html; Ricardo Oliveira, printed on Aug. 20, 2009.
http://www.masimo.com/rad-57/; Noninvasive Measurement of Methemoglobin, Carboxyhemoglobin and Oxyhemoglobin in the blood. Printed on Aug. 20, 2009.
http://amivital.ugr.es/blog/?tag+spo2; Monitorizacion de la hemoglobina . . . y mucho mas, printed on Aug. 20, 2009.
http://www.masimo.com/spco/; Carboxyhemoglobin Noninvasive > Continuous > Immediate, printed on Aug. 20, 2009.
http://www.masimo.com/PARTNERS/WELCHALLYN.htm; Welch Allyn Expands Patient Monitor Capabilities with Masimo Pulse Oximetry Technology, printed on Aug. 20, 2009.
http://www.masimo.com/pulseOximeter/PPO.htm; Masimo Personal Pulse Oximeter, printed on Aug. 20, 2009.
http://www.masimo.com/generalFloor/system.htm; Masimo Patient SafetyNet System at a Glance, printed on Aug. 20, 2009.
http://www.masimo.com/partners/GRASEBY.htm; Graseby Medical Limited, printed on Aug. 20, 2009.
Japanese Office Action, re JP Application No. 2011-516895, dated Sep. 2, 2014, with translation.
Japanese Notice of Allowance, re JP Application No. 2011-516895, dated May 12, 2015, no translation.
European Office Action issued in application No. 10763901.5 dated Jan. 11, 2013.
European Office Action issued in application No. 10763901.5 dated Aug. 27, 2014.
European Office Action issued in application No. 10763901.5 dated Aug. 6, 2015.
European Office Action issued in Application No. 09791157.2, dated Jun. 20, 2016.
Kanukurthy et al., "Data Acquisition Unit for an Implantable Multi-Channel Optical Glucose Sensor", Electro/Information Technology Conference, Chicago, IL, USA, May 17-20, 2007, pp. 1-6.
Smith, "The Pursuit of Noninvasive Glucose: 'Hunting the Deceitful Turkey'", 2006.

(56) References Cited

OTHER PUBLICATIONS

Small et al., "Data Handling Issues for Near-Infrared Glucose Measurements", http://www.ieee.org/organizations/pubs/newsletters/leos/apr98/datahandling.htm, accessed Nov. 27, 2007.

* cited by examiner

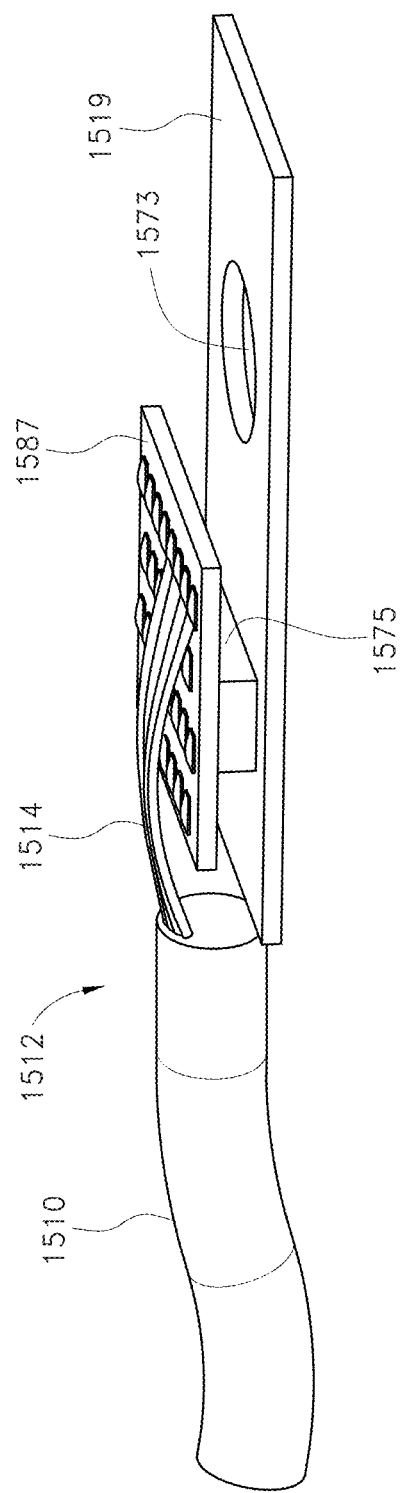

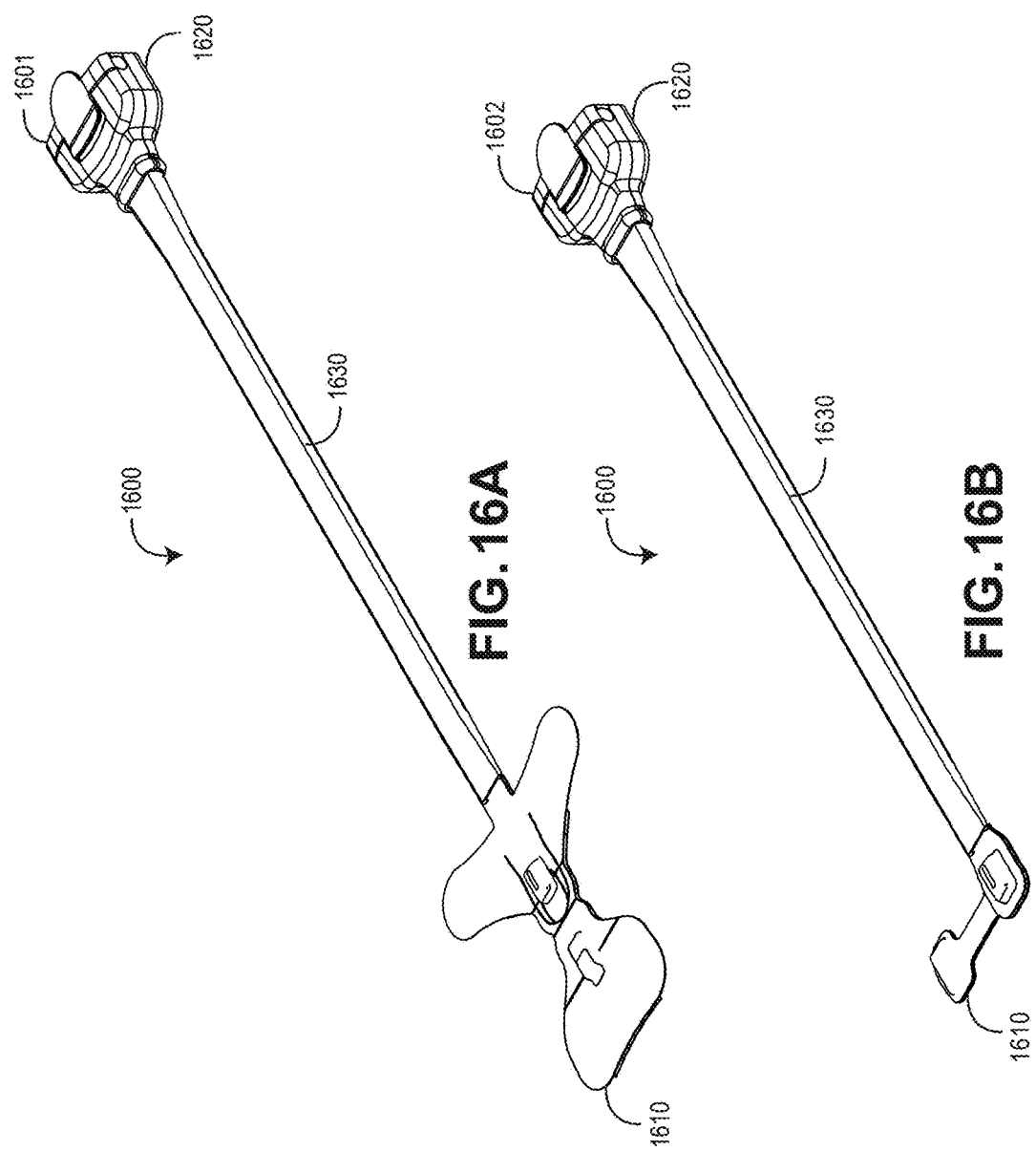

MULTI-STREAM DATA COLLECTION SYSTEM FOR NONINVASIVE MEASUREMENT OF BLOOD CONSTITUENTS

RELATED APPLICATIONS

This application is a continuation of U.S. patent application Ser. No. 16/212,537, filed Dec. 6, 2018, which is a continuation of U.S. patent application Ser. No. 14/981,290 filed Dec. 28, 2015, which is a continuation of U.S. patent application Ser. No. 12/829,352 filed Jul. 1, 2010, which is a continuation of U.S. patent application Ser. No. 12/534,827 filed Aug. 3, 2009, which claims the benefit of priority under 35 U.S.C. § 119(e) of the following U.S. Provisional Patent Application Nos. 61/086,060 filed Aug. 4, 2008, 61/086,108 filed Aug. 4, 2008, 61/086,063 filed Aug. 4, 2008, 61/086,057 filed Aug. 4, 2008, and 61/091,732 filed Aug. 25, 2008. U.S. patent application Ser. No. 12/829,352 is also a continuation-in-part of U.S. patent application Ser. No. 12/497,528 filed Jul. 2, 2009, which claims the benefit of priority under 35 U.S.C. § 119(e) of the following U.S. Provisional Patent Application Nos. 61/086,060 filed Aug. 4, 2008, 61/086,108 filed Aug. 4, 2008, 61/086,063 filed Aug. 4, 2008, 61/086,057 filed Aug. 4, 2008, 61/078,228 filed Jul. 3, 2008, 61/078,207 filed Jul. 3, 2008, and 61/091,732 filed Aug. 25, 2008. U.S. patent application Ser. No. 12/497,528 also claims the benefit of priority under 35 U.S.C. § 120 as a continuation-in-part of the following U.S. Design Patent application Nos. 29/323,409 filed Aug. 25, 2008 and Ser. No. 29/323,408 filed Aug. 25, 2008. U.S. patent application Ser. No. 12/829,352 is also a continuation-in-part of U.S. patent application Ser. No. 12/497,523 filed Jul. 2, 2009, which claims the benefit of priority under 35 U.S.C. § 119(e) of the following U.S. Provisional Patent Application Nos. 61/086,060 filed Aug. 4, 2008, 61/086,108 filed Aug. 4, 2008, 61/086,063 filed Aug. 4, 2008, 61/086,057 filed Aug. 4, 2008, 61/078,228 filed Jul. 3, 2008, 61/078,207 filed Jul. 3, 2008, and 61/091,732 filed Aug. 25, 2008. U.S. patent application Ser. No. 12/497,523 also claims the benefit of priority under 35 U.S.C. § 120 as a continuation-in-part of the following U.S. Design patent application Ser. No. 29/323,409 filed Aug. 25, 2008 and Ser. No. 29/323,408 filed Aug. 25, 2008.

This application is related to the following U.S. Patent Applications:

| application Ser. No. | Filing Date | Title |
| --- | --- | --- |
| 12/497,528 | Jul. 2, 2009 | Noise Shielding for Noninvasive Device |
| 12/497,523 | Jul. 2, 2009 | Contoured Protrusion for Improving Spectroscopic Measurement of Blood Constituents |
| 12/497,506 | Jul. 2, 2009 | Heat Sink for Noninvasive Medical Sensor |
| 12/534,812 | Aug. 3, 2009 | Multi-Stream Sensor Front Ends for Non-Invasive Measurement of Blood Constituents |
| 12/534,823 | Aug. 3, 2009 | Multi-Stream Sensor for Non-Invasive Measurement of Blood Constituents |
| 12/534,825 | Aug. 3, 2009 | Multi-Stream Emitter for Non-Invasive Measurement of Blood Constituents |

The foregoing applications are hereby incorporated by reference in their entirety.

BACKGROUND

The standard of care in caregiver environments includes patient monitoring through spectroscopic analysis using, for example, a pulse oximeter. Devices capable of spectroscopic analysis generally include a light source(s) transmitting optical radiation into or reflecting off a measurement site, such as, body tissue carrying pulsing blood. After attenuation by tissue and fluids of the measurement site, a photo-detection device(s) detects the attenuated light and outputs a detector signal(s) responsive to the detected attenuated light. A signal processing device(s) process the detector(s) signal(s) and outputs a measurement indicative of a blood constituent of interest, such as glucose, oxygen, met hemoglobin, total hemoglobin, other physiological parameters, or other data or combinations of data useful in determining a state or trend of wellness of a patient.

In noninvasive devices and methods, a sensor is often adapted to position a finger proximate the light source and light detector. For example, noninvasive sensors often include a clothespin-shaped housing that includes a contoured bed conforming generally to the shape of a finger.

SUMMARY

This disclosure describes embodiments of noninvasive methods, devices, and systems for measuring a blood constituent or analyte, such as oxygen, carbon monoxide, methemoglobin, total hemoglobin, glucose, proteins, glucose, lipids, a percentage thereof (e.g., saturation) or for measuring many other physiologically relevant patient characteristics. These characteristics can relate, for example, to pulse rate, hydration, trending information and analysis, and the like.

In an embodiment, the system includes a noninvasive sensor and a patient monitor communicating with the non-invasive sensor. The non-invasive sensor may include different architectures to implement some or all of the disclosed features. In addition, an artisan will recognize that the non-invasive sensor may include or may be coupled to other components, such as a network interface, and the like. Moreover, the patient monitor may include a display device, a network interface communicating with any one or combination of a computer network, a handheld computing device, a mobile phone, the Internet, or the like. In addition, embodiments may include multiple optical sources that emit light at a plurality of wavelengths and that are arranged from the perspective of the light detector(s) as a point source.

In an embodiment, a noninvasive device is capable of producing a signal responsive to light attenuated by tissue at a measurement site. The device may comprise an optical source and a plurality of photodetectors. The optical source is configured to emit optical radiation at least at wavelengths between about 1600 nm and about 1700 nm. The photodetectors are configured to detect the optical radiation from said optical source after attenuation by the tissue of the measurement site and each output a respective signal stream responsive to the detected optical radiation.

In an embodiment, a noninvasive, physiological sensor is capable of outputting a signal responsive to a blood analyte present in a monitored patient. The sensor may comprise a sensor housing, an optical source, and photodetectors. The optical source is positioned by the housing with respect to a tissue site of a patient when said housing is applied to the patient. The photodetectors are positioned by the housing with respect to said tissue site when the housing is applied to the patient with a variation in path length among at least some of the photodetectors from the optical source. The photodetectors are configured to detect a sequence of optical radiation from the optical source after attenuation by tissue of the tissue site. The photodetectors may be each configured to output a respective signal stream responsive to the detected sequence of optical radiation. An output signal responsive to one or more of the signal streams is then usable to determine the blood analyte based at least in part on the variation in path length In an embodiment, a method of measuring an analyte based on multiple streams of optical radiation measured from a measurement site is provided. A sequence of optical radiation pulses is emitted to the measurement site. At a first location, a first stream of optical radiation is detected from the measurement site. At least at one additional location different from the first location, an additional stream of optical radiation is detected from the measurement site. An output measurement value indicative of the analyte is then determined based on the detected streams of optical radiation.

In various embodiments, the present disclosure relates to an interface for a noninvasive sensor that comprises a front-end adapted to receive an input signals from optical detectors and provide corresponding output signals. In an embodiment, the front-end is comprised of switched-capacitor circuits that are capable of handling multiple streams of signals from the optical detectors. In another embodiment, the front-end comprises transimpedance amplifiers that are capable of handling multiple streams of input signals. In addition, the transimpedance amplifiers may be configured based on the characteristics of the transimpedance amplifier itself, the characteristics of the photodiodes, and the number of photodiodes coupled to the transimpedance amplifier.

In disclosed embodiments, the front-ends are employed in noninvasive sensors to assist in measuring and detecting various analytes. The disclosed noninvasive sensor may also include, among other things, emitters and detectors positioned to produce multi-stream sensor information. An artisan will recognize that the noninvasive sensor may have different architectures and may include or be coupled to other components, such as a display device, a network interface, and the like. An artisan will also recognize that the front-ends may be employed in any type of noninvasive sensor.

In an embodiment, a front-end interface for a noninvasive, physiological sensor comprises: a set of inputs configured to receive signals from a plurality of detectors in the sensor; a set of transimpedance amplifiers configured to convert the signals from the plurality of detectors into an output signal having a stream for each of the plurality of detectors; and an output configured to provide the output signal.

In an embodiment, a front-end interface for a noninvasive, physiological sensor comprises: a set of inputs configured to receive signals from a plurality of detectors in the sensor; a set of switched capacitor circuits configured to convert the signals from the plurality of detectors into a digital output signal having a stream for each of the plurality of detectors; and an output configured to provide the digital output signal.

In an embodiment, a conversion processor for a physiological, noninvasive sensor comprises: a multi-stream input configured to receive signals from a plurality of detectors in the sensor, wherein the signals are responsive to optical radiation from a tissue site; a modulator that converts the multi-stream input into a digital bit-stream; and a signal processor that produces an output signal from the digital bit-stream.

In an embodiment, a front-end interface for a noninvasive, physiological sensor comprises: a set of inputs configured to receive signals from a plurality of detectors in the sensor; a set of respective transimpedance amplifiers for each detector configured to convert the signals from the plurality of detectors into an output signal having a stream for each of the plurality of detectors; and an output configured to provide the output signal.

In certain embodiments, a noninvasive sensor interfaces with tissue at a measurement site and deforms the tissue in a way that increases signal gain in certain desired wavelengths.

In some embodiments, a detector for the sensor may comprise a set of photodiodes that are arranged in a spatial configuration. This spatial configuration may allow, for example, signal analysis for measuring analytes like glucose. In various embodiments, the detectors can be arranged across multiple locations in a spatial configuration. The spatial configuration provides a geometry having a diversity of path lengths among the detectors. For example, the detector in the sensor may comprise multiple detectors that are arranged to have a sufficient difference in mean path length to allow for noise cancellation and noise reduction.

In an embodiment, a physiological, noninvasive detector is configured to detect optical radiation from a tissue site. The detector comprises a set of photodetectors and a conversion processor. The set of photodetectors each provide a signal stream indicating optical radiation from the tissue site. The set of photodetectors are arranged in a spatial configuration that provides a variation in path lengths between at least some of the photodetectors. The conversion processor that provides information indicating an analyte in the tissue site based on ratios of pairs of the signal streams.

The present disclosure, according to various embodiments, relates to noninvasive methods, devices, and systems for measuring a blood analyte, such as glucose. In the present disclosure, blood analytes are measured noninvasively based on multi-stream infrared and near-infrared spectroscopy. In some embodiments, an emitter may include one or more sources that are configured as a point optical source. In addition, the emitter may be operated in a manner that allows for the measurement of an analyte like glucose. In embodiments, the emitter may comprise a plurality of LEDs that emit a sequence of pulses of optical radiation across a spectrum of wavelengths. In addition, in order to achieve the desired SNR for detecting analytes like glucose, the emitter may be driven using a progression from low power to higher power. The emitter may also have its duty cycle modified to achieve a desired SNR.

In an embodiment, a multi-stream emitter for a noninvasive, physiological device configured to transmit optical radiation in a tissue site comprises: a set of optical sources arranged as a point optical source; and a driver configured to drive the at least one light emitting diode and at least one optical source to transmit near-infrared optical radiation at sufficient power to measure an analyte in tissue that responds to near-infrared optical radiation.

In an embodiment, an emitter for a noninvasive, physiological device configured to transmit optical radiation in a tissue site comprises: a point optical source comprising an optical source configured to transmit infrared and near-infrared optical radiation to a tissue site; and a driver configured to drive the point optical source at a sufficient power and noise tolerance to effectively provide attenuated optical radiation from a tissue site that indicates an amount of glucose in the tissue site.

In an embodiment, a method of transmitting a stream of pulses of optical radiation in a tissue site is provided. At least one pulse of infrared optical radiation having a first pulse width is transmitted at a first power. At least one pulse of near-infrared optical radiation is transmitted at a power that is higher than the first power.

In an embodiment, a method of transmitting a stream of pulses of optical radiation in a tissue site is provided. At least one pulse of infrared optical radiation having a first pulse width is transmitted at a first power. At least one pulse of near-infrared optical radiation is then transmitted, at a second power that is higher than the first power.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIGS. 15G and 15H illustrate embodiments of connector features that can be used with any of the sensors described herein;

FIGS. 16A and 16B illustrate embodiments of disposable optical sensors;

DETAILED DESCRIPTION

Figure 1:
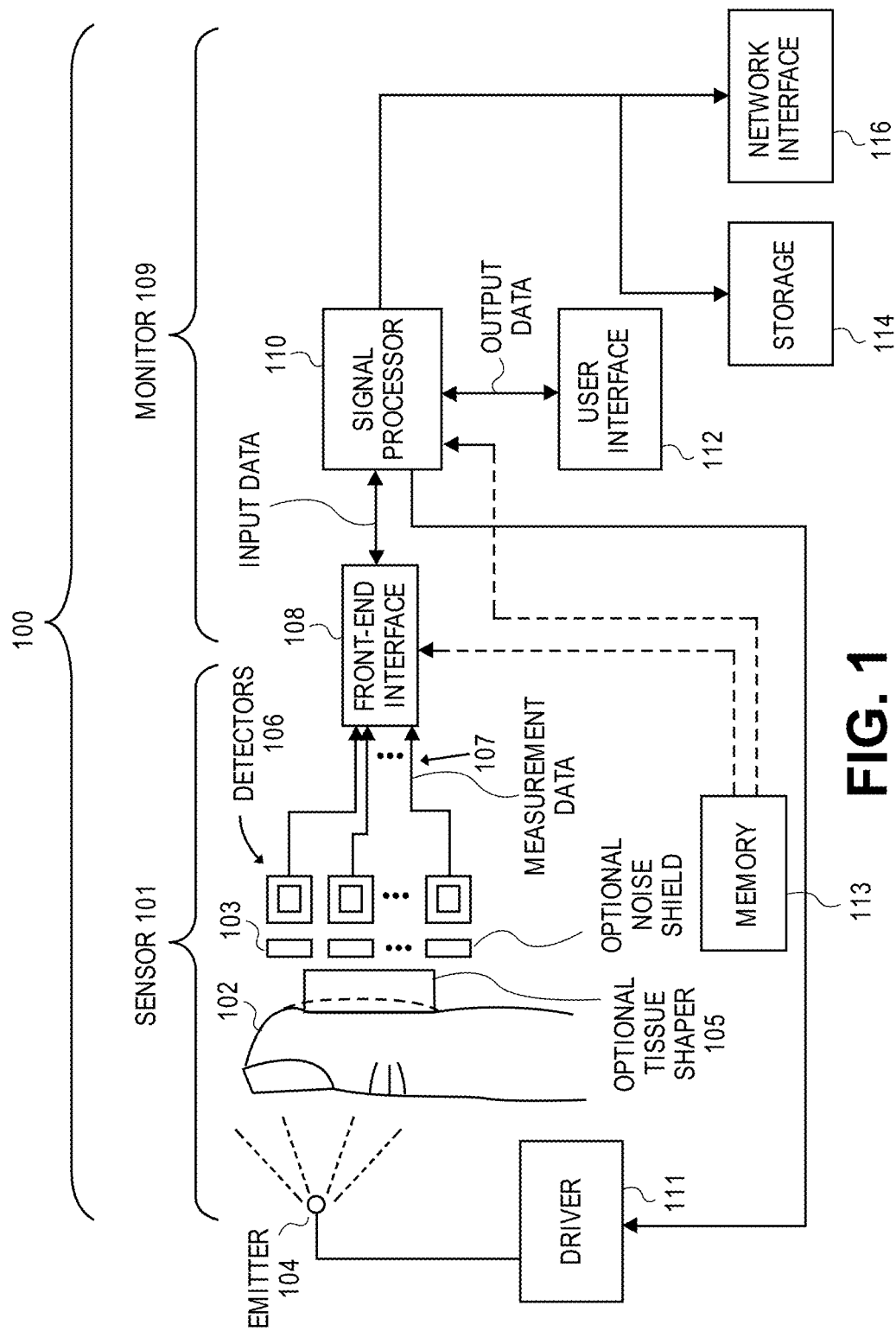
FIG. 1 illustrates a block diagram of an example data collection system capable of noninvasively measuring one or more blood analytes in a monitored patient, according to an embodiment of the disclosure.

The present disclosure generally relates to non-invasive medical devices. In the present disclosure, a sensor can measure various blood constituents or analytes noninvasively using multi-stream spectroscopy. In an embodiment, the multi-stream spectroscopy can employ visible, infrared and near infrared wavelengths. As disclosed herein, the sensor is capable of noninvasively measuring blood analytes or percentages thereof (e.g., saturation) based on various combinations of features and components.

In various embodiments, the present disclosure relates to an interface for a noninvasive glucose sensor that comprises a front-end adapted to receive an input signals from optical detectors and provide corresponding output signals. The front-end may comprise, among other things, switched capacitor circuits or transimpedance amplifiers. In an embodiment, the front-end may comprise switched capacitor circuits that are configured to convert the output of sensor's detectors into a digital signal. In another embodiment, the front-end may comprise transimpedance amplifiers. These transimpedance amplifiers may be configured to match one or more photodiodes in a detector based on a noise model that accounts for characteristics, such as the impedance, of the transimpedance amplifier, characteristics of each photodiode, such as the impedance, and the number of photodiodes coupled to the transimpedance amplifier.

In the present disclosure, the front-ends are employed in a sensor that measures various blood analytes noninvasively using multi-stream spectroscopy. In an embodiment, the multi-stream spectroscopy can employ visible, infrared and near infrared wavelengths. As disclosed herein, the sensor is capable of noninvasively measuring blood analytes, such as glucose, total hemoglobin, methemoglobin, oxygen content, and the like, based on various combinations of features and components.

In an embodiment, a physiological sensor includes a detector housing that can be coupled to a measurement site, such as a patient's finger. The sensor housing can include a curved bed that can generally conform to the shape of the measurement site. In addition, the curved bed can include a protrusion shaped to increase an amount of light radiation from the measurement site. In an embodiment, the protrusion is used to thin out the measurement site. This allows the light radiation to pass through less tissue, and accordingly is attenuated less. In an embodiment, the protrusion can be used to increase the area from which attenuated light can be measured. In an embodiment, this is done through the use of a lens which collects attenuated light exiting the measurement site and focuses onto one or more detectors. The protrusion can advantageously include plastic, including a hard opaque plastic, such as a black or other colored plastic, helpful in reducing light noise. In an embodiment, such light noise includes light that would otherwise be detected at a photodetector that has not been attenuated by tissue of the measurement site of a patient sufficient to cause the light to adequately included information indicative of one or more physiological parameters of the patient. Such light noise includes light piping.

In an embodiment, the protrusion can be formed from the curved bed, or can be a separate component that is positionable with respect to the bed. In an embodiment, a lens made from any appropriate material is used as the protrusion. The protrusion can be convex in shape. The protrusion can also be sized and shaped to conform the measurement site into a flat or relatively flat surface. The protrusion can also be sized to conform the measurement site into a rounded surface, such as, for example, a concave or convex surface. The protrusion can include a cylindrical or partially cylindrical shape. The protrusion can be sized or shaped differently for different types of patients, such as an adult, child, or infant. The protrusion can also be sized or shaped differently for different measurement sites, including, for example, a finger, toe, hand, foot, ear, forehead, or the like. The protrusion can thus be helpful in any type of noninvasive sensor. The external surface of the protrusion can include one or more openings or windows. The openings can be made from glass to allow attenuated light from a measurement site, such as a finger, to pass through to one or more detectors. Alternatively, some of all of the protrusion can be a lens, such as a partially cylindrical lens.

The sensor can also include a shielding, such as a metal enclosure as described below or embedded within the protrusion to reduce noise. The shielding can be constructed from a conductive material, such as copper, in the form of a metal cage or enclosure, such as a box. The shielding can include a second set of one or more openings or windows. The second set of openings can be made from glass and allow light that has passed through the first set of windows of the external surface of the protrusion to pass through to one or more detectors that can be enclosed, for example, as described below.

In various embodiments, the shielding can include any substantially transparent, conductive material placed in the optical path between an emitter and a detector. The shielding can be constructed from a transparent material, such as glass, plastic, and the like. The shielding can have an electrically conductive material or coating that is at least partially transparent. The electrically conductive coating can be located on one or both sides of the shielding, or within the body of the shielding. In addition, the electrically conductive coating can be uniformly spread over the shielding or may be patterned. Furthermore, the coating can have a uniform or varying thickness to increase or optimize its shielding effect. The shielding can be helpful in virtually any type of noninvasive sensor that employs spectroscopy.

In an embodiment, the sensor can also include a heat sink. In an embodiment, the heat sink can include a shape that is functional in its ability to dissipate excess heat and aesthetically pleasing to the wearer. For example, the heat sink can be configured in a shape that maximizes surface area to allow for greater dissipation of heat. In an embodiment, the heat sink includes a metalicized plastic, such as plastic including carbon and aluminum to allow for improved thermal conductivity and diffusivity. In an embodiment, the heat sink can advantageously be inexpensively molded into desired shapes and configurations for aesthetic and functional purposes. For example, the shape of the heat sink can be a generally curved surface and include one or more fins, undulations, grooves or channels, or combs.

The sensor can include photocommunicative components, such as an emitter, a detector, and other components. The emitter can include a plurality of sets of optical sources that, in an embodiment, are arranged together as a point source. The various optical sources can emit a sequence of optical radiation pulses at different wavelengths towards a measurement site, such as a patient's finger. Detectors can then detect optical radiation from the measurement site. The optical sources and optical radiation detectors can operate at any appropriate wavelength, including, as discussed herein, infrared, near infrared, visible light, and ultraviolet. In addition, the optical sources and optical radiation detectors can operate at any appropriate wavelength, and such modifications to the embodiments desirable to operate at any such wavelength will be apparent to those skilled in the art.

In certain embodiments, multiple detectors are employed and arranged in a spatial geometry. This spatial geometry provides a diversity of path lengths among at least some of the detectors and allows for multiple bulk and pulsatile measurements that are robust. Each of the detectors can provide a respective output stream based on the detected optical radiation, or a sum of output streams can be provided from multiple detectors. In some embodiments, the sensor can also include other components, such as one or more heat sinks and one or more thermistors.

The spatial configuration of the detectors provides a geometry having a diversity of path lengths among the detectors. For example, a detector in the sensor may comprise multiple detectors that are arranged to have a sufficient difference in mean path length to allow for noise cancellation and noise reduction. In addition, walls may be used to separate individual photodetectors and prevent mixing of detected optical radiation between the different locations on the measurement site. A window may also be employed to facilitate the passing of optical radiation at various wavelengths for measuring glucose in the tissue.

In the present disclosure, a sensor may measure various blood constituents or analytes noninvasively using spectroscopy and a recipe of various features. As disclosed herein, the sensor is capable of non-invasively measuring blood analytes, such as, glucose, total hemoglobin, methemoglobin, oxygen content, and the like. In an embodiment, the spectroscopy used in the sensor can employ visible, infrared and near infrared wavelengths. The sensor may comprise an emitter, a detector, and other components. In some embodiments, the sensor may also comprise other components, such as one or more heat sinks and one or more thermistors.

In various embodiments, the sensor may also be coupled to one or more companion devices that process and/or display the sensor's output. The companion devices may comprise various components, such as a sensor front-end, a signal processor, a display, a network interface, a storage device or memory, etc.

A sensor can include photocommunicative components, such as an emitter, a detector, and other components. The emitter is configured as a point optical source that comprises a plurality of LEDs that emit a sequence of pulses of optical radiation across a spectrum of wavelengths. In some embodiments, the plurality of sets of optical sources may each comprise at least one top-emitting LED and at least one super luminescent LED. In some embodiments, the emitter comprises optical sources that transmit optical radiation in the infrared or near-infrared wavelengths suitable for detecting blood analytes like glucose. In order to achieve the desired SNR for detecting analytes like glucose, the emitter may be driven using a progression from low power to higher power. In addition, the emitter may have its duty cycle modified to achieve a desired SNR.

The emitter may be constructed of materials, such as aluminum nitride and may include a heat sink to assist in heat dissipation. A thermistor may also be employed to account for heating effects on the LEDs. The emitter may further comprise a glass window and a nitrogen environment to improve transmission from the sources and prevent oxidative effects.

The sensor can be coupled to one or more monitors that process and/or display the sensor's output. The monitors can include various components, such as a sensor front end, a signal processor, a display, etc.

The sensor can be integrated with a monitor, for example, into a handheld unit including the sensor, a display and user controls. In other embodiments, the sensor can communicate with one or more processing devices. The communication can be via wire(s), cable(s), flex circuit(s), wireless technologies, or other suitable analog or digital communication methodologies and devices to perform those methodologies.

Many of the foregoing arrangements allow the sensor to be attached to the measurement site while the device is attached elsewhere on a patient, such as the patient's arm, or placed at a location near the patient, such as a bed, shelf or table. The sensor or monitor can also provide outputs to a storage device or network interface.

Reference will now be made to the Figures to discuss embodiments of the present disclosure.

FIG. 1 illustrates an example of a data collection system 100. In certain embodiments, the data collection system 100 noninvasively measure a blood analyte, such as oxygen, carbon monoxide, methemoglobin, total hemoglobin, glucose, proteins, glucose, lipids, a percentage thereof (e.g., saturation) or for measuring many other physiologically relevant patient characteristics. The system 100 can also measure additional blood analytes and/or other physiological parameters useful in determining a state or trend of wellness of a patient.

The data collection system 100 can be capable of measuring optical radiation from the measurement site. For example, in some embodiments, the data collection system 100 can employ photodiodes defined in terms of area. In an embodiment, the area is from about 1 $mm^2$-5 $mm^2$ (or higher) that are capable of detecting about 100 nanoamps (nA) or less of current resulting from measured light at full scale. In addition to having its ordinary meaning, the phrase "at full scale" can mean light saturation of a photodiode amplifier (not shown). Of course, as would be understood by a person of skill in the art from the present disclosure, various other sizes and types of photodiodes can be used with the embodiments of the present disclosure.

The data collection system 100 can measure a range of approximately about 2 nA to about 100 nA full scale. The data collection system 100 can also include sensor front-ends that are capable of processing and amplifying current from the detector(s) at signal-to-noise ratios (SNRs) of about 100 decibels (dB) or more, such as about 120 dB in order to measure various desired analytes. The data collection system 100 can operate with a lower SNR if less accuracy is desired for an analyte like glucose.

The data collection system 100 can measure analyte concentrations, including glucose, at least in part by detecting light attenuated by a measurement site 102. The measurement site 102 can be any location on a patient's body, such as a finger, foot, ear lobe, or the like. For convenience, this disclosure is described primarily in the context of a finger measurement site 102. However, the features of the embodiments disclosed herein can be used with other measurement sites 102.

In the depicted embodiment, the system 100 includes an optional tissue thickness adjuster or tissue shaper 105, which can include one or more protrusions, bumps, lenses, or other suitable tissue-shaping mechanisms. In certain embodiments, the tissue shaper 105 is a flat or substantially flat surface that can be positioned proximate the measurement site 102 and that can apply sufficient pressure to cause the tissue of the measurement site 102 to be flat or substantially flat. In other embodiments, the tissue shaper 105 is a convex or substantially convex surface with respect to the measurement site 102. Many other configurations of the tissue shaper 105 are possible. Advantageously, in certain embodiments, the tissue shaper 105 reduces thickness of the measurement site 102 while preventing or reducing occlusion at the measurement site 102. Reducing thickness of the site can advantageously reduce the amount of attenuation of the light because there is less tissue through which the light must travel. Shaping the tissue in to a convex (or alternatively concave) surface can also provide more surface area from which light can be detected.

The embodiment of the data collection system 100 shown also includes an optional noise shield 103. In an embodiment, the noise shield 103 can be advantageously adapted to reduce electromagnetic noise while increasing the transmittance of light from the measurement site 102 to one or more detectors 106 (described below). For example, the noise shield 103 can advantageously include a conductive coated glass or metal grid electrically communicating with one or more other shields of the sensor 101 or electrically grounded. In an embodiment where the noise shield 103 includes conductive coated glass, the coating can advantageously include indium tin oxide. In an embodiment, the indium tin oxide includes a surface resistivity ranging from approximately 30 ohms per square inch to about 500 ohms per square inch. In an embodiment, the resistivity is approximately 30, 200, or 500 ohms per square inch. As would be understood by a person of skill in the art from the present disclosure, other resistivities can also be used which are less than about 30 ohms or more than about 500 ohms. Other conductive materials transparent or substantially transparent to light can be used instead.

In some embodiments, the measurement site 102 is located somewhere along a non-dominant arm or a non-dominant hand, e.g., a right-handed person's left arm or left hand. In some patients, the non-dominant arm or hand can have less musculature and higher fat content, which can result in less water content in that tissue of the patient. Tissue having less water content can provide less interference with the particular wavelengths that are absorbed in a useful manner by blood analytes like glucose. Accordingly, in some embodiments, the data collection system 100 can be used on a person's non-dominant hand or arm.

The data collection system 100 can include a sensor 101 (or multiple sensors) that is coupled to a processing device or physiological monitor 109. In an embodiment, the sensor 101 and the monitor 109 are integrated together into a single unit. In another embodiment, the sensor 101 and the monitor 109 are separate from each other and communicate one with another in any suitable manner, such as via a wired or wireless connection. The sensor 101 and monitor 109 can be attachable and detachable from each other for the convenience of the user or caregiver, for ease of storage, sterility issues, or the like. The sensor 101 and the monitor 109 will now be further described.

In the depicted embodiment shown in FIG. 1, the sensor 101 includes an emitter 104, a tissue shaper 105, a set of detectors 106, and a front-end interface 108. The emitter 104 can serve as the source of optical radiation transmitted towards measurement site 102. As will be described in further detail below, the emitter 104 can include one or more sources of optical radiation, such as LEDs, laser diodes, incandescent bulbs with appropriate frequency-selective filters, combinations of the same, or the like. In an embodiment, the emitter 104 includes sets of optical sources that are capable of emitting visible and near-infrared optical radiation.

In some embodiments, the emitter 104 is used as a point optical source, and thus, the one or more optical sources of the emitter 104 can be located within a close distance to each other, such as within about a 2 mm to about 4 mm. The emitters 104 can be arranged in an array, such as is described in U.S. Publication No. 2006/0211924, filed Sep. 21, 2006, titled "Multiple Wavelength Sensor Emitters," the disclosure of which is hereby incorporated by reference in its entirety. In particular, the emitters 104 can be arranged at least in part as described in paragraphs [0061] through [0068] of the aforementioned publication, which paragraphs are hereby incorporated specifically by reference. Other relative spatial relationships can be used to arrange the emitters 104.

For analytes like glucose, currently available non-invasive techniques often attempt to employ light near the water absorbance minima at or about 1600 nm. Typically, these devices and methods employ a single wavelength or single band of wavelengths at or about 1600 nm. However, to date, these techniques have been unable to adequately consistently measure analytes like glucose based on spectroscopy.

In contrast, the emitter 104 of the data collection system 100 can emit, in certain embodiments, combinations of optical radiation in various bands of interest. For example, in some embodiments, for analytes like glucose, the emitter 104 can emit optical radiation at three (3) or more wavelengths between about 1600 nm to about 1700 nm. In particular, the emitter 104 can emit optical radiation at or about 1610 nm, about 1640 nm, and about 1665 nm. In some circumstances, the use of three wavelengths within about 1600 nm to about 1700 nm enable sufficient SNRs of about 100 dB, which can result in a measurement accuracy of about 20 mg/dL or better for analytes like glucose.

In other embodiments, the emitter 104 can use two (2) wavelengths within about 1600 nm to about 1700 nm to advantageously enable SNRs of about 85 dB, which can result in a measurement accuracy of about 25-30 mg/dL or better for analytes like glucose. Furthermore, in some embodiments, the emitter 104 can emit light at wavelengths above about 1670 nm. Measurements at these wavelengths can be advantageously used to compensate or confirm the contribution of protein, water, and other non-hemoglobin species exhibited in measurements for analytes like glucose conducted between about 1600 nm and about 1700 nm. Of course, other wavelengths and combinations of wavelengths can be used to measure analytes and/or to distinguish other types of tissue, fluids, tissue properties, fluid properties, combinations of the same or the like.

For example, the emitter 104 can emit optical radiation across other spectra for other analytes. In particular, the emitter 104 can employ light wavelengths to measure various blood analytes or percentages (e.g., saturation) thereof. For example, in one embodiment, the emitter 104 can emit optical radiation in the form of pulses at wavelengths about 905 nm, about 1050 nm, about 1200 nm, about 1300 nm, about 1330 nm, about 1610 nm, about 1640 nm, and about 1665 nm. In another embodiment, the emitter 104 can emit optical radiation ranging from about 860 nm to about 950 nm, about 950 nm to about 1100 nm, about 1100 nm to about 1270 nm, about 1250 nm to about 1350 nm, about 1300 nm to about 1360 nm, and about 1590 nm to about 1700 nm. Of course, the emitter 104 can transmit any of a variety of wavelengths of visible or near-infrared optical radiation.

Due to the different responses of analytes to the different wavelengths, certain embodiments of the data collection system 100 can advantageously use the measurements at these different wavelengths to improve the accuracy of measurements. For example, the measurements of water from visible and infrared light can be used to compensate for water absorbance that is exhibited in the near-infrared wavelengths.

As briefly described above, the emitter 104 can include sets of light-emitting diodes (LEDs) as its optical source. The emitter 104 can use one or more top-emitting LEDs. In particular, in some embodiments, the emitter 104 can include top-emitting LEDs emitting light at about 850 nm to 1350 nm.

The emitter 104 can also use super luminescent LEDs (SLEDs) or side-emitting LEDs. In some embodiments, the emitter 104 can employ SLEDs or side-emitting LEDs to emit optical radiation at about 1600 nm to about 1800 nm. Emitter 104 can use SLEDs or side-emitting LEDs to transmit near infrared optical radiation because these types of sources can transmit at high power or relatively high power, e.g., about 40 mW to about 100 mW. This higher power capability can be useful to compensate or overcome the greater attenuation of these wavelengths of light in tissue and water. For example, the higher power emission can effectively compensate and/or normalize the absorption signal for light in the mentioned wavelengths to be similar in amplitude and/or effect as other wavelengths that can be detected by one or more photodetectors after absorption. However, the embodiments of the present disclosure do not necessarily require the use of high power optical sources. For example, some embodiments may be configured to measure analytes, such as total hemoglobin (tHb), oxygen saturation ($SpO_2$), carboxyhemoglobin, methemoglobin, etc., without the use of high power optical sources like side emitting LEDs. Instead, such embodiments may employ other types of optical sources, such as top emitting LEDs. Alternatively, the emitter 104 can use other types of sources of optical radiation, such as a laser diode, to emit near-infrared light into the measurement site 102.

In addition, in some embodiments, in order to assist in achieving a comparative balance of desired power output between the LEDs, some of the LEDs in the emitter 104 can have a filter or covering that reduces and/or cleans the optical radiation from particular LEDs or groups of LEDs. For example, since some wavelengths of light can penetrate through tissue relatively well, LEDs, such as some or all of the top-emitting LEDs can use a filter or covering, such as a cap or painted dye. This can be useful in allowing the emitter 104 to use LEDs with a higher output and/or to equalize intensity of LEDs.

The data collection system 100 also includes a driver 111 that drives the emitter 104. The driver 111 can be a circuit or the like that is controlled by the monitor 109. For example, the driver 111 can provide pulses of current to the emitter 104. In an embodiment, the driver 111 drives the emitter 104 in a progressive fashion, such as in an alternating manner. The driver 111 can drive the emitter 104 with a series of pulses of about 1 milliwatt (mW) for some wavelengths that can penetrate tissue relatively well and from about 40 mW to about 100 mW for other wavelengths that tend to be significantly absorbed in tissue. A wide variety of other driving powers and driving methodologies can be used in various embodiments.

The driver 111 can be synchronized with other parts of the sensor 101 and can minimize or reduce jitter in the timing of pulses of optical radiation emitted from the emitter 104. In some embodiments, the driver 111 is capable of driving the emitter 104 to emit optical radiation in a pattern that varies by less than about 10 parts-per-million.

The detectors 106 capture and measure light from the measurement site 102. For example, the detectors 106 can capture and measure light transmitted from the emitter 104 that has been attenuated or reflected from the tissue in the measurement site 102. The detectors 106 can output a detector signal 107 responsive to the light captured or measured. The detectors 106 can be implemented using one or more photodiodes, phototransistors, or the like.

In addition, the detectors 106 can be arranged with a spatial configuration to provide a variation of path lengths among at least some of the detectors 106. That is, some of the detectors 106 can have the substantially, or from the perspective of the processing algorithm, effectively, the same path length from the emitter 104. However, according to an embodiment, at least some of the detectors 106 can have a different path length from the emitter 104 relative to other of the detectors 106. Variations in path lengths can be helpful in allowing the use of a bulk signal stream from the detectors 106. In some embodiments, the detectors 106 may employ a linear spacing, a logarithmic spacing, or a two or three dimensional matrix of spacing, or any other spacing scheme in order to provide an appropriate variation in path lengths.

The front end interface 108 provides an interface that adapts the output of the detectors 106, which is responsive to desired physiological parameters. For example, the front end interface 108 can adapt a signal 107 received from one or more of the detectors 106 into a form that can be processed by the monitor 109, for example, by a signal processor 110 in the monitor 109. The front end interface 108 can have its components assembled in the sensor 101, in the monitor 109, in connecting cabling (if used), combinations of the same, or the like. The location of the front end interface 108 can be chosen based on various factors including space desired for components, desired noise reductions or limits, desired heat reductions or limits, and the like.

The front end interface 108 can be coupled to the detectors 106 and to the signal processor 110 using a bus, wire, electrical or optical cable, flex circuit, or some other form of signal connection. The front end interface 108 can also be at least partially integrated with various components, such as the detectors 106. For example, the front end interface 108 can include one or more integrated circuits that are on the same circuit board as the detectors 106. Other configurations can also be used.

The front end interface 108 can be implemented using one or more amplifiers, such as transimpedance amplifiers, that are coupled to one or more analog to digital converters (ADCs) (which can be in the monitor 109), such as a sigma-delta ADC. A transimpedance-based front end interface 108 can employ single-ended circuitry, differential circuitry, and/or a hybrid configuration. A transimpedance-based front end interface 108 can be useful for its sampling rate capability and freedom in modulation/demodulation algorithms. For example, this type of front end interface 108 can advantageously facilitate the sampling of the ADCs being synchronized with the pulses emitted from the emitter 104.

The ADC or ADCs can provide one or more outputs into multiple channels of digital information for processing by the signal processor 110 of the monitor 109. Each channel can correspond to a signal output from a detector 106.

In some embodiments, a programmable gain amplifier (PGA) can be used in combination with a transimpedance-based front end interface 108. For example, the output of a transimpedance-based front end interface 108 can be output to a PGA that is coupled with an ADC in the monitor 109. A PGA can be useful in order to provide another level of amplification and control of the stream of signals from the detectors 106. Alternatively, the PGA and ADC components can be integrated with the transimpedance-based front end interface 108 in the sensor 101.

In another embodiment, the front end interface 108 can be implemented using switched-capacitor circuits. A switched-capacitor-based front end interface 108 can be useful for, in certain embodiments, its resistor-free design and analog averaging properties. In addition, a switched-capacitor-based front end interface 108 can be useful because it can provide a digital signal to the signal processor 110 in the monitor 109.

As shown in FIG. 1, the monitor 109 can include the signal processor 110 and a user interface, such as a display 112. The monitor 109 can also include optional outputs alone or in combination with the display 112, such as a storage device 114 and a network interface 116. In an embodiment, the signal processor 110 includes processing logic that determines measurements for desired analytes, such as glucose, based on the signals received from the detectors 106. The signal processor 110 can be implemented using one or more microprocessors or subprocessors (e.g., cores), digital signal processors, application specific integrated circuits (ASICs), field programmable gate arrays (FPGAs), combinations of the same, and the like.

The signal processor 110 can provide various signals that control the operation of the sensor 101. For example, the signal processor 110 can provide an emitter control signal to the driver 111. This control signal can be useful in order to synchronize, minimize, or reduce jitter in the timing of pulses emitted from the emitter 104. Accordingly, this control signal can be useful in order to cause optical radiation pulses emitted from the emitter 104 to follow a precise timing and consistent pattern. For example, when a transimpedance-based front end interface 108 is used, the control signal from the signal processor 110 can provide synchronization with the ADC in order to avoid aliasing, cross-talk, and the like. As also shown, an optional memory 113 can be included in the front-end interface 108 and/or in the signal processor 110. This memory 113 can serve as a buffer or storage location for the front-end interface 108 and/or the signal processor 110, among other uses.

The user interface 112 can provide an output, e.g., on a display, for presentation to a user of the data collection system 100. The user interface 112 can be implemented as a touch-screen display, an LCD display, an organic LED display, or the like. In addition, the user interface 112 can be manipulated to allow for measurement on the non-dominant side of patient. For example, the user interface 112 can include a flip screen, a screen that can be moved from one side to another on the monitor 109, or can include an ability to reorient its display indicia responsive to user input or device orientation. In alternative embodiments, the data collection system 100 can be provided without a user interface 112 and can simply provide an output signal to a separate display or system.

A storage device 114 and a network interface 116 represent other optional output connections that can be included in the monitor 109. The storage device 114 can include any computer-readable medium, such as a memory device, hard disk storage, EEPROM, flash drive, or the like. The various software and/or firmware applications can be stored in the storage device 114, which can be executed by the signal processor 110 or another processor of the monitor 109. The network interface 116 can be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the monitor 109 to communicate and share data with other devices. The monitor 109 can also include various other components not shown, such as a microprocessor, graphics processor, or controller to output the user interface 112, to control data communications, to compute data trending, or to perform other operations.

Although not shown in the depicted embodiment, the data collection system 100 can include various other components or can be configured in different ways. For example, the sensor 101 can have both the emitter 104 and detectors 106 on the same side of the measurement site 102 and use reflectance to measure analytes. The data collection system 100 can also include a sensor that measures the power of light emitted from the emitter 104.

FIGS. 2A through 2D illustrate example monitoring devices 200 in which the data collection system 100 can be housed. Advantageously, in certain embodiments, some or all of the example monitoring devices 200 shown can have a shape and size that allows a user to operate it with a single hand or attach it, for example, to a patient's body or limb. Although several examples are shown, many other monitoring device configurations can be used to house the data collection system 100. In addition, certain of the features of the monitoring devices 200 shown in FIGS. 2A through 2D can be combined with features of the other monitoring devices 200 shown.

Figure 2A:
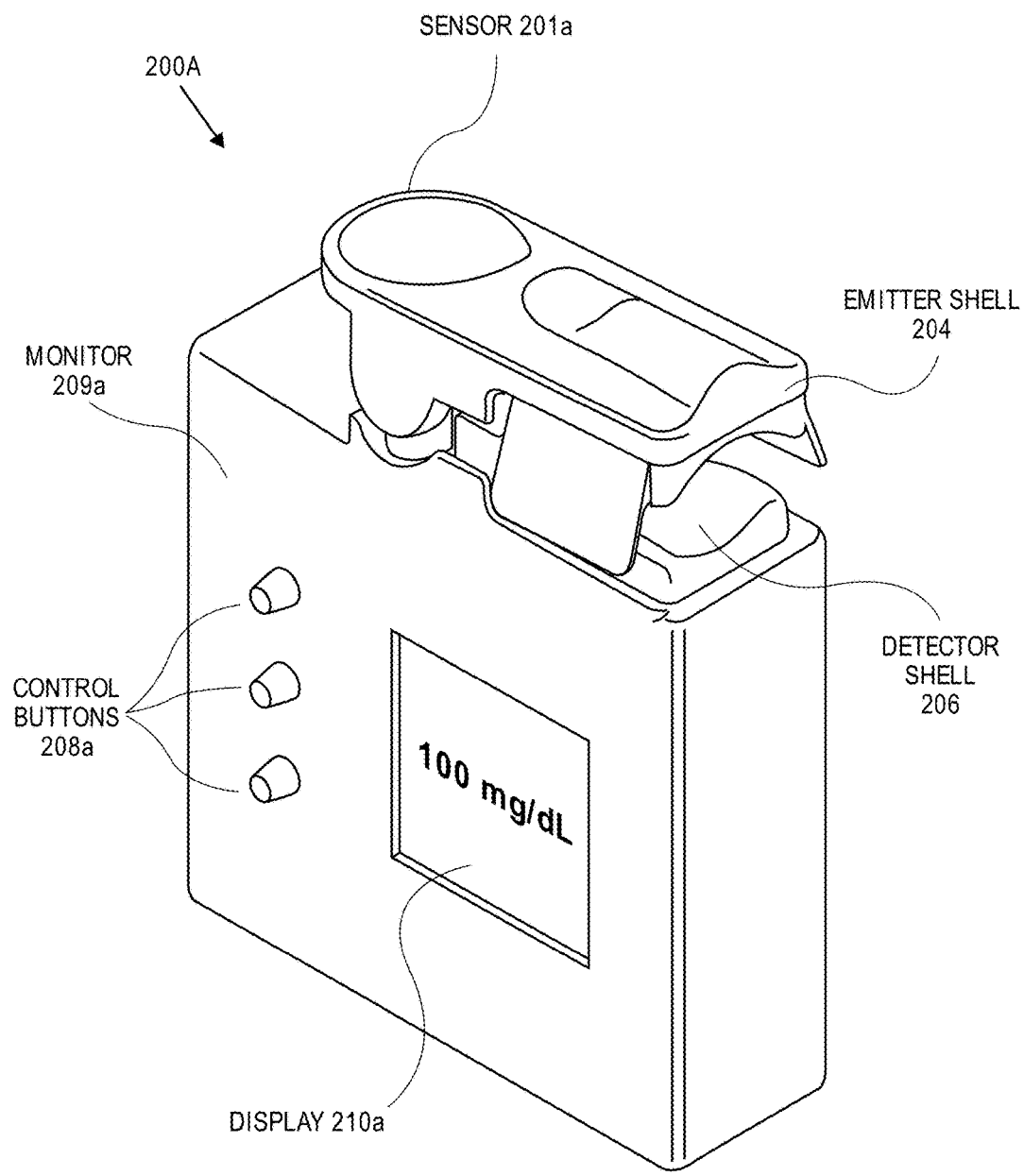
FIGS. 2A-2D illustrate an exemplary handheld monitor and an exemplary noninvasive optical sensor of the patient monitoring system of FIG. 1, according to embodiments of the disclosure.

Referring specifically to FIG. 2A, an example monitoring device 200A is shown, in which a sensor 201a and a monitor 209a are integrated into a single unit. The monitoring device 200A shown is a handheld or portable device that can measure glucose and other analytes in a patient's finger. The sensor 201a includes an emitter shell 204a and a detector shell 206a. The depicted embodiment of the monitoring device 200A also includes various control buttons 208a and a display 210a.

The sensor 201a can be constructed of white material used for reflective purposes (such as white silicone or plastic), which can increase the usable signal at the detector 106 by forcing light back into the sensor 201a. Pads in the emitter shell 204a and the detector shell 206a can contain separated windows to prevent or reduce mixing of light signals, for example, from distinct quadrants on a patient's finger. In addition, these pads can be made of a relatively soft material, such as a gel or foam, in order to conform to the shape, for example, of a patient's finger. The emitter shell 204a and the detector shell 206a can also include absorbing black or grey material portions to prevent or reduce ambient light from entering into the sensor 201a.

In some embodiments, some or all portions of the emitter shell 204a and/or detector shell 206a can be detachable and/or disposable. For example, some or all portions of the shells 204a and 206a can be removable pieces. The removability of the shells 204a and 206a can be useful for sanitary purposes or for sizing the sensor 201a to different patients. The monitor 209a can include a fitting, slot, magnet, or other connecting mechanism to allow the sensor 201c to be removably attached to the monitor 209a.

The monitoring device 200a also includes optional control buttons 208a and a display 210a that can allow the user to control the operation of the device. For example, a user can operate the control buttons 208a to view one or more measurements of various analytes, such as glucose. In addition, the user can operate the control buttons 208a to view other forms of information, such as graphs, histograms, measurement data, trend measurement data, parameter combination views, wellness indications, and the like. Many parameters, trends, alarms and parameter displays could be output to the display 210a, such as those that are commercially available through a wide variety of noninvasive monitoring devices from Masimo® Corporation of Irvine, Calif.

Furthermore, the controls 208a and/or display 210a can provide functionality for the user to manipulate settings of the monitoring device 200a, such as alarm settings, emitter settings, detector settings, and the like. The monitoring device 200a can employ any of a variety of user interface designs, such as frames, menus, touch-screens, and any type of button.

Figure 2B:
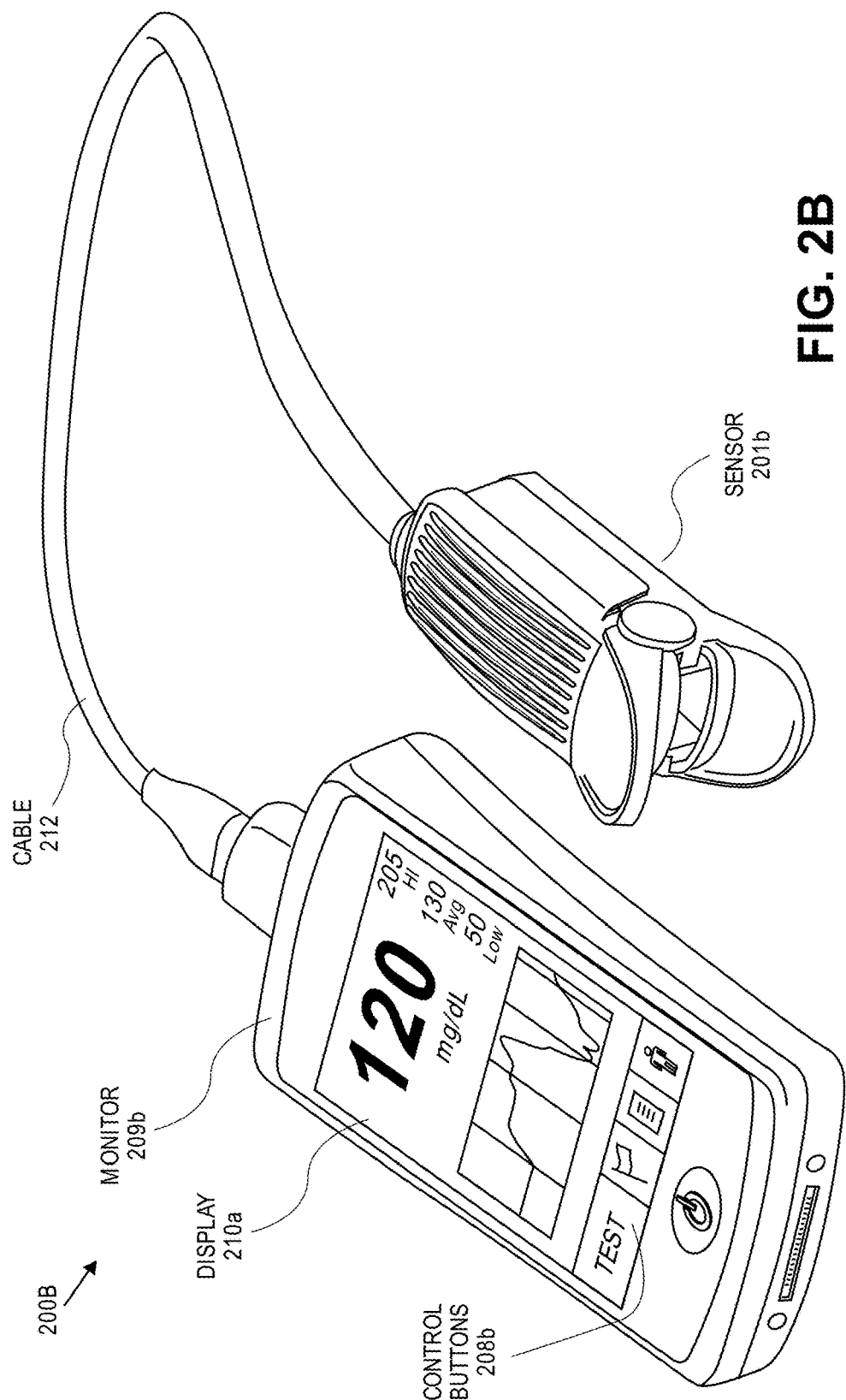

FIG. 2B illustrates another example of a monitoring device 200B. In the depicted embodiment, the monitoring device 200B includes a finger clip sensor 201b connected to a monitor 209b via a cable 212. In the embodiment shown, the monitor 209b includes a display 210b, control buttons 208b and a power button. Moreover, the monitor 209b can advantageously include electronic processing, signal processing, and data storage devices capable of receiving signal data from said sensor 201b, processing the signal data to determine one or more output measurement values indicative of one or more physiological parameters of a monitored patient, and displaying the measurement values, trends of the measurement values, combinations of measurement values, and the like.

The cable 212 connecting the sensor 201b and the monitor 209b can be implemented using one or more wires, optical fiber, flex circuits, or the like. In some embodiments, the cable 212 can employ twisted pairs of conductors in order to minimize or reduce cross-talk of data transmitted from the sensor 201b to the monitor 209b. Various lengths of the cable 212 can be employed to allow for separation between the sensor 201b and the monitor 209b. The cable 212 can be fitted with a connector (male or female) on either end of the cable 212 so that the sensor 201b and the monitor 209b can be connected and disconnected from each other. Alternatively, the sensor 201b and the monitor 209b can be coupled together via a wireless communication link, such as an infrared link, radio frequency channel, or any other wireless communication protocol and channel.

The monitor 209b can be attached to the patient. For example, the monitor 209b can include a belt clip or straps (see, e.g., FIG. 2C) that facilitate attachment to a patient's belt, arm, leg, or the like. The monitor 209b can also include a fitting, slot, magnet, LEMO snap-click connector, or other connecting mechanism to allow the cable 212 and sensor 201b to be attached to the monitor 209B.

The monitor 209b can also include other components, such as a speaker, power button, removable storage or memory (e.g., a flash card slot), an AC power port, and one or more network interfaces, such as a universal serial bus interface or an Ethernet port. For example, the monitor 209b can include a display 210b that can indicate a measurement for glucose, for example, in mg/dL. Other analytes and forms of display can also appear on the monitor 209b.

In addition, although a single sensor 201b with a single monitor 209b is shown, different combinations of sensors and device pairings can be implemented. For example, multiple sensors can be provided for a plurality of differing patient types or measurement sites or even patient fingers.

Figure 2C:
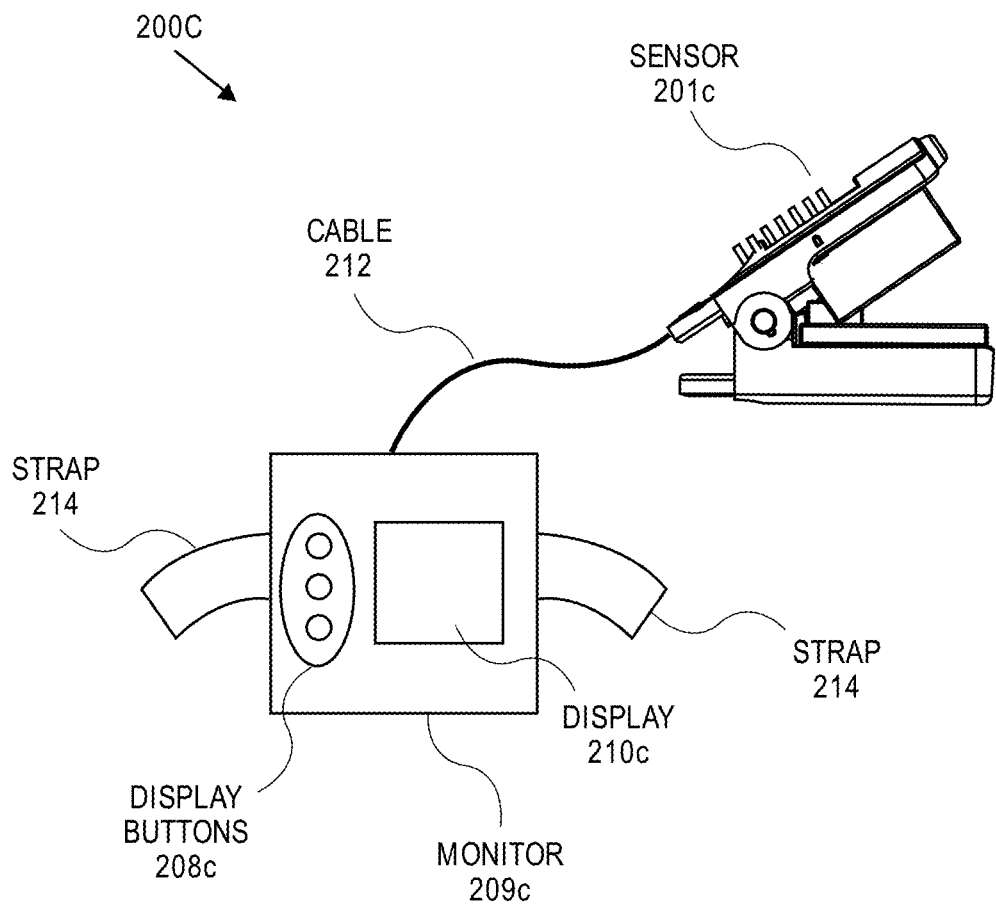

FIG. 2C illustrates yet another example of monitoring device 200C that can house the data collection system 100. Like the monitoring device 200B, the monitoring device 200C includes a finger clip sensor 201c connected to a monitor 209c via a cable 212. The cable 212 can have all of the features described above with respect to FIG. 2B. The monitor 209c can include all of the features of the monitor 200B described above. For example, the monitor 209c includes buttons 208c and a display 210c. The monitor 209c shown also includes straps 214c that allow the monitor 209c to be attached to a patient's limb or the like.

Figure 2D:
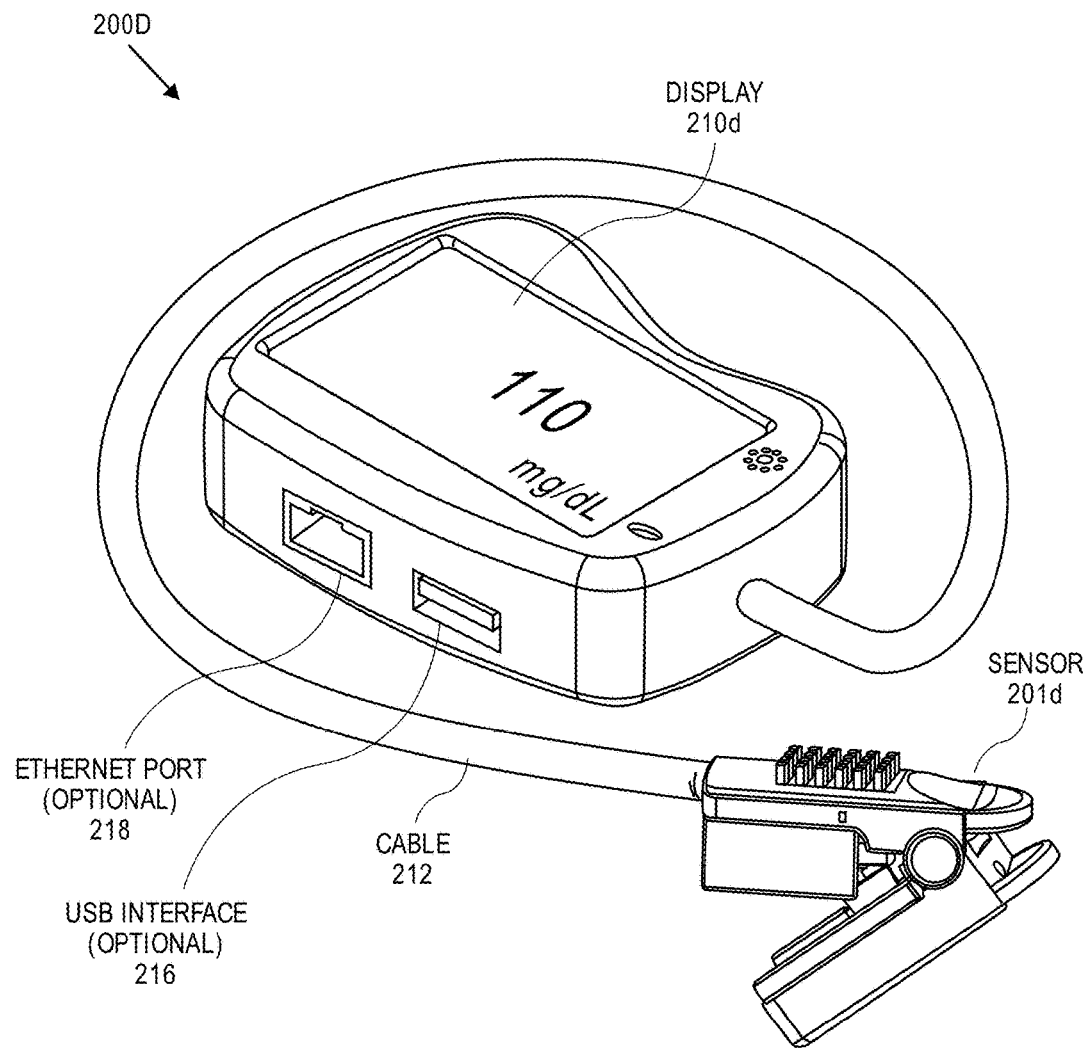

FIG. 2D illustrates yet another example of monitoring device 200D that can house the data collection system 100. Like the monitoring devices 200B and 200C, the monitoring device 200D includes a finger clip sensor 201d connected to a monitor 209d via a cable 212. The cable 212 can have all of the features described above with respect to FIG. 2B. In addition to having some or all of the features described above with respect to FIGS. 2B and 2C, the monitoring device 200D includes an optional universal serial bus (USB) port 216 and an Ethernet port 218. The USB port 216 and the Ethernet port 218 can be used, for example, to transfer information between the monitor 209d and a computer (not shown) via a cable. Software stored on the computer can provide functionality for a user to, for example, view physiological data and trends, adjust settings and download firmware updates to the monitor 209b, and perform a variety of other functions. The USB port 216 and the Ethernet port 218 can be included with the other monitoring devices 200A, 200B, and 200C described above.

Figure 3A:
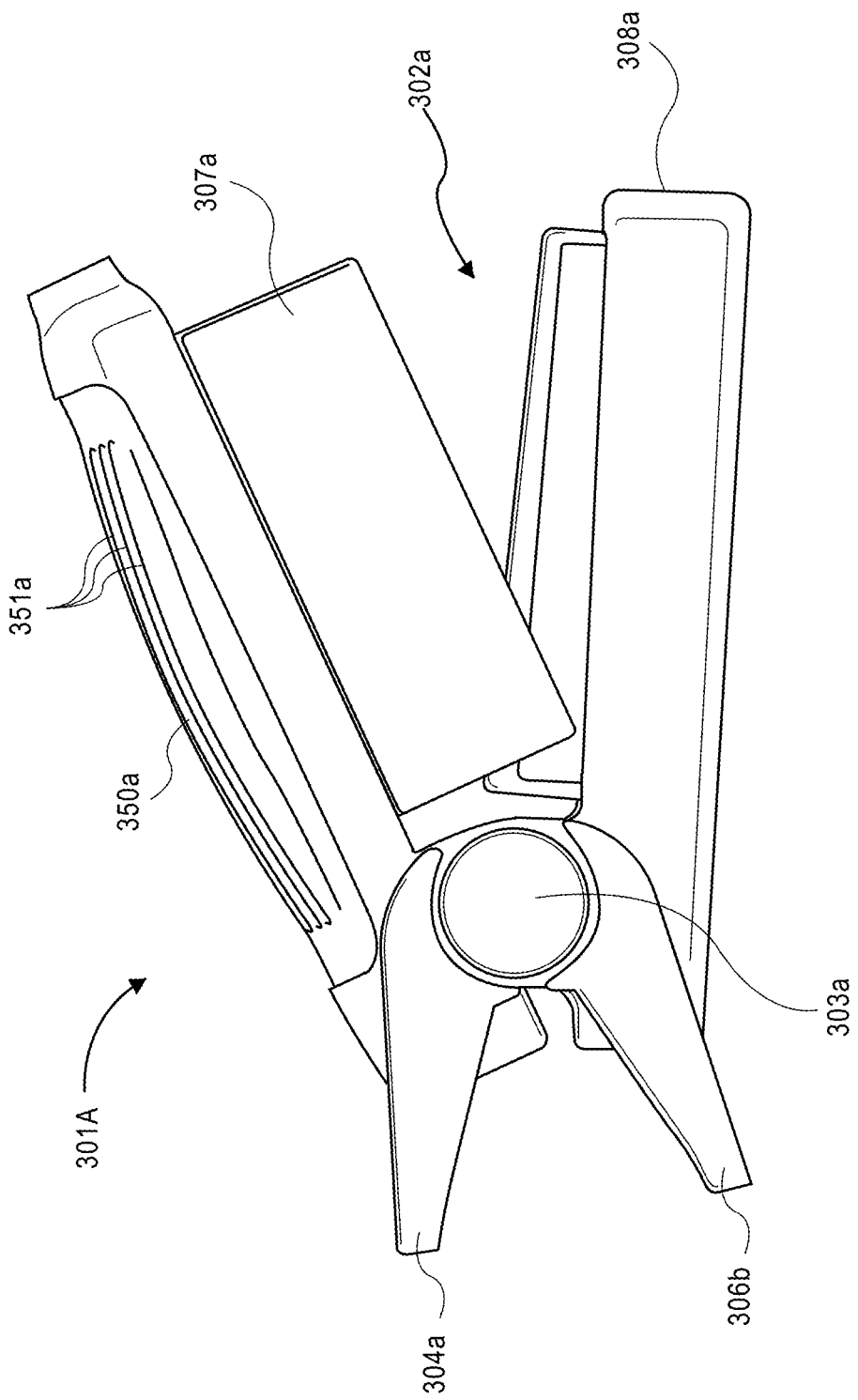
FIGS. 3A-3C illustrate side and perspective views of an exemplary noninvasive sensor housing including a finger bed protrusion and heat sink, according to an embodiment of the disclosure.
Figure 3B:
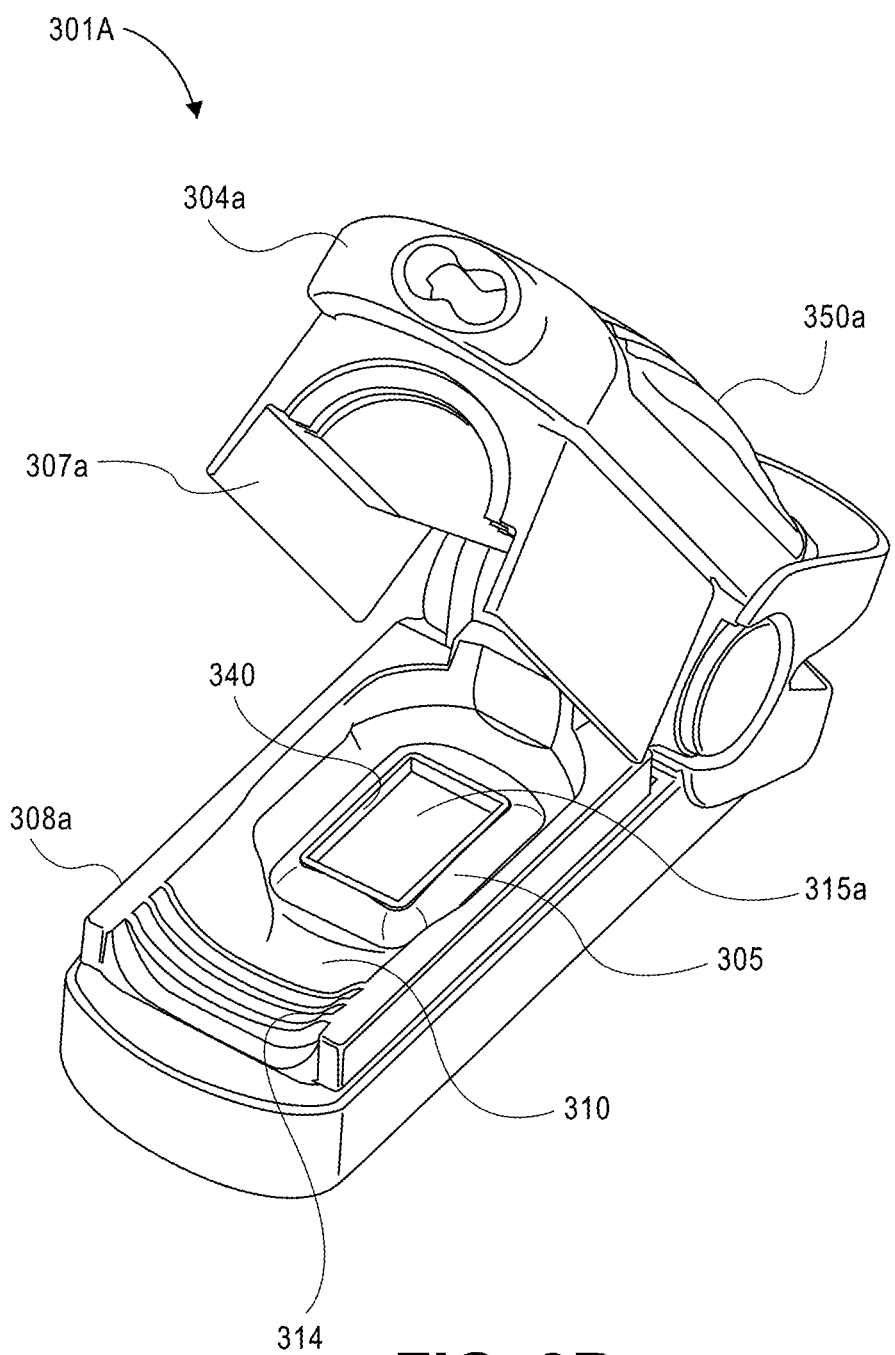
Figure 3C:
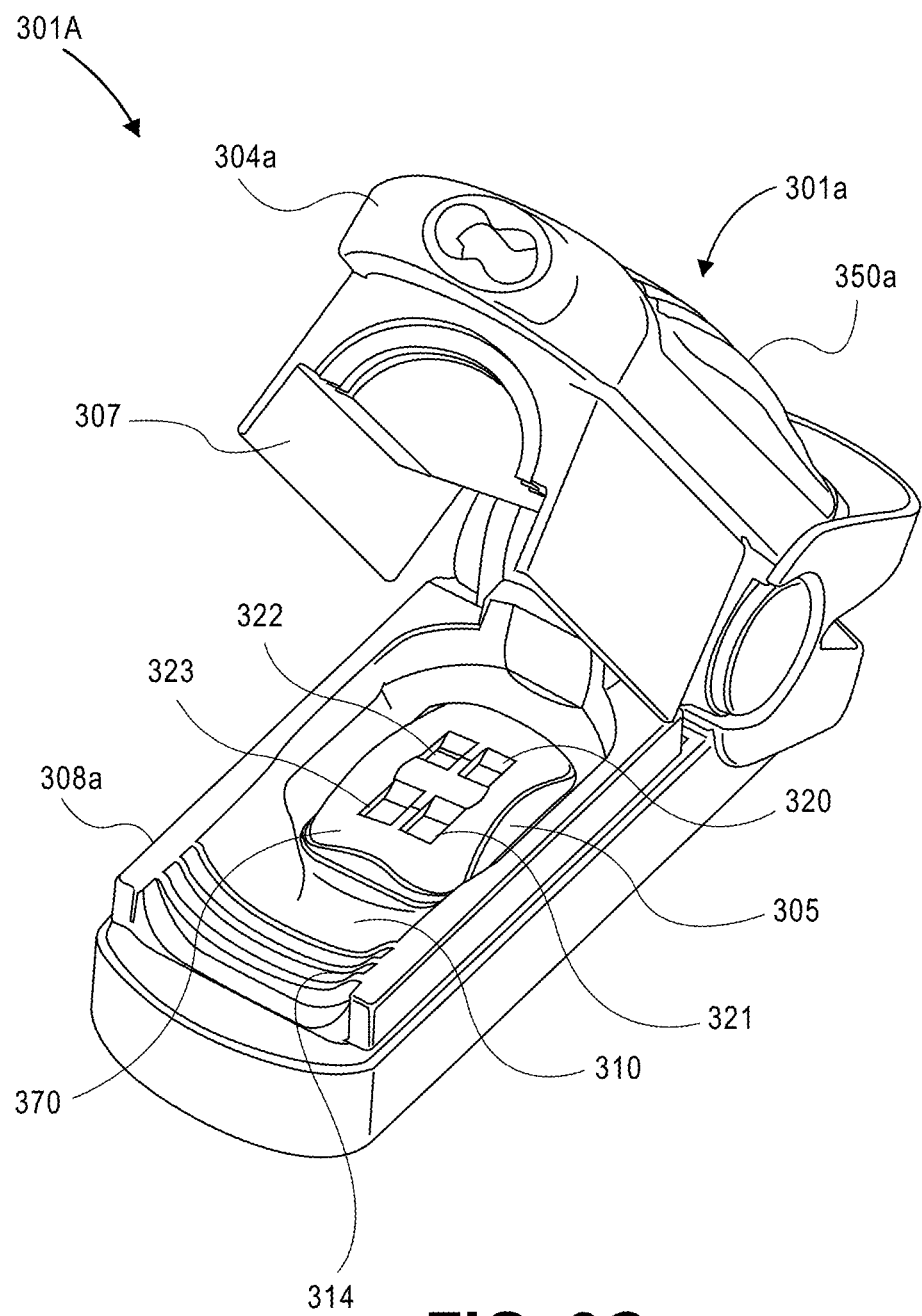

FIGS. 3A through 3C illustrate more detailed examples of embodiments of a sensor 301a. The sensor 301a shown can include all of the features of the sensors 100 and 200 described above.

Referring to FIG. 3A, the sensor 301a in the depicted embodiment is a clothespin-shaped clip sensor that includes an enclosure 302a for receiving a patient's finger. The enclosure 302a is formed by an upper section or emitter shell 304a, which is pivotably connected with a lower section or detector shell 306a. The emitter shell 304a can be biased with the detector shell 306a to close together around a pivot point 303a and thereby sandwich finger tissue between the emitter and detector shells 304a, 306a.

In an embodiment, the pivot point 303a advantageously includes a pivot capable of adjusting the relationship between the emitter and detector shells 304a, 306a to effectively level the sections when applied to a tissue site. In another embodiment, the sensor 301a includes some or all features of the finger clip described in U.S. Publication No. 2006/0211924, incorporated above, such as a spring that causes finger clip forces to be distributed along the finger. Paragraphs [0096] through [0105], which describe this feature, are hereby specifically incorporated by reference.

The emitter shell 304a can position and house various emitter components of the sensor 301a. It can be constructed of reflective material (e.g., white silicone or plastic) and/or can be metallic or include metalicized plastic (e.g., including carbon and aluminum) to possibly serve as a heat sink. The emitter shell 304a can also include absorbing opaque material, such as, for example, black or grey colored material, at various areas, such as on one or more flaps 307a, to reduce ambient light entering the sensor 301a.

The detector shell 306a can position and house one or more detector portions of the sensor 301a. The detector shell 306a can be constructed of reflective material, such as white silicone or plastic. As noted, such materials can increase the usable signal at a detector by forcing light back into the tissue and measurement site (see FIG. 1). The detector shell 306a can also include absorbing opaque material at various areas, such as lower area 308a, to reduce ambient light entering the sensor 301a.

Referring to FIGS. 3B and 3C, an example of finger bed 310 is shown in the sensor 301b. The finger bed 310 includes a generally curved surface shaped generally to receive tissue, such as a human digit. The finger bed 310 includes one or more ridges or channels 314. Each of the ridges 314 has a generally convex shape that can facilitate increasing traction or gripping of the patient's finger to the finger bed.

Advantageously, the ridges 314 can improve the accuracy of spectroscopic analysis in certain embodiments by reducing noise that can result from a measurement site moving or shaking loose inside of the sensor 301a. The ridges 314 can be made from reflective or opaque materials in some embodiments to further increase SNR. In other implementations, other surface shapes can be used, such as, for example, generally flat, concave, or convex finger beds 310.

Finger bed 310 can also include an embodiment of a tissue thickness adjuster or protrusion 305. The protrusion 305 includes a measurement site contact area 370 (see FIG. 3C) that can contact body tissue of a measurement site. The protrusion 305 can be removed from or integrated with the finger bed 310. Interchangeable, different shaped protrusions 305 can also be provided, which can correspond to different finger shapes, characteristics, opacity, sizes, or the like.

Referring specifically to FIG. 3C, the contact area 370 of the protrusion 305 can include openings or windows 320, 321, 322, and 323. When light from a measurement site passes through the windows 320, 321, 322, and 323, the light can reach one or more photodetectors (see FIG. 3E). In an embodiment, the windows 320, 321, 322, and 323 mirror specific detector placements layouts such that light can impinge through the protrusion 305 onto the photodetectors. Any number of windows 320, 321, 322, and 323 can be employed in the protrusion 305 to allow light to pass from the measurement site to the photodetectors.

The windows 320, 321, 322, and 323 can also include shielding, such as an embedded grid of wiring or a conductive glass coating, to reduce noise from ambient light or other electromagnetic noise. The windows 320, 321, 322, and 323 can be made from materials, such as plastic or glass. In some embodiments, the windows 320, 321, 322, and 323 can be constructed from conductive glass, such as indium tin oxide (ITO) coated glass. Conductive glass can be useful because its shielding is transparent, and thus allows for a larger aperture versus a window with an embedded grid of wiring. In addition, in certain embodiments, the conductive glass does not need openings in its shielding (since it is transparent), which enhances its shielding performance. For example, some embodiments that employ the conductive glass can attain up to an about 40% to about 50% greater signal than non-conductive glass with a shielding grid. In addition, in some embodiments, conductive glass can be useful for shielding noise from a greater variety of directions than non-conductive glass with a shielding grid.

Turning to FIG. 3B, the sensor 301a can also include a shielding 315a, such as a metal cage, box, metal sheet, perforated metal sheet, a metal layer on a non-metal material, or the like. The shielding 315a is provided in the depicted embodiment below or embedded within the protrusion 305 to reduce noise. The shielding 315a can be constructed from a conductive material, such as copper. The shielding 315a can include one or more openings or windows (not shown). The windows can be made from glass or plastic to thereby allow light that has passed through the windows 320, 321, 322, and 323 on an external surface of the protrusion 305 (see FIG. 3C) to pass through to one or more photodetectors that can be enclosed or provided below (see FIG. 3E).

In some embodiments, the shielding cage for shielding 315a can be constructed in a single manufactured component with or without the use of conductive glass. This form of construction may be useful in order to reduce costs of manufacture as well as assist in quality control of the components. Furthermore, the shielding cage can also be used to house various other components, such as sigma delta components for various embodiments of front end interfaces 108.

Figure 3D:
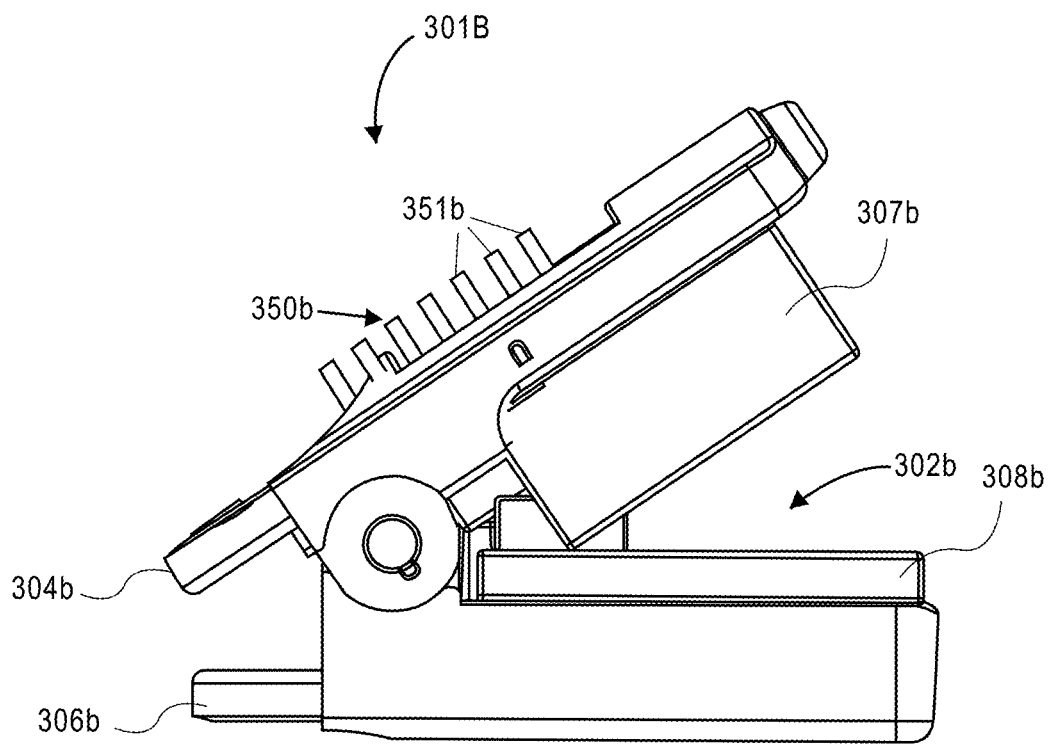
FIG. 3D illustrates a side view of another example noninvasive sensor housing including a heat sink, according to an embodiment of the disclosure.
Figure 3E:
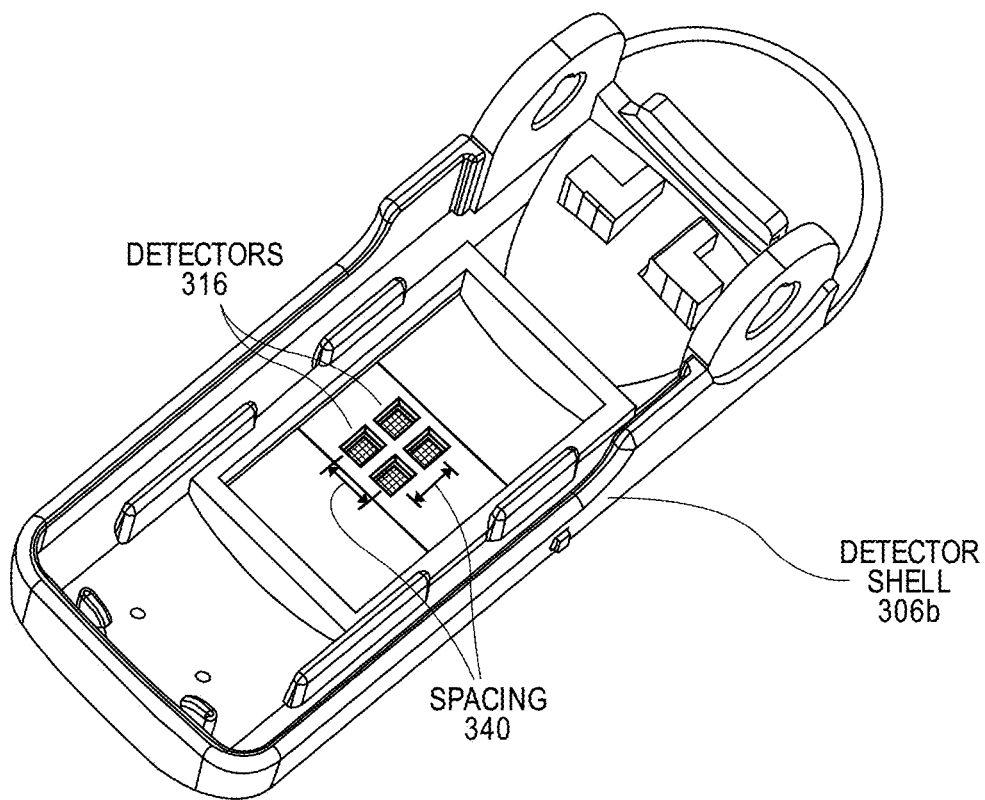
FIG. 3E illustrates a perspective view of an example noninvasive sensor detector shell including example detectors, according to an embodiment of the disclosure.

In an embodiment, the photodetectors can be positioned within or directly beneath the protrusion 305 (see FIG. 3E). In such cases, the mean optical path length from the emitters to the detectors can be reduced and the accuracy of blood analyte measurement can increase. For example, in one embodiment, a convex bump of about 1 mm to about 3 mm in height and about 10 mm$^2$ to about 60 mm$^2$ was found to help signal strength by about an order of magnitude versus other shapes. Of course other dimensions and sizes can be employed in other embodiments. Depending on the properties desired, the length, width, and height of the protrusion 305 can be selected. In making such determinations, consideration can be made of protrusion's 305 effect on blood flow at the measurement site and mean path length for optical radiation passing through openings 320, 321, 322, and 323. Patient comfort can also be considered in determining the size and shape of the protrusion.

In an embodiment, the protrusion 305 can include a pliant material, including soft plastic or rubber, which can somewhat conform to the shape of a measurement site. Pliant materials can improve patient comfort and tactility by conforming the measurement site contact area 370 to the measurement site. Additionally, pliant materials can minimize or reduce noise, such as ambient light. Alternatively, the protrusion 305 can be made from a rigid material, such as hard plastic or metal.

Rigid materials can improve measurement accuracy of a blood analyte by conforming the measurement site to the contact area 370. The contact area 370 can be an ideal shape for improving accuracy or reducing noise. Selecting a material for the protrusion 305 can include consideration of materials that do not significantly alter blood flow at the measurement site. The protrusion 305 and the contact area 370 can include a combination of materials with various characteristics.

The contact area 370 serves as a contact surface for the measurement site. For example, in some embodiments, the contact area 370 can be shaped for contact with a patient's finger. Accordingly, the contact area 370 can be sized and shaped for different sizes of fingers. The contact area 370 can be constructed of different materials for reflective purposes as well as for the comfort of the patient. For example, the contact area 370 can be constructed from materials having various hardness and textures, such as plastic, gel, foam, and the like.

Figure 5:
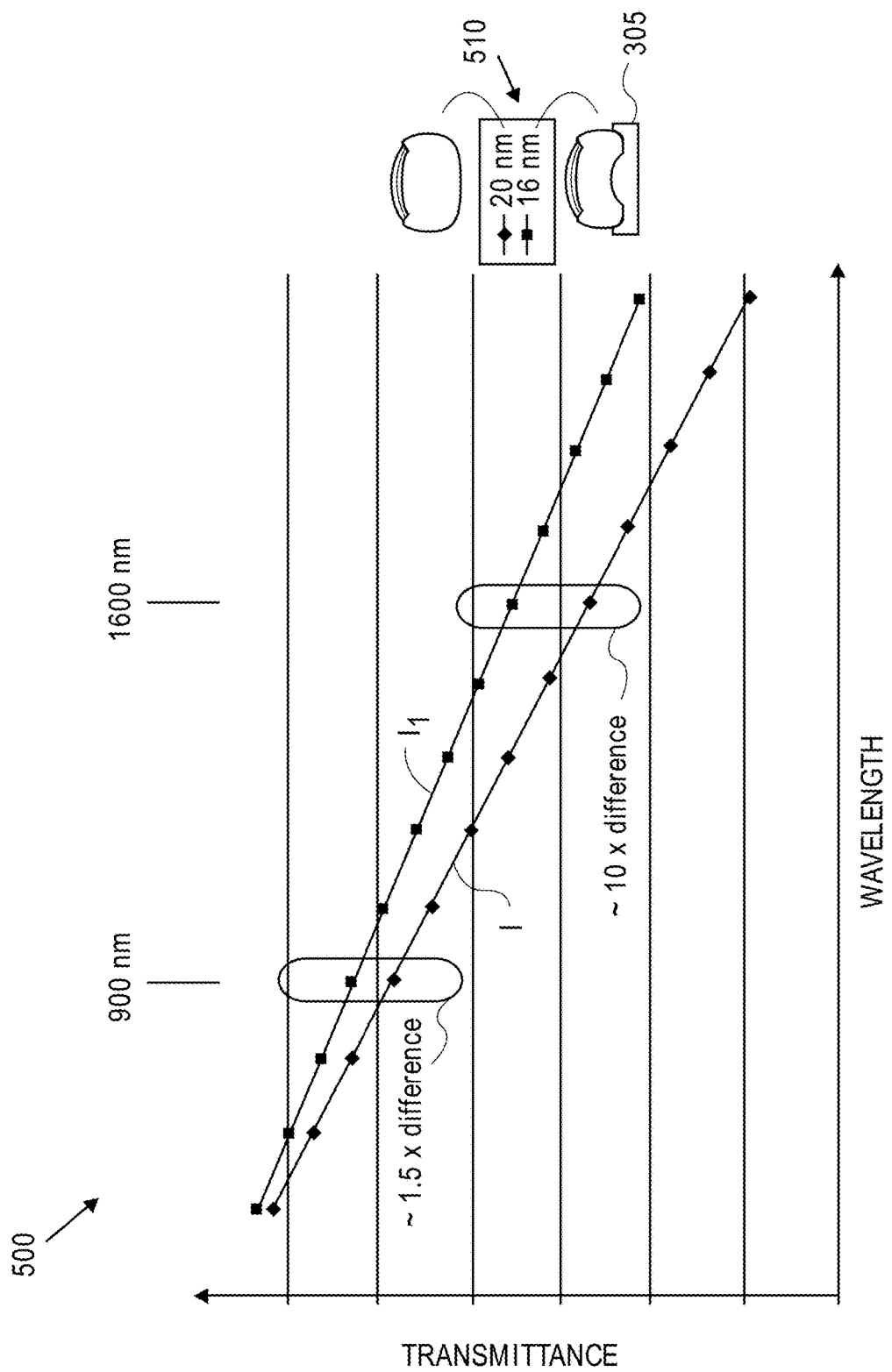
FIG. 5 illustrates an example graph depicting possible effects of a protrusion on light transmittance, according to an embodiment of the disclosure.

The formulas and analysis that follow with respect to FIG. 5 provide insight into how selecting these variables can alter transmittance and intensity gain of optical radiation that has been applied to the measurement site. These examples do not limit the scope of this disclosure.

Referring to FIG. 5, a plot 500 is shown that illustrates examples of effects of embodiments of the protrusion 305 on the SNR at various wavelengths of light. As described above, the protrusion 305 can assist in conforming the tissue and effectively reduce its mean path length. In some instances, this effect by the protrusion 305 can have significant impact on increasing the SNR.

According to the Beer Lambert law, a transmittance of light (I) can be expressed as follows: $I = I_o * e^{-m*b*c}$, where $I_o$ is the initial power of light being transmitted, m is the path length traveled by the light, and the component "b*c" corresponds to the bulk absorption of the light at a specific wavelength of light. For light at about 1600 nm to about 1700 nm, for example, the bulk absorption component is generally around 0.7 mm$^{-1}$. Assuming a typical finger thickness of about 12 mm and a mean path length of 20 mm due to tissue scattering, then $I=I_o*e^{(-20*0.7)}$.

In an embodiment where the protrusion 305 is a convex bump, the thickness of the finger can be reduced to 10 mm (from 12 mm) for some fingers and the effective light mean path is reduced to about 16.6 mm from 20 mm (see box 510). This results in a new transmittance, $I_1=I_o*e^{(-16.6*0.7)}$. A curve for a typical finger (having a mean path length of 20 mm) across various wavelengths is shown in the plot 500 of FIG. 5. The plot 500 illustrates potential effects of the protrusion 305 on the transmittance. As illustrated, comparing I and $I_1$ results in an intensity gain of $e^{(-16.6*0.7)}/e^{(-20*0.7)}$, which is about a 10 times increase for light in the about 1600 nm to about 1700 nm range. Such an increase can affect the SNR at which the sensor can operate. The foregoing gains can be due at least in part to the about 1600 nm to about 1700 nm range having high values in bulk absorptions (water, protein, and the like), e.g., about 0.7 mm$^{-1}$. The plot 500 also shows improvements in the visible/near-infrared range (about 600 nm to about 1300 nm).

Turning again to FIGS. 3A through 3C, an example heat sink 350a is also shown. The heat sink 350a can be attached to, or protrude from an outer surface of, the sensor 301a, thereby providing increased ability for various sensor components to dissipate excess heat. By being on the outer surface of the sensor 301a in certain embodiments, the heat sink 350a can be exposed to the air and thereby facilitate more efficient cooling. In an embodiment, one or more of the emitters (see FIG. 1) generate sufficient heat that inclusion of the heat sink 350a can advantageously allows the sensor 301a to remain safely cooled. The heat sink 350a can include one or more materials that help dissipate heat, such as, for example, aluminum, steel, copper, carbon, combinations of the same, or the like. For example, in some embodiments, the emitter shell 304a can include a heat conducting material that is also readily and relatively inexpensively moldable into desired shapes and forms.

In some embodiments, the heat sink 350a includes metalicized plastic. The metalicized plastic can include aluminum and carbon, for example. The material can allow for improved thermal conductivity and diffusivity, which can increase commercial viability of the heat sink. In some embodiments, the material selected to construct the heat sink 350a can include a thermally conductive liquid crystalline polymer, such as CoolPoly® D5506, commercially available from Cool Polymers®, Inc. of Warwick, R.I. Such a material can be selected for its electrically non-conductive and dielectric properties so as, for example, to aid in electrical shielding. In an embodiment, the heat sink 350a provides improved heat transfer properties when the sensor 301a is active for short intervals of less than a full day's use. In an embodiment, the heat sink 350a can advantageously provide improved heat transfers in about three (3) to about four (4) minute intervals, for example, although a heat sink 350a can be selected that performs effectively in shorter or longer intervals.

Moreover, the heat sink 350a can have different shapes and configurations for aesthetic as well as for functional purposes. In an embodiment, the heat sink is configured to maximize heat dissipation, for example, by maximizing surface area. In an embodiment, the heat sink 350a is molded into a generally curved surface and includes one or more fins, undulations, grooves, or channels. The example heat sink 350a shown includes fins 351a (see FIG. 3A).

An alternative shape of a sensor 301b and heat sink 350b is shown in FIG. 3D. The sensor 301b can include some or all of the features of the sensor 301a. For example, the sensor 301b includes an enclosure 302b formed by an emitter shell 304b and a detector shell 306b, pivotably connected about a pivot 303a. The emitter shell 304b can also include absorbing opaque material on one or more flaps 307b, and the detector shell 306a can also include absorbing opaque material at various areas, such as lower area 308b.

However, the shape of the sensor 301b is different in this embodiment. In particular, the heat sink 350b includes comb protrusions 351b. The comb protrusions 351b are exposed to the air in a similar manner to the fins 351a of the heat sink 350a, thereby facilitating efficient cooling of the sensor 301b.

FIG. 3E illustrates a more detailed example of a detector shell 306b of the sensor 301b. The features described with respect to the detector shell 306b can also be used with the detector shell 306a of the sensor 301a.

As shown, the detector shell 306b includes detectors 316. The detectors 316 can have a predetermined spacing 340 from each other, or a spatial relationship among one another that results in a spatial configuration. This spatial configuration can purposefully create a variation of path lengths among detectors 316 and the emitter discussed above.

In the depicted embodiment, the detector shell 316 can hold multiple (e.g., two, three, four, etc.) photodiode arrays that are arranged in a two-dimensional grid pattern. Multiple photodiode arrays can also be useful to detect light piping (e.g., light that bypasses measurement site 102). In the detector shell 316, walls can be provided to separate the individual photodiode arrays to prevent or reduce mixing of light signals from distinct quadrants. In addition, the detector shell 316 can be covered by windows of transparent material, such as glass, plastic, or the like, to allow maximum or increased transmission of power light captured. In various embodiments, the transparent materials used can also be partially transparent or translucent or can otherwise pass some or all of the optical radiation passing through them. As noted, this window can include some shielding in the form of an embedded grid of wiring, or a conductive layer or coating.

As further illustrated by FIG. 3E, the detectors 316 can have a spatial configuration of a grid. However, the detectors 316 can be arranged in other configurations that vary the path length. For example, the detectors 316 can be arranged in a linear array, a logarithmic array, a two-dimensional array, a zig-zag pattern, or the like. Furthermore, any number of the detectors 316 can be employed in certain embodiments.

Figure 3F:
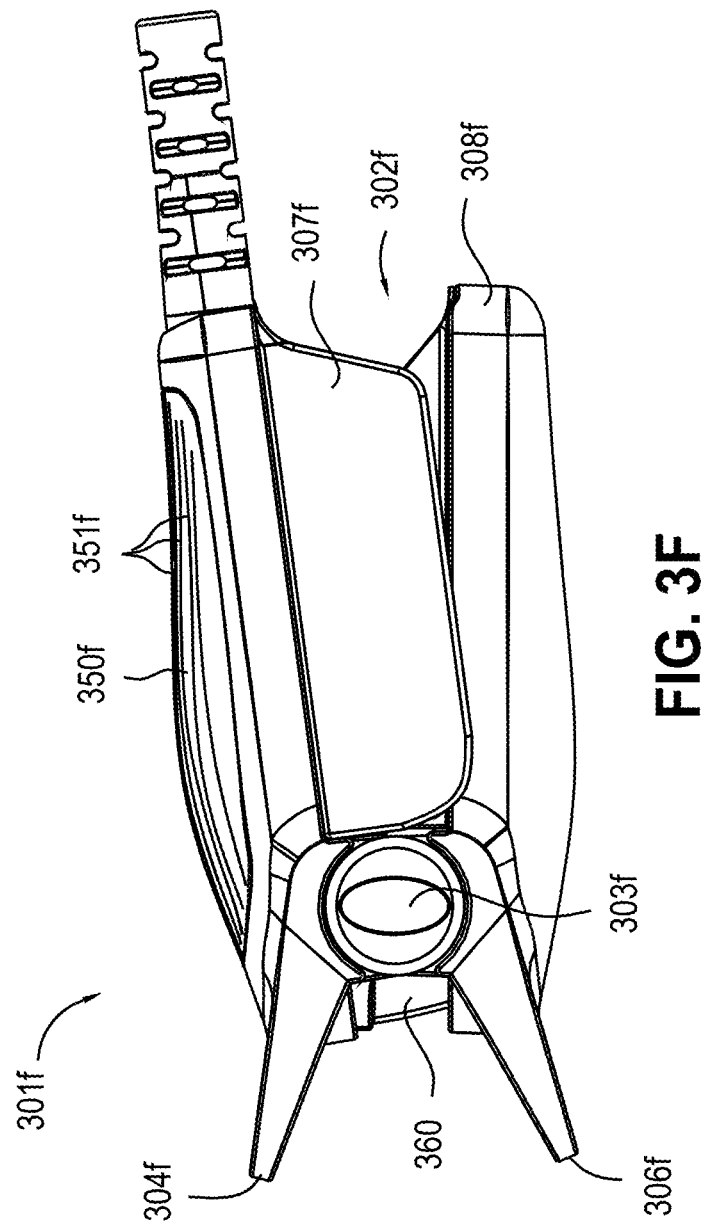
FIG. 3F illustrates a side view of an example noninvasive sensor housing including a finger bed protrusion and heat sink, according to an embodiment of the disclosure.

FIG. 3F illustrates another embodiment of a sensor 301f. The sensor 301f can include some or all of the features of the sensor 301a of FIG. 3A described above. For example, the sensor 301f includes an enclosure 302f formed by an upper section or emitter shell 304f, which is pivotably connected with a lower section or detector shell 306f around a pivot point 303f. The emitter shell 304f can also include absorbing opaque material on various areas, such as on one or more flaps 307f, to reduce ambient light entering the sensor 301f. The detector shell 306f can also include absorbing opaque material at various areas, such as a lower area 308f. The sensor 301f also includes a heat sink 350f, which includes fins 351f.

In addition to these features, the sensor 301f includes a flex circuit cover 360, which can be made of plastic or another suitable material. The flex circuit cover 360 can cover and thereby protect a flex circuit (not shown) that extends from the emitter shell 304f to the detector shell 306f. An example of such a flex circuit is illustrated in U.S.

Publication No. 2006/0211924, incorporated above (see FIG. 46 and associated description, which is hereby specifically incorporated by reference). The flex circuit cover 360 is shown in more detail below in FIG. 17.

Figure 4A:
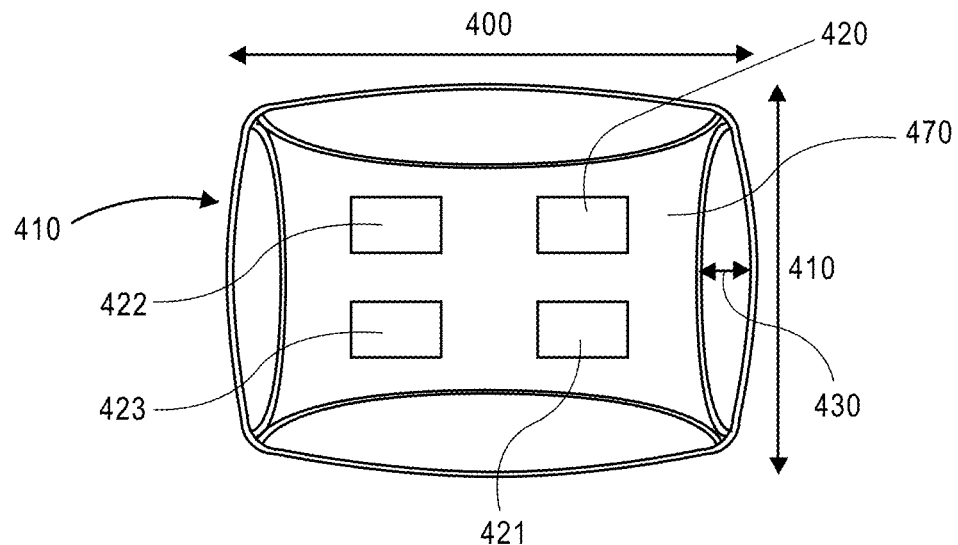
FIGS. 4A through 4C illustrate top elevation, side and top perspective views of an example protrusion, according to an embodiment of the disclosure.
Figure 4B:
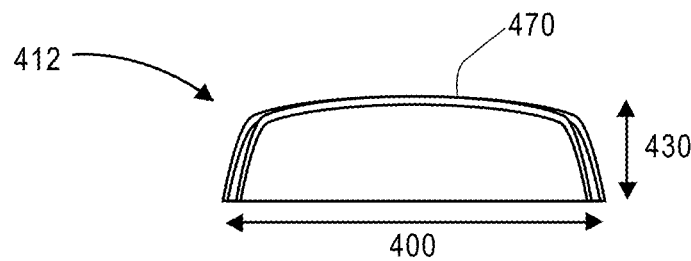
Figure 4C:
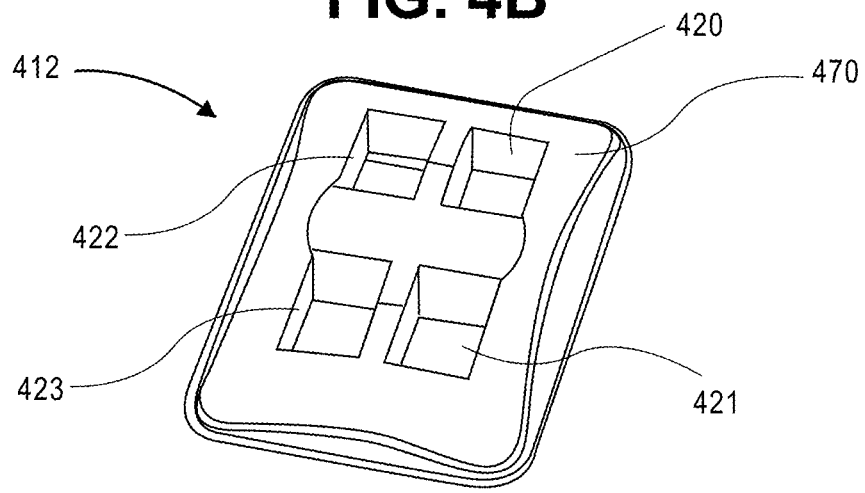

In addition, sensors 301a-f has extra length—extends to second joint on finger—Easier to place, harder to move due to cable, better for light piping FIGS. 4A through 4C illustrate example arrangements of a protrusion 405, which is an embodiment of the protrusion 305 described above. In an embodiment, the protrusion 405 can include a measurement site contact area 470. The measurement site contact area 470 can include a surface that molds body tissue of a measurement site, such as a finger, into a flat or relatively flat surface.

The protrusion 405 can have dimensions that are suitable for a measurement site such as a patient's finger. As shown, the protrusion 405 can have a length 400, a width 410, and a height 430. The length 400 can be from about 9 to about 11 millimeters, e.g., about 10 millimeters. The width 410 can be from about 7 to about 9 millimeters, e.g., about 8 millimeters. The height 430 can be from about 0.5 millimeters to about 3 millimeters, e.g., about 2 millimeters. In an embodiment, the dimensions 400, 410, and 430 can be selected such that the measurement site contact area 470 includes an area of about 80 square millimeters, although larger and smaller areas can be used for different sized tissue for an adult, an adolescent, or infant, or for other considerations.

The measurement site contact area 470 can also include differently shaped surfaces that conform the measurement site into different shapes. For example, the measurement site contact area 470 can be generally curved and/or convex with respect to the measurement site. The measurement site contact area 470 can be other shapes that reduce or even minimize air between the protrusion 405 and or the measurement site. Additionally, the surface pattern of the measurement site contact area 470 can vary from smooth to bumpy, e.g., to provide varying levels of grip.

In FIGS. 4A and 4C, openings or windows 420, 421, 422, and 423 can include a wide variety of shapes and sizes, including for example, generally square, circular, triangular, or combinations thereof. The windows 420, 421, 422, and 423 can be of non-uniform shapes and sizes. As shown, the windows 420, 421, 422, and 423 can be evenly spaced out in a grid like arrangement. Other arrangements or patterns of arranging the windows 420, 421, 422, and 423 are possible. For example, the windows 420, 421, 422, and 423 can be placed in a triangular, circular, or linear arrangement. In some embodiments, the windows 420, 421, 422, and 423 can be placed at different heights with respect to the finger bed 310 of FIG. 3. The windows 420, 421, 422, and 423 can also mimic or approximately mimic a configuration of, or even house, a plurality of detectors.

FIGS. 6A through 6D illustrate another embodiment of a protrusion 605 that can be used as the tissue shaper 105 described above or in place of the protrusions 305, 405 described above. The depicted protrusion 605 is a partially cylindrical lens having a partial cylinder 608 and an extension 610. The partial cylinder 608 can be a half cylinder in some embodiments; however, a smaller or greater portion than half of a cylinder can be used. Advantageously, in certain embodiments, the partially cylindrical protrusion 605 focuses light onto a smaller area, such that fewer detectors can be used to detect the light attenuated by a measurement site.

Figure 6A:
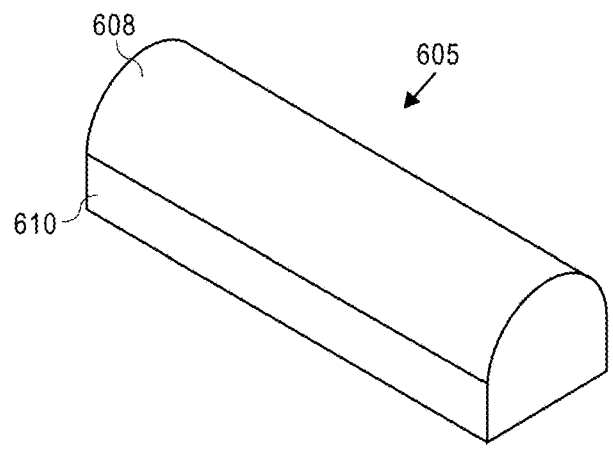
FIGS. 6A through 6D illustrate perspective, front elevation, side and top views of another example protrusion, according to an embodiment of the disclosure.
Figure 6B:
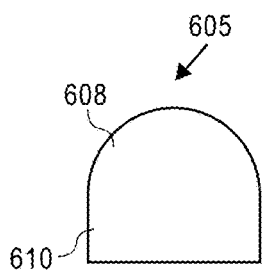
Figure 6C:
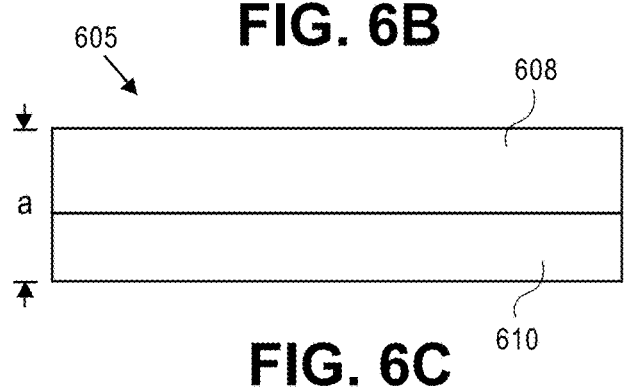
Figure 6D:
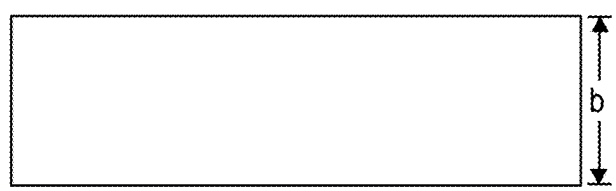

FIG. 6A illustrates a perspective view of the partially cylindrical protrusion 605. FIG. 6B illustrates a front elevation view of the partially cylindrical protrusion 605. FIG. 6C illustrates a side view of the partially cylindrical protrusion 605. FIG. 6D illustrates a top view of the partially cylindrical protrusion 605.

Advantageously, in certain embodiments, placing the partially cylindrical protrusion 605 over the photodiodes in any of the sensors described above adds multiple benefits to any of the sensors described above. In one embodiment, the partially cylindrical protrusion 605 penetrates into the tissue and reduces the path length of the light traveling in the tissue, similar to the protrusions described above.

The partially cylindrical protrusion 605 can also collect light from a large surface and focus down the light to a smaller area. As a result, in certain embodiments, signal strength per area of the photodiode can be increased. The partially cylindrical protrusion 605 can therefore facilitate a lower cost sensor because, in certain embodiments, less photodiode area can be used to obtain the same signal strength. Less photodiode area can be realized by using smaller photodiodes or fewer photodiodes (see, e.g., FIG. 14). If fewer or smaller photodiodes are used, the partially cylindrical protrusion 605 can also facilitate an improved SNR of the sensor because fewer or smaller photodiodes can have less dark current.

The dimensions of the partially cylindrical protrusion 605 can vary based on, for instance, a number of photodiodes used with the sensor. Referring to FIG. 6C, the overall height of the partially cylindrical protrusion 605 (measurement "a") in some implementations is about 1 to about 3 mm. A height in this range can allow the partially cylindrical protrusion 605 to penetrate into the pad of the finger or other tissue and reduce the distance that light travels through the tissue. Other heights, however, of the partially cylindrical protrusion 605 can also accomplish this objective. For example, the chosen height of the partially cylindrical protrusion 605 can be selected based on the size of the measurement site, whether the patient is an adult or child, and so on. In an embodiment, the height of the protrusion 605 is chosen to provide as much tissue thickness reduction as possible while reducing or preventing occlusion of blood vessels in the tissue.

Referring to FIG. 6D, the width of the partially cylindrical protrusion 605 (measurement "b") can be about 3 to about 5 mm. In one embodiment, the width is about 4 mm. In one embodiment, a width in this range provides good penetration of the partially cylindrical protrusion 605 into the tissue to reduce the path length of the light. Other widths, however, of the partially cylindrical protrusion 605 can also accomplish this objective. For example, the width of the partially cylindrical protrusion 605 can vary based on the size of the measurement site, whether the patient is an adult or child, and so on. In addition, the length of the protrusion 605 could be about 10 mm, or about 8 mm to about 12 mm, or smaller than 8 mm or greater than 12 mm.

In certain embodiments, the focal length (f) for the partially cylindrical protrusion 605 can be expressed as:

$$f = \frac{R}{n-1},$$

where R is the radius of curvature of the partial cylinder 608 and n is the index of refraction of the material used. In certain embodiments, the radius of curvature can be between about 1.5 mm and about 2 mm. In another embodiment, the partially cylindrical protrusion 605 can include a material, such as nBK7 glass, with an index of refraction of around 1.5 at 1300 nm, which can provide focal lengths of between about 3 mm and about 4 mm.

A partially cylindrical protrusion 605 having a material with a higher index of refraction such as nSF11 glass (e.g., n=1.75 at 1300 nm) can provide a shorter focal length and possibly a smaller photodiode chip, but can also cause higher reflections due to the index of refraction mismatch with air. Many types of glass or plastic can be used with index of refraction values ranging from, for example, about 1.4 to about 1.9. The index of refraction of the material of the protrusion 605 can be chosen to improve or optimize the light focusing properties of the protrusion 605. A plastic partially cylindrical protrusion 605 could provide the cheapest option in high volumes but can also have some undesired light absorption peaks at wavelengths higher than 1500 nm. Other focal lengths and materials having different indices of refraction can be used for the partially cylindrical protrusion 605.

Placing a photodiode at a given distance below the partially cylindrical protrusion 605 can facilitate capturing some or all of the light traveling perpendicular to the lens within the active area of the photodiode (see FIG. 14). Different sizes of the partially cylindrical protrusion 605 can use different sizes of photodiodes. The extension 610 added onto the bottom of the partial cylinder 608 is used in certain embodiments to increase the height of the partially cylindrical protrusion 605. In an embodiment, the added height is such that the photodiodes are at or are approximately at the focal length of the partially cylindrical protrusion 605. In an embodiment, the added height provides for greater thinning of the measurement site. In an embodiment, the added height assists in deflecting light piped through the sensor. This is because light piped around the sensor passes through the side walls of the added height without being directed toward the detectors. The extension 610 can also further facilitate the protrusion 605 increasing or maximizing the amount of light that is provided to the detectors. In some embodiments, the extension 610 can be omitted.

Figure 6E:
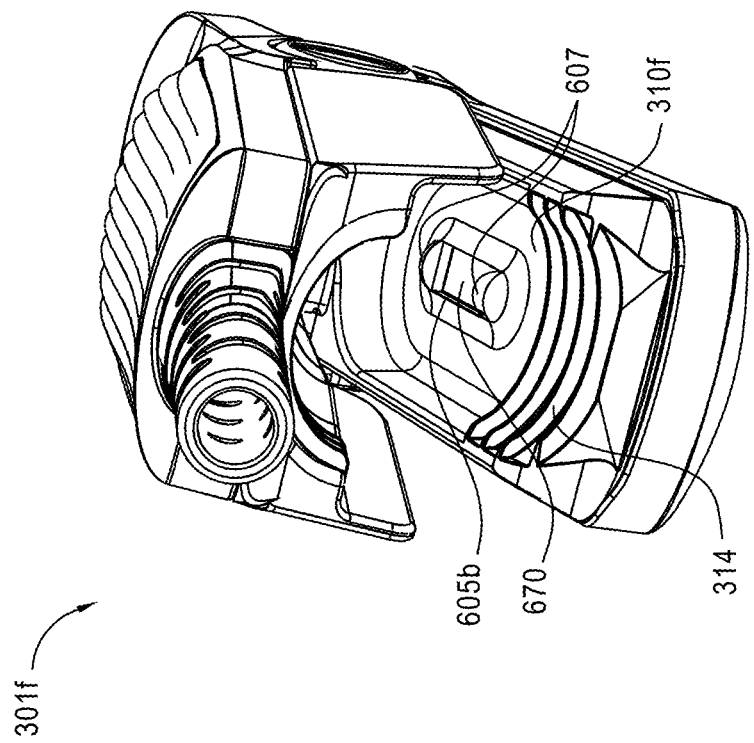
FIG. 6E illustrates an example sensor incorporating the protrusion of FIGS. 6A through 6D, according to an embodiment of the disclosure.

FIG. 6E illustrates another view of the sensor 301f of FIG. 3F, which includes an embodiment of a partially cylindrical protrusion 605b. Like the sensor 301A shown in FIGS. 3B and 3C, the sensor 301f includes a finger bed 310f. The finger bed 310f includes a generally curved surface shaped generally to receive tissue, such as a human digit. The finger bed 310f also includes the ridges or channels 314 described above with respect to FIGS. 3B and 3C.

The example of finger bed 310f shown also includes the protrusion 605b, which includes the features of the protrusion 605 described above. In addition, the protrusion 605b also includes chamfered edges 607 on each end to provide a more comfortable surface for a finger to slide across (see also FIG. 14D). In another embodiment, the protrusion 605b could instead include a single chamfered edge 607 proximal to the ridges 314. In another embodiment, one or both of the chamfered edges 607 could be rounded.

The protrusion 605b also includes a measurement site contact area 670 that can contact body tissue of a measurement site. The protrusion 605b can be removed from or integrated with the finger bed 310f. Interchangeable, differently shaped protrusions 605b can also be provided, which can correspond to different finger shapes, characteristics, opacity, sizes, or the like.

Figure 7A:
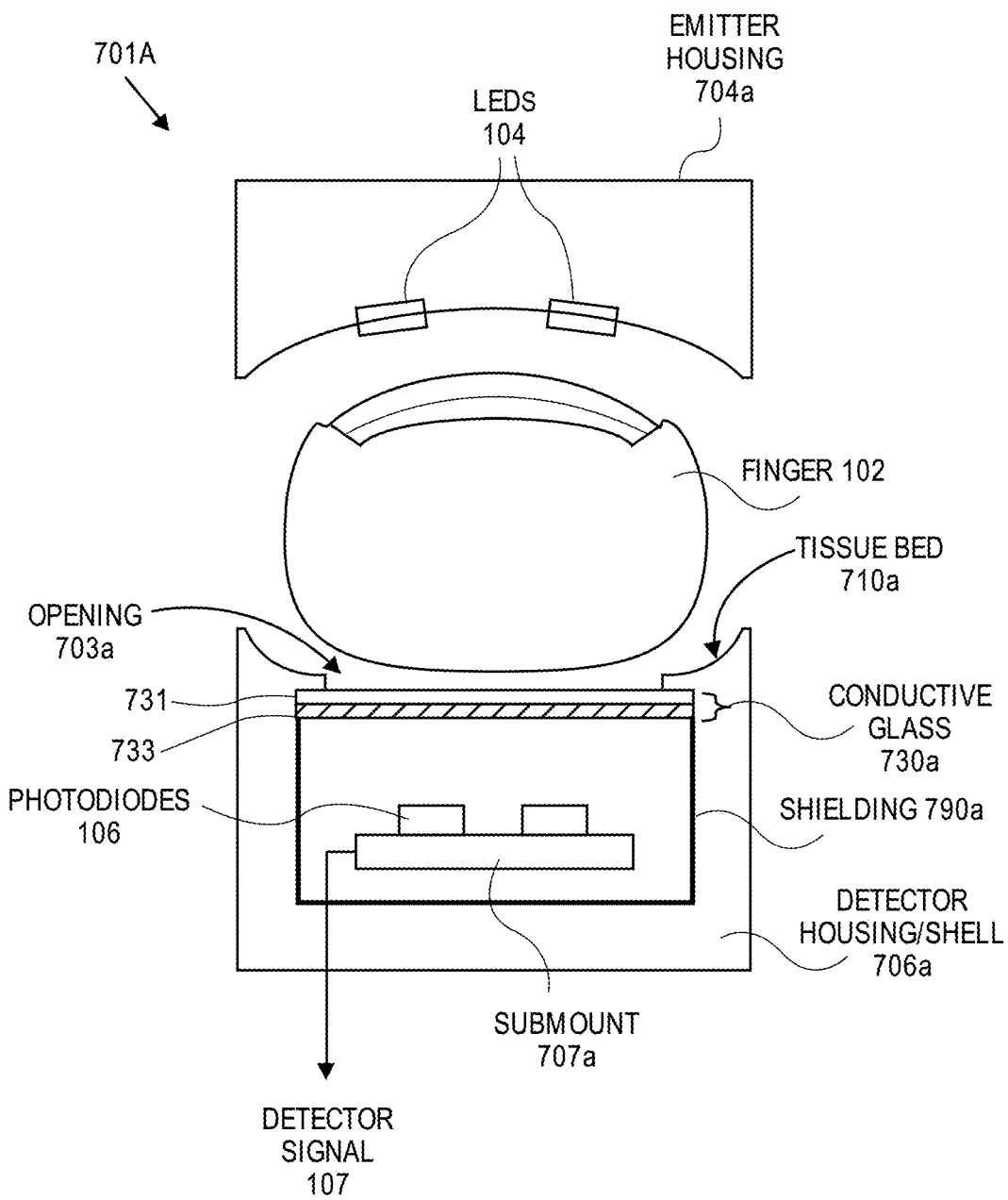
FIGS. 7A through 7B illustrate example arrangements of conductive glass that may be employed in the system of FIG. 1, according to embodiments of the disclosure.
Figure 7B:
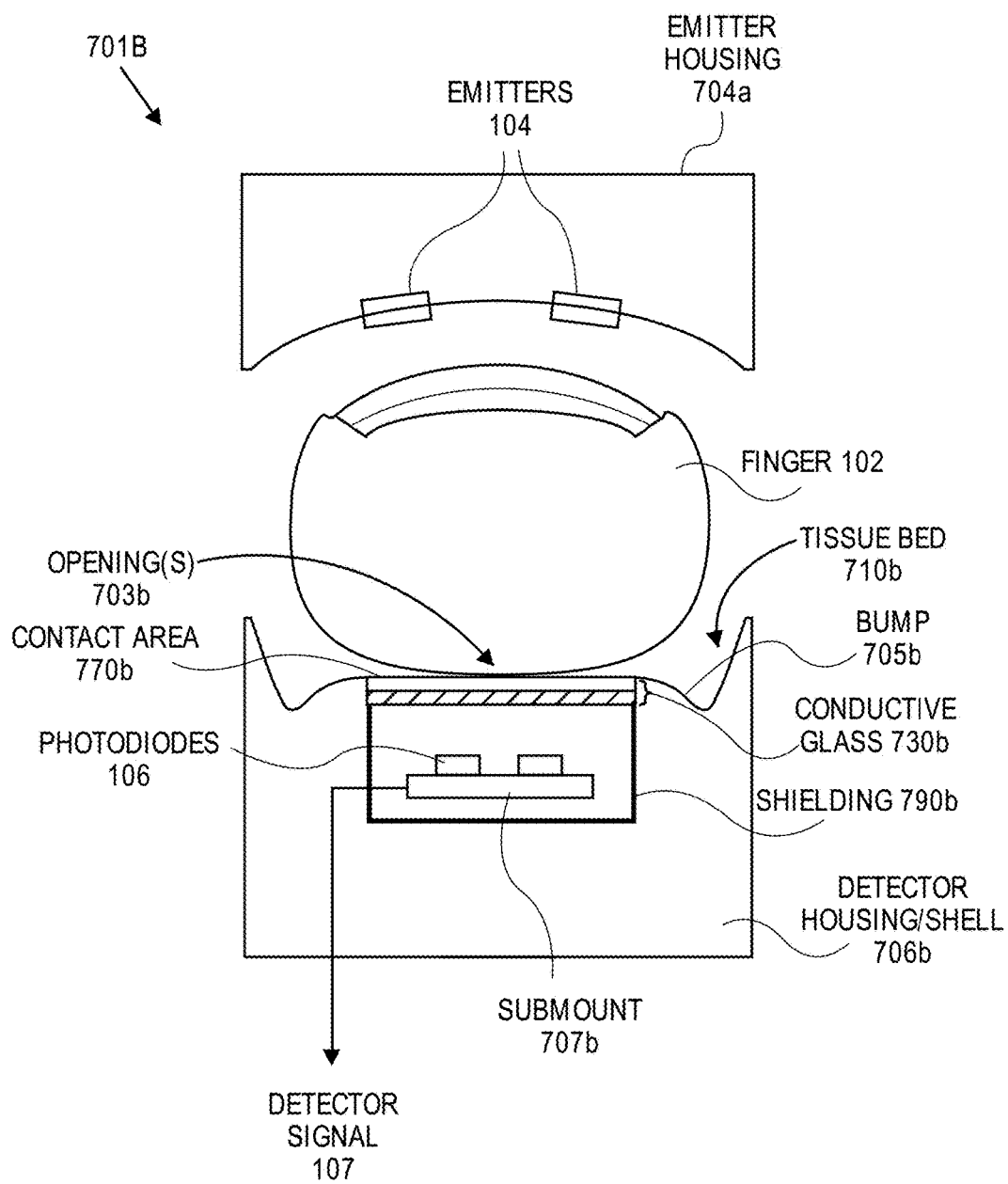

FIGS. 7A and 7B illustrate block diagrams of sensors 701 that include example arrangements of conductive glass or conductive coated glass for shielding. Advantageously, in certain embodiments, the shielding can provide increased SNR. The features of the sensors 701 can be implemented with any of the sensors 101, 201, 301 described above. Although not shown, the partially cylindrical protrusion 605 of FIG. 6 can also be used with the sensors 701 in certain embodiments.

For example, referring specifically to FIG. 7A, the sensor 701a includes an emitter housing 704a and a detector housing 706. The emitter housing 704a includes LEDs 104. The detector housing 706a includes a tissue bed 710a with an opening or window 703a, the conductive glass 730a, and one or more photodiodes for detectors 106 provided on a submount 707a.

During operation, a finger 102 can be placed on the tissue bed 710a and optical radiation can be emitted from the LEDs 104. Light can then be attenuated as it passes through or is reflected from the tissue of the finger 102. The attenuated light can then pass through the opening 703a in the tissue bed 710a. Based on the received light, the detectors 106 can provide a detector signal 107, for example, to the front end interface 108 (see FIG. 1).

In the depicted embodiment, the conductive glass 730 is provided in the opening 703. The conductive glass 730 can thus not only permit light from the finger to pass to the detectors 106, but it can also supplement the shielding of the detectors 106 from noise. The conductive glass 730 can include a stack or set of layers. In FIG. 7A, the conductive glass 730a is shown having a glass layer 731 proximate the finger 102 and a conductive layer 733 electrically coupled to the shielding 790a.

In an embodiment, the conductive glass 730a can be coated with a conductive, transparent or partially transparent material, such as a thin film of indium tin oxide (ITO). To supplement electrical shielding effects of a shielding enclosure 790a, the conductive glass 730a can be electrically coupled to the shielding enclosure 790a. The conductive glass 730a can be electrically coupled to the shielding 704a based on direct contact or via other connection devices, such as a wire or another component.

The shielding enclosure 790a can be provided to encompass the detectors 106 to reduce or prevent noise. For example, the shielding enclosure 790a can be constructed from a conductive material, such as copper, in the form of a metal cage. The shielding or enclosure a can include an opaque material to not only reduce electrical noise, but also ambient optical noise.

In some embodiments, the shielding enclosure 790a can be constructed in a single manufactured component with or without the use of conductive glass. This form of construction may be useful in order to reduce costs of manufacture as well as assist in quality control of the components. Furthermore, the shielding enclosure 790a can also be used to house various other components, such as sigma delta components for various embodiments of front end interfaces 108.

Referring to FIG. 7B, another block diagram of an example sensor 701b is shown. A tissue bed 710b of the sensor 701b includes a protrusion 705b, which is in the form of a convex bump. The protrusion 705b can include all of the features of the protrusions or tissue shaping materials described above. For example, the protrusion 705b includes a contact area 370 that comes in contact with the finger 102 and which can include one or more openings 703b. One or more components of conductive glass 730b can be provided in the openings 703. For example, in an embodiment, each of the openings 703 can include a separate window of the conductive glass 730b. In an embodiment, a single piece of the conductive glass 730b can used for some or all of the openings 703b. The conductive glass 730b is smaller than the conductive glass 730a in this particular embodiment.

A shielding enclosure 790b is also provided, which can have all the features of the shielding enclosure 790a. The shielding enclosure 790b is smaller than the shielding enclosure 790a; however, a variety of sizes can be selected for the shielding enclosures 790.

In some embodiments, the shielding enclosure 790b can be constructed in a single manufactured component with or without the use of conductive glass. This form of construction may be useful in order to reduce costs of manufacture as well as assist in quality control of the components. Furthermore, the shielding enclosure 790b can also be used to house various other components, such as sigma delta components for various embodiments of front end interfaces 108.

FIGS. 8A through 8D illustrate a perspective view, side views, and a bottom elevation view of the conductive glass described above with respect to the sensors 701a, 701b. As shown in the perspective view of FIG. 8A and side view of FIG. 8B, the conductive glass 730 includes the electrically conductive material 733 described above as a coating on the glass layer 731 described above to form a stack. In an embodiment where the electrically conductive material 733 includes indium tin oxide, surface resistivity of the electrically conductive material 733 can range approximately from 30 ohms per square inch to 500 ohms per square inch, or approximately 30, 200, or 500 ohms per square inch. As would be understood by a person of skill in the art from the present disclosure, other resistivities can also be used which are less than 30 ohms or more than 500 ohms. Other transparent, electrically conductive materials can be used as the material 733.

Although the conductive material 733 is shown spread over the surface of the glass layer 731, the conductive material 733 can be patterned or provided on selected portions of the glass layer 731. Furthermore, the conductive material 733 can have uniform or varying thickness depending on a desired transmission of light, a desired shielding effect, and other considerations.

Figure 8A:
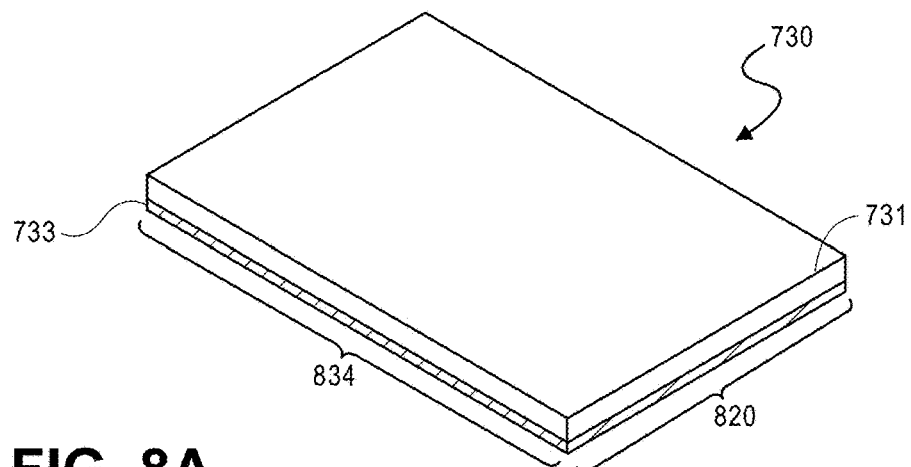
FIGS. 8A through 8D illustrate an example top elevation view, side views, and a bottom elevation view of the conductive glass that may be employed in the system of FIG. 1, according to embodiments of the disclosure.
Figure 8B:
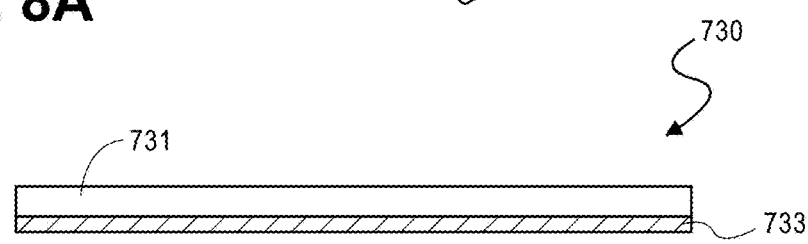
Figure 8C:
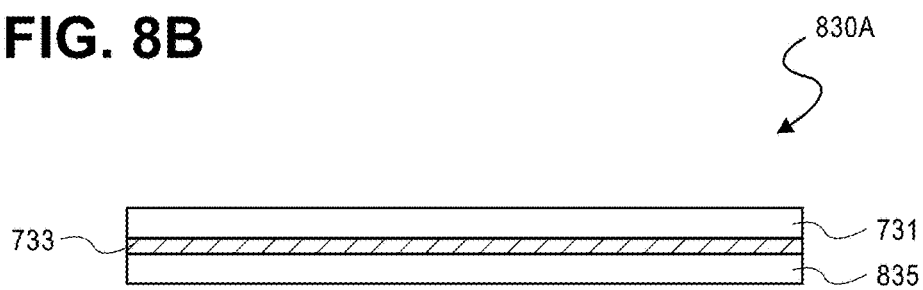

In FIG. 8C, a side view of a conductive glass 830a is shown to illustrate an embodiment where the electrically conductive material 733 is provided as an internal layer between two glass layers 731, 835. Various combinations of integrating electrically conductive material 733 with glass are possible. For example, the electrically conductive material 733 can be a layer within a stack of layers. This stack of layers can include one or more layers of glass 731, 835, as well as one or more layers of conductive material 733. The stack can include other layers of materials to achieve desired characteristics.

Figure 8D:
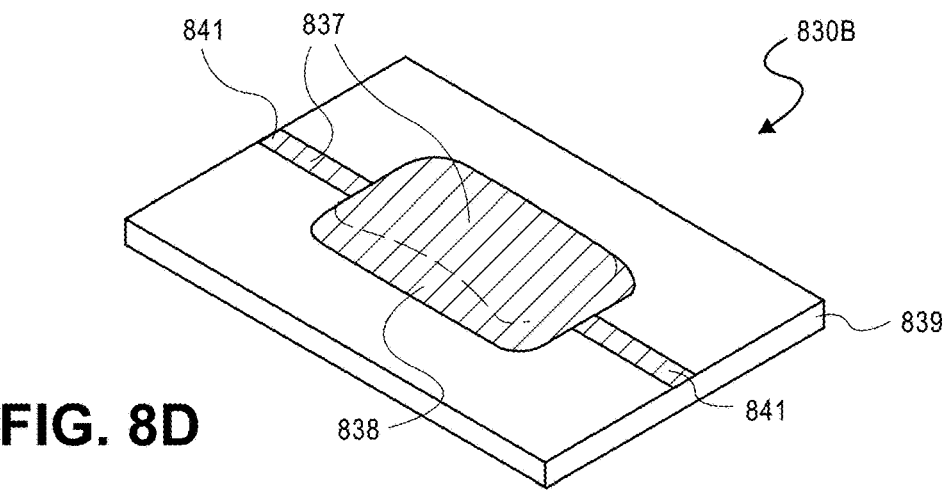

In FIG. 8D, a bottom perspective view is shown to illustrate an embodiment where a conductive glass 830b can include conductive material 837 that occupies or covers a portion of a glass layer 839. This embodiment can be useful, for example, to create individual, shielded windows for detectors 106, such as those shown in FIG. 3C. The conductive material 837 can be patterned to include an area 838 to allow light to pass to detectors 106 and one or more strips 841 to couple to the shielding 704 of FIG. 7.

Other configurations and patterns for the conductive material can be used in certain embodiments, such as, for example, a conductive coating lining periphery edges, a conductive coating outlaid in a pattern including a grid or other pattern, a speckled conductive coating, coating outlaid in lines in either direction or diagonally, varied thicknesses from the center out or from the periphery in, or other suitable patterns or coatings that balance the shielding properties with transparency considerations.

Figure 9:
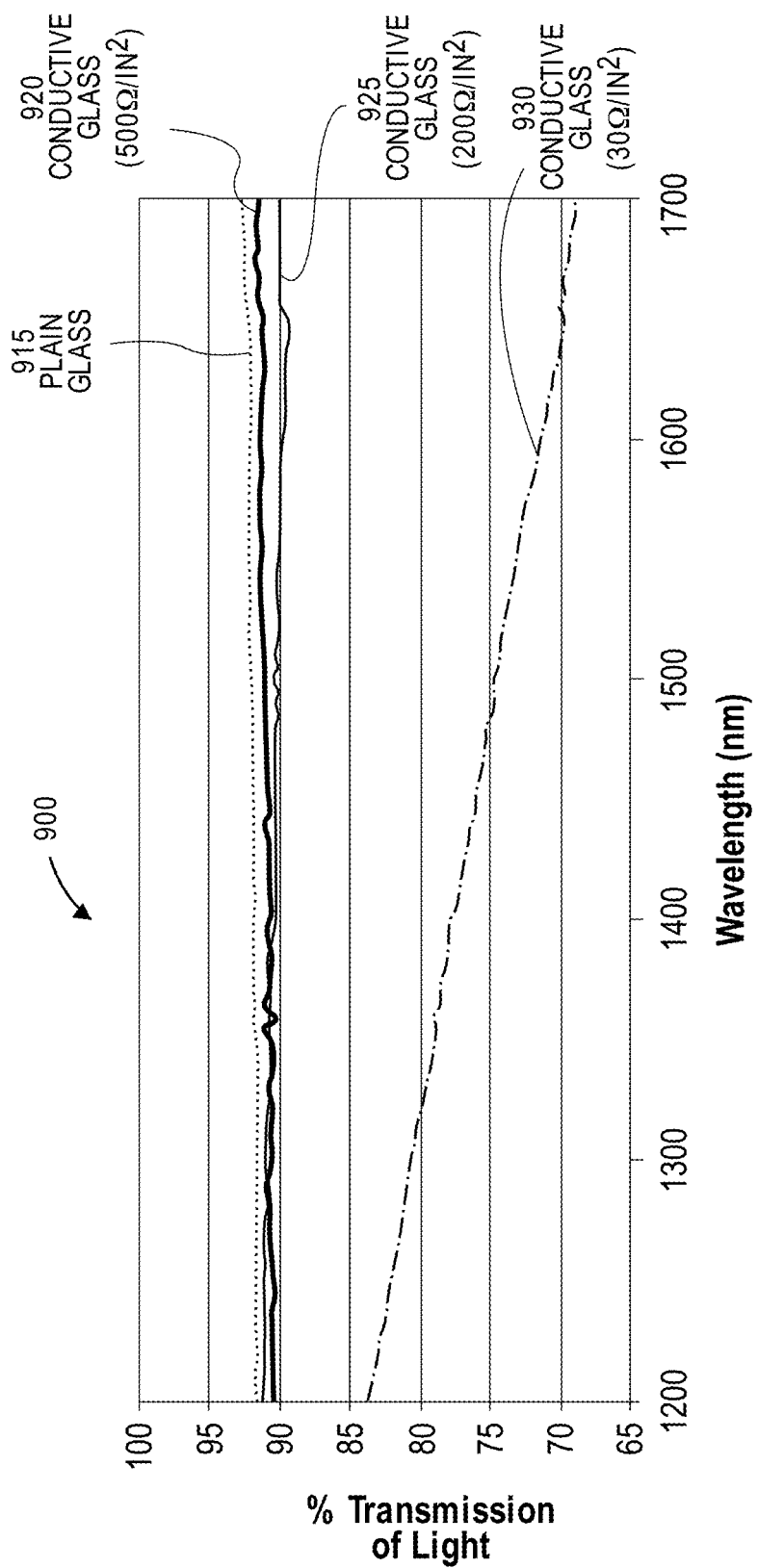
FIG. 9 shows example comparative results obtained by an embodiment of a sensor.

FIG. 9 depicts an example graph 900 that illustrates comparative results obtained by an example sensor having components similar to those disclosed above with respect to FIGS. 7 and 8. The graph 900 depicts the results of the percentage of transmission of varying wavelengths of light for different types of windows used in the sensors described above.

A line 915 on the graph 900 illustrates example light transmission of a window made from plain glass. As shown, the light transmission percentage of varying wavelengths of light is approximately 90% for a window made from plain glass. A line 920 on the graph 900 demonstrates an example light transmission percentage for an embodiment in which a window is made from glass having an ITO coating with a surface resistivity of 500 ohms per square inch. A line 925 on the graph 900 shows an example light transmission for an embodiment in which a window is made from glass that includes a coating of ITO oxide with a surface resistivity of 200 ohms per square inch. A line 930 on the graph 900 shows an example light transmission for an embodiment in which a window is made from glass that includes a coating of ITO oxide with a surface resistivity of 30 ohms per square inch.

The light transmission percentage for a window with currently available embedded wiring can have a light transmission percentage of approximately 70%. This lower percentage of light transmission can be due to the opacity of the wiring employed in a currently available window with wiring. Accordingly, certain embodiments of glass coatings described herein can employ, for example, ITO coatings with different surface resistivity depending on the desired light transmission, wavelengths of light used for measurement, desired shielding effect, and other criteria.

Figure 10A:
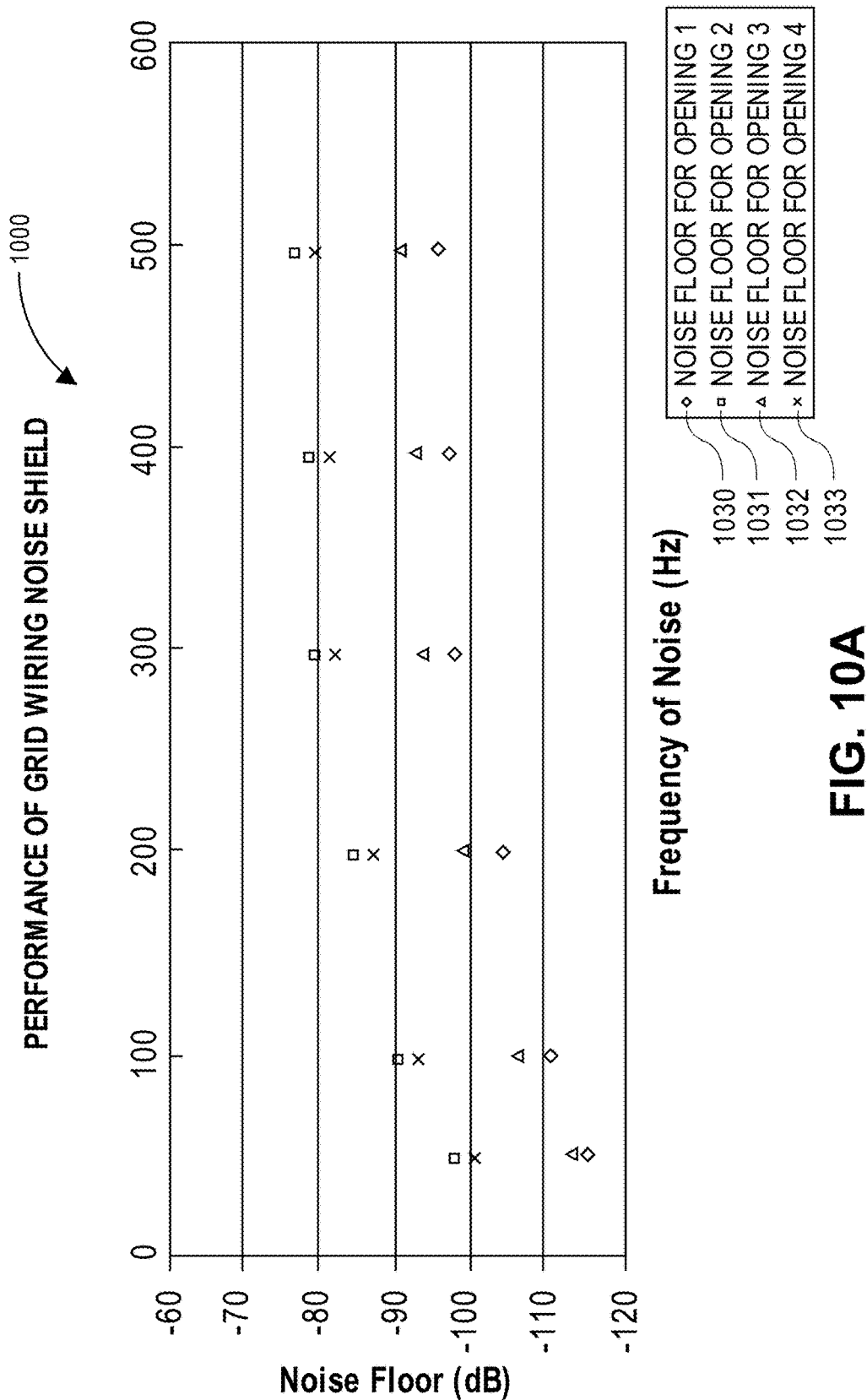
FIGS. 10A and 10B illustrate comparative noise floors of various embodiments of the present disclosure.
Figure 10B:
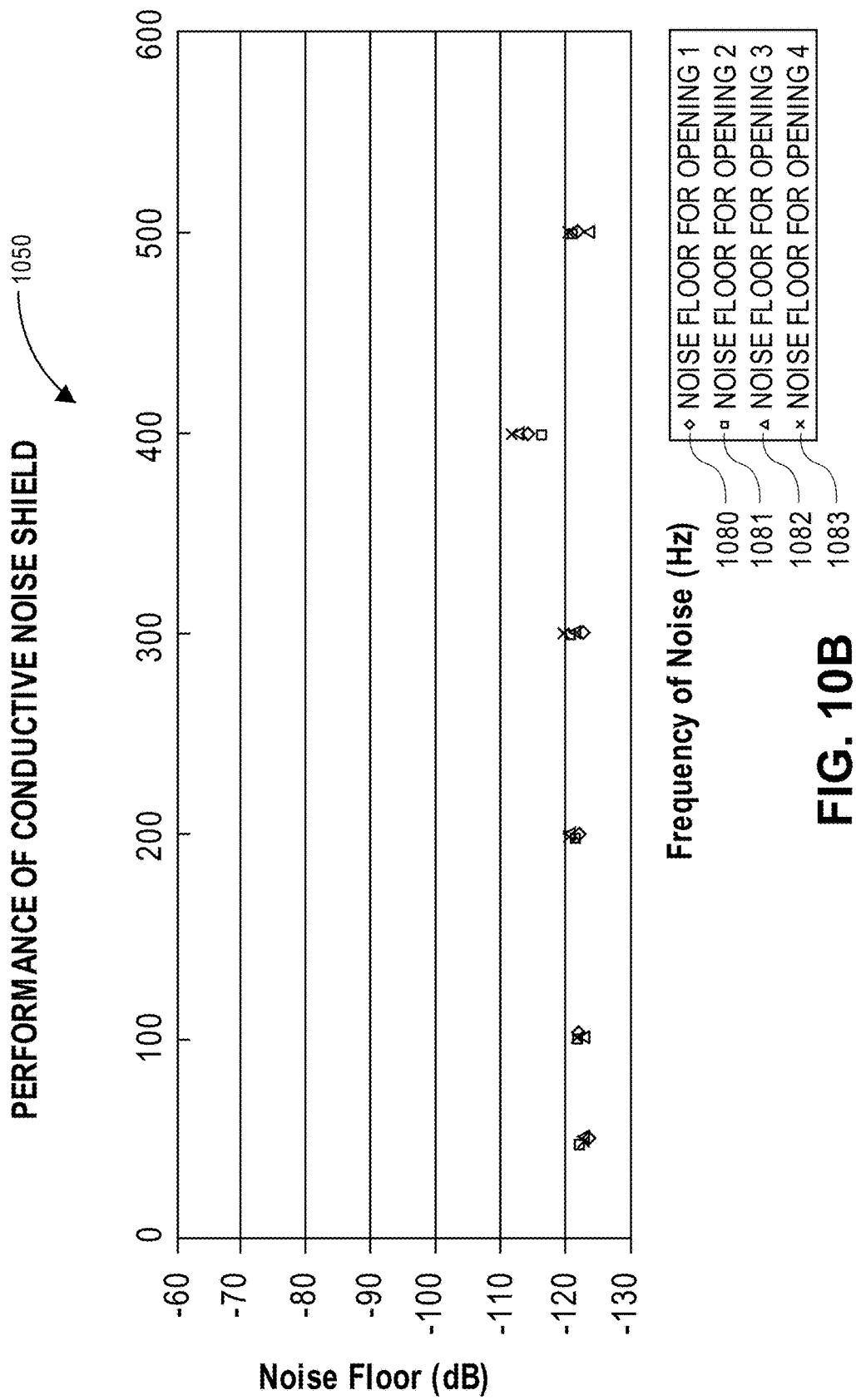

FIGS. 10A through 10B illustrate comparative noise floors of example implementations of the sensors described above. Noise can include optical noise from ambient light and electro-magnetic noise, for example, from surrounding electrical equipment. In FIG. 10A, a graph 1000 depicts possible noise floors for different frequencies of noise for an embodiment in which one of the sensors described above included separate windows for four (4) detectors 106. One or more of the windows included an embedded grid of wiring as a noise shield. Symbols 1030-1033 illustrate the noise floor performance for this embodiment. As can be seen, the noise floor performance can vary for each of the openings and based on the frequency of the noise.

In FIG. 10B, a graph 1050 depicts a noise floor for frequencies of noise 1070 for an embodiment in which the sensor included separate openings for four (4) detectors 106 and one or more windows that include an ITO coating. In this embodiment, a surface resistivity of the ITO used was about 500 ohms per square inch. Symbols 1080-1083 illustrate the noise floor performance for this embodiment. As can be seen, the noise floor performance for this embodiment can vary less for each of the openings and provide lower noise floors in comparison to the embodiment of FIG. 10A.

Figure 11A:
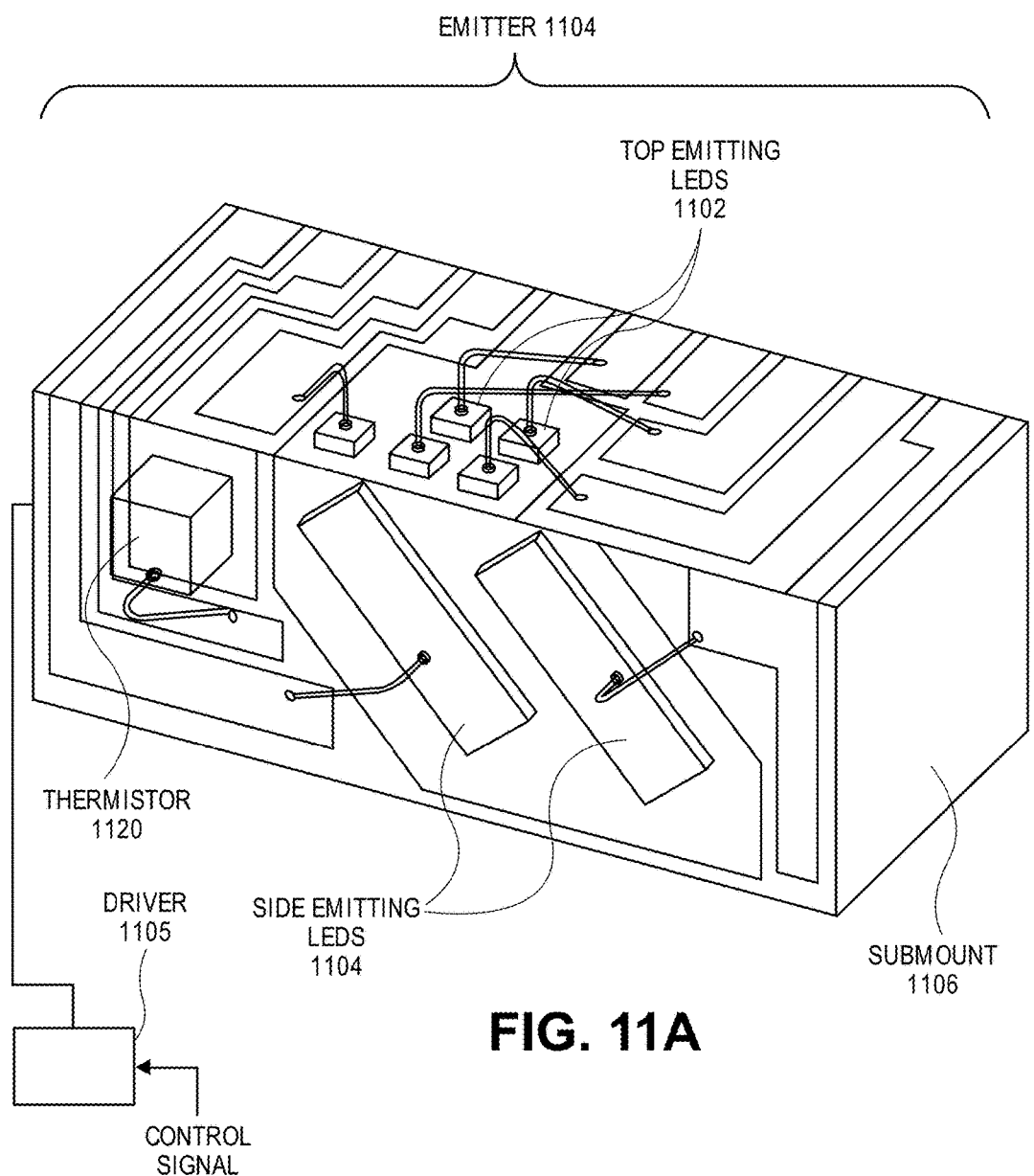
FIG. 11A illustrates an exemplary emitter that may be employed in the sensor, according to an embodiment of the disclosure.

FIG. 11A illustrates an example structure for configuring the set of optical sources of the emitters described above. As shown, an emitter 104 can include a driver 1105, a thermistor 1120, a set of top-emitting LEDs 1102 for emitting red and/or infrared light, a set of side-emitting LEDs 1104 for emitting near infrared light, and a submount 1106.

The thermistor 1120 can be provided to compensate for temperature variations. For example, the thermistor 1120 can be provided to allow for wavelength centroid and power drift of LEDs 1102 and 1104 due to heating. In addition, other thermistors can be employed, for example, to measure a temperature of a measurement site. The temperature can be displayed on a display device and used by a caregiver. Such a temperature can also be helpful in correcting for wavelength drift due to changes in water absorption, which can be temperature dependent, thereby providing more accurate data useful in detecting blood analytes like glucose. In addition, using a thermistor or other type of temperature sensitive device may be useful for detecting extreme temperatures at the measurement site that are too hot or too cold. The presence of low perfusion may also be detected, for example, when the finger of a patient has become too cold. Moreover, shifts in temperature at the measurement site can alter the absorption spectrum of water and other tissue in the measurement cite. A thermistor's temperature reading can be used to adjust for the variations in absorption spectrum changes in the measurement site.

The driver 1105 can provide pulses of current to the emitter 1104. In an embodiment, the driver 1105 drives the emitter 1104 in a progressive fashion, for example, in an alternating manner based on a control signal from, for example, a processor (e.g., the processor 110). For example, the driver 1105 can drive the emitter 1104 with a series of pulses to about 1 milliwatt (mW) for visible light to light at about 1300 nm and from about 40 mW to about 100 mW for light at about 1600 nm to about 1700 nm. However, a wide number of driving powers and driving methodologies can be used. The driver 1105 can be synchronized with other parts of the sensor and can minimize or reduce any jitter in the timing of pulses of optical radiation emitted from the emitter 1104. In some embodiments, the driver 1105 is capable of driving the emitter 1104 to emit an optical radiation in a pattern that varies by less than about 10 parts-per-million; however other amounts of variation can be used.

The submount 1106 provides a support structure in certain embodiments for aligning the top-emitting LEDs 1102 and the side-emitting LEDs 1104 so that their optical radiation is transmitted generally towards the measurement site. In some embodiments, the submount 1106 is also constructed of aluminum nitride (AlN) or beryllium oxide (BEO) for heat dissipation, although other materials or combinations of materials suitable for the submount 1106 can be used.

Figure 11B:
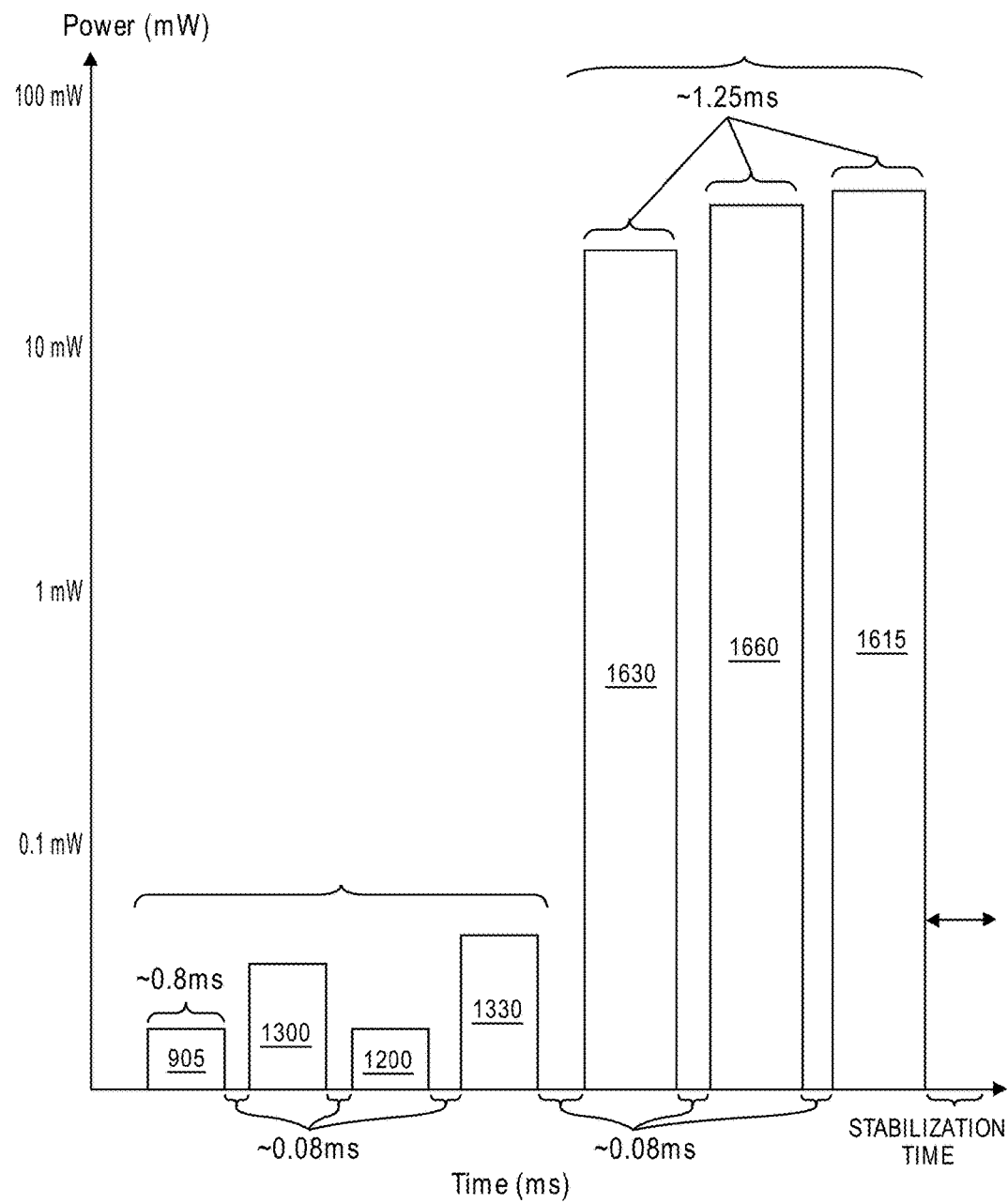
FIG. 11B illustrates a configuration of emitting optical radiation into a measurement site for measuring blood constituents, according to an embodiment of the disclosure.

FIG. 11B illustrates a configuration of emitting optical radiation into a measurement site for measuring a blood constituent or analyte like glucose. In some embodiments, emitter 104 may be driven in a progressive fashion to minimize noise and increase SNR of sensor 101. For example, emitter 104 may be driven based on a progression of power/current delivered to LEDs 1102 and 1104.

In some embodiments, emitter 104 may be configured to emit pulses centered about 905 nm, about 1050 nm, about 1200 nm, about 1300 nm, about 1330 nm, about 1610 nm, about 1640 nm, and about 1665 nm. In another embodiment, the emitter 104 may emit optical radiation ranging from about 860 nm to about 950 nm, about 950 nm to about 1100 nm, about 1100 nm to about 1270 nm, about 1250 nm to about 1350 nm, about 1300 nm to about 1360 nm, and about 1590 nm to about 1700 nm. Of course, emitter 104 may be configured to transmit any of a variety of wavelengths of visible, or near-infrared optical radiation.

For purposes of illustration, FIG. 11B shows a sequence of pulses of light at wavelengths of around 905 nm, around 1200 nm, around 1300 nm, and around 1330 nm from top emitting LEDs 1102. FIG. 11B also shows that emitter 104 may then emit pulses centered at around 1630 nm, around 1660 nm, and around 1615 nm from side emitting LEDs 1104. Emitter 104 may be progressively driven at higher power/current. This progression may allow driver circuit 105 to stabilize in its operations, and thus, provide a more stable current/power to LEDs 1102 and 1104.

For example, as shown in FIG. 11B, the sequence of optical radiation pulses are shown having a logarithmic-like progression in power/current. In some embodiments, the timing of these pulses is based on a cycle of about 400 slots running at 48 kHz (e.g. each time slot may be approximately 0.02 ms or 20 microseconds). An artisan will recognize that term "slots" includes its ordinary meaning, which includes a time period that may also be expressed in terms of a frequency. In the example shown, pulses from top emitting LEDs 1102 may have a pulse width of about 40 time slots (e.g., about 0.8 ms) and an off period of about 4 time slots in between. In addition, pulses from side emitting LEDs 1104 (e.g., or a laser diode) may have a pulse width of about 60 time slots (e.g., about 1.25 ms) and a similar off period of about 4 time slots. A pause of about 70 time slots (e.g. 1.5 ms) may also be provided in order to allow driver circuit 1105 to stabilize after operating at higher current/power.

As shown in FIG. 11B, top emitting LEDs 1102 may be initially driven with a power to approximately 1 mW at a current of about 20-100 mA. Power in these LEDs may also be modulated by using a filter or covering of black dye to reduce power output of LEDs. In this example, top emitting LEDs 1102 may be driven at approximately 0.02 to 0.08 mW. The sequence of the wavelengths may be based on the current requirements of top emitting LEDs 502 for that particular wavelength. Of course, in other embodiments, different wavelengths and sequences of wavelengths may be output from emitter 104.

Subsequently, side emitting LEDs 1104 may be driven at higher powers, such as about 40-100 mW and higher currents of about 600-800 mA. This higher power may be employed in order to compensate for the higher opacity of tissue and water in measurement site 102 to these wavelengths. For example, as shown, pulses at about 1630 nm, about 1660 nm, and about 1615 nm may be output with progressively higher power, such as at about 40 mW, about 50 mW, and about 60 mW, respectively. In this embodiment, the order of wavelengths may be based on the optical characteristics of that wavelength in tissue as well as the current needed to drive side emitting LEDs 1104. For example, in this embodiment, the optical pulse at about 1615 nm is driven at the highest power due to its sensitivity in detecting analytes like glucose and the ability of light at this wavelength to penetrate tissue. Of course, different wavelengths and sequences of wavelengths may be output from emitter 104.

As noted, this progression may be useful in some embodiments because it allows the circuitry of driver circuit 1105 to stabilize its power delivery to LEDs 1102 and 1104. Driver circuit 1105 may be allowed to stabilize based on the duty cycle of the pulses or, for example, by configuring a variable waiting period to allow for stabilization of driver circuit 1105. Of course, other variations in power/current and wavelength may also be employed in the present disclosure.

Modulation in the duty cycle of the individual pulses may also be useful because duty cycle can affect the signal noise ratio of the system 100. That is, as the duty cycle is increased so may the signal to noise ratio.

Furthermore, as noted above, driver circuit 1105 may monitor temperatures of the LEDs 1102 and 1104 using the thermistor 1120 and adjust the output of LEDs 1102 and 1104 accordingly. Such a temperature may be to help sensor 101 correct for wavelength drift due to changes in water absorption, which can be temperature dependent.

Figure 11C:
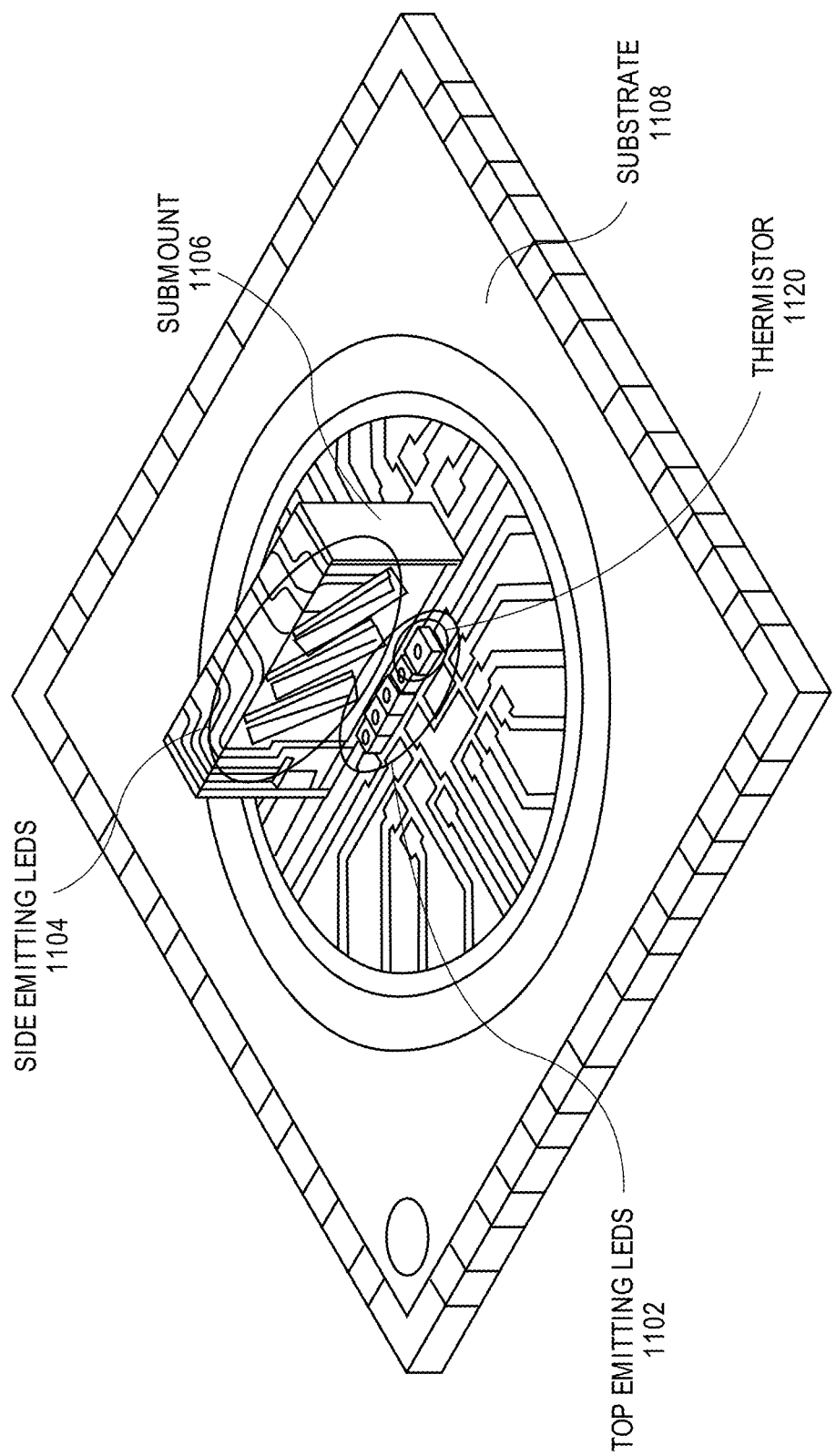
FIG. 11C illustrates another exemplary emitter that may be employed in the sensor according to an embodiment of the disclosure.

FIG. 11C illustrates another exemplary emitter that may be employed in the sensor according to an embodiment of the disclosure. As shown, the emitter 104 can include components mounted on a substrate 1108 and on submount 1106. In particular, top-emitting LEDs 1102 for emitting red and/or infrared light may be mounted on substrate 1108. Side emitting LEDS 1104 may be mounted on submount 1106. As noted, side-emitting LEDs 1104 may be included in emitter 104 for emitting near infrared light.

As also shown, the sensor of FIG. 11C may include a thermistor 1120. As noted, the thermistor 1120 can be provided to compensate for temperature variations. The thermistor 1120 can be provided to allow for wavelength centroid and power drift of LEDs 1102 and 1104 due to heating. In addition, other thermistors (not shown) can be employed, for example, to measure a temperature of a measurement site. Such a temperature can be helpful in correcting for wavelength drift due to changes in water absorption, which can be temperature dependent, thereby providing more accurate data useful in detecting blood analytes like glucose.

Figure 11D:
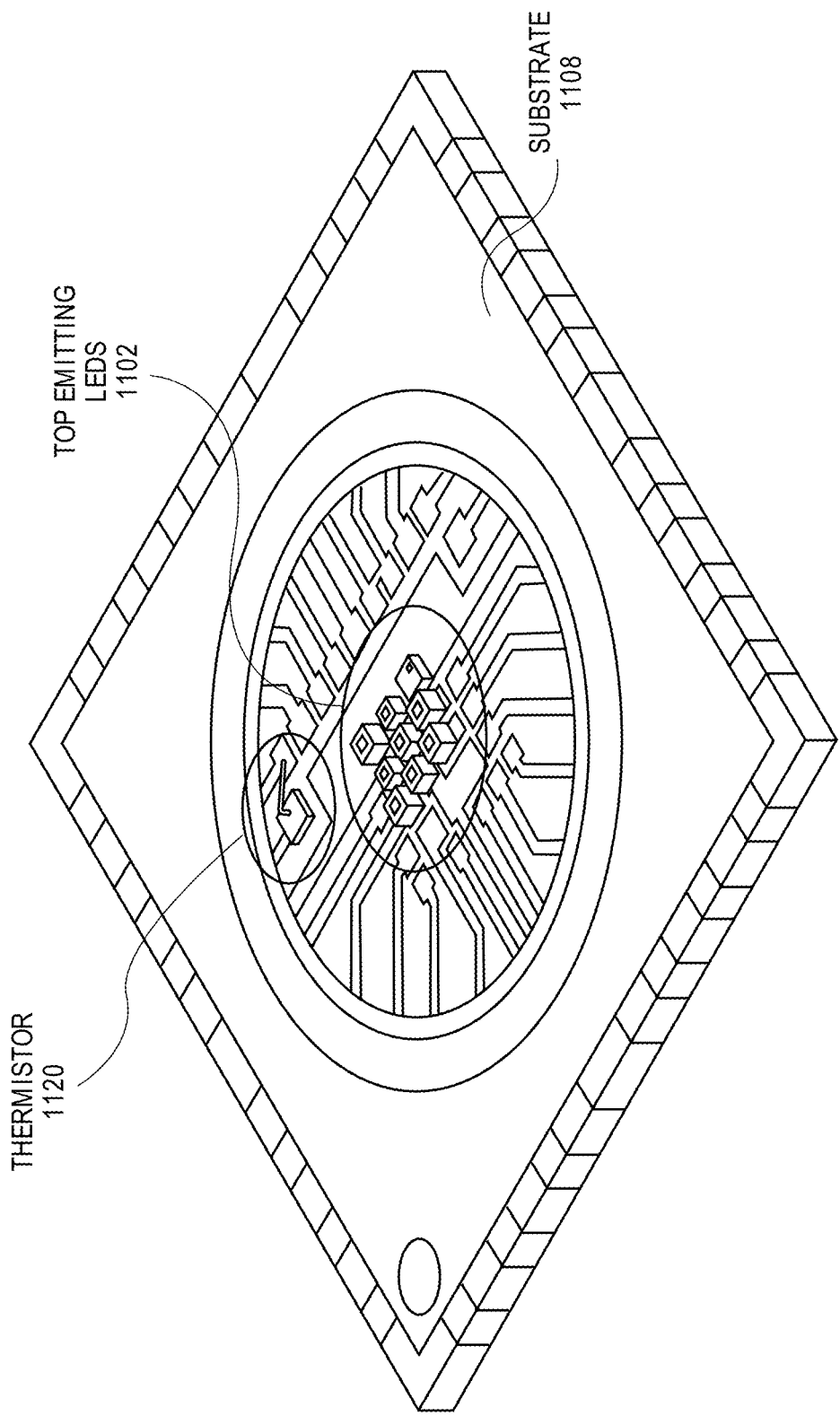
FIG. 11D illustrates another exemplary emitter that may be employed in the sensor according to an embodiment of the disclosure.

In some embodiments, the emitter 104 may be implemented without the use of side emitting LEDs. For example, certain blood constituents, such as total hemoglobin, can be measured by embodiments of the disclosure without the use of side emitting LEDs. FIG. 11D illustrates another exemplary emitter that may be employed in the sensor according to an embodiment of the disclosure. In particular, an emitter 104 that is configured for a blood constituent, such as total hemoglobin, is shown. The emitter 104 can include components mounted on a substrate 1108. In particular, top-emitting LEDs 1102 for emitting red and/or infrared light may be mounted on substrate 1108.

As also shown, the emitter of FIG. 11D may include a thermistor 1120. The thermistor 1120 can be provided to compensate for temperature variations. The thermistor 1120 can be provided to allow for wavelength centroid and power drift of LEDs 1102 due to heating.

Figure 12A:
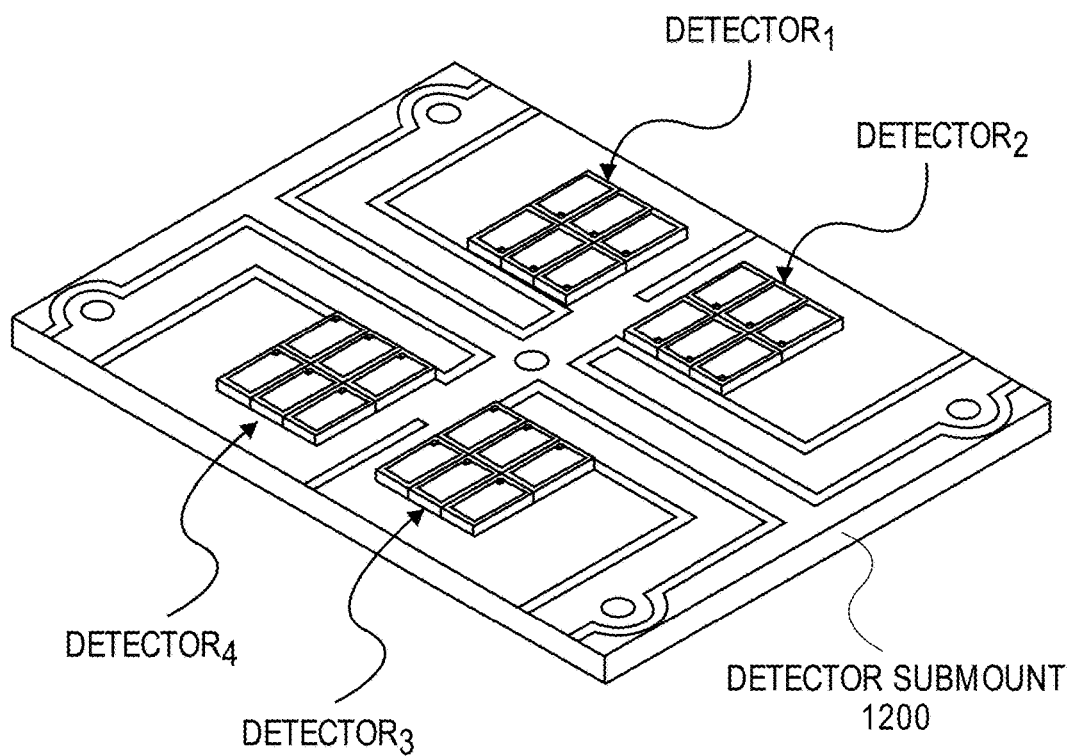
FIG. 12A illustrates an example detector portion that may be employed in an embodiment of a sensor, according to an embodiment of the disclosure.

FIG. 12A illustrates a detector submount 1200 having photodiode detectors that are arranged in a grid pattern on the detector submount 1200 to capture light at different quadrants from a measurement site. One detector submount 1200 can be placed under each window of the sensors described above, or multiple windows can be placed over a single detector submount 1200. The detector submount 1200 can also be used with the partially cylindrical protrusion 605 described above with respect to FIG. 6.

The detectors include photodiode detectors 1-4 that are arranged in a grid pattern on the submount 1200 to capture light at different quadrants from the measurement site. As noted, other patterns of photodiodes, such as a linear row, or logarithmic row, can also be employed in certain embodiments.

As shown, the detectors 1-4 may have a predetermined spacing from each other, or spatial relationship among one another that result in a spatial configuration. This spatial configuration can be configured to purposefully create a variation of path lengths among detectors 106 and the point light source discussed above.

Detectors may hold multiple (e.g., two, three, four, etc.) photodiode arrays that are arranged in a two-dimensional grid pattern. Multiple photodiode arrays may also be useful to detect light piping (i.e., light that bypasses measurement site 102). As shown, walls may separate the individual photodiode arrays to prevent mixing of light signals from distinct quadrants. In addition, as noted, the detectors may be covered by windows of transparent material, such as glass, plastic, etc., to allow maximum transmission of power light captured. As noted, this window may comprise some shielding in the form of an embedded grid of wiring, or a conductive layer or coating.

Figure 12B:
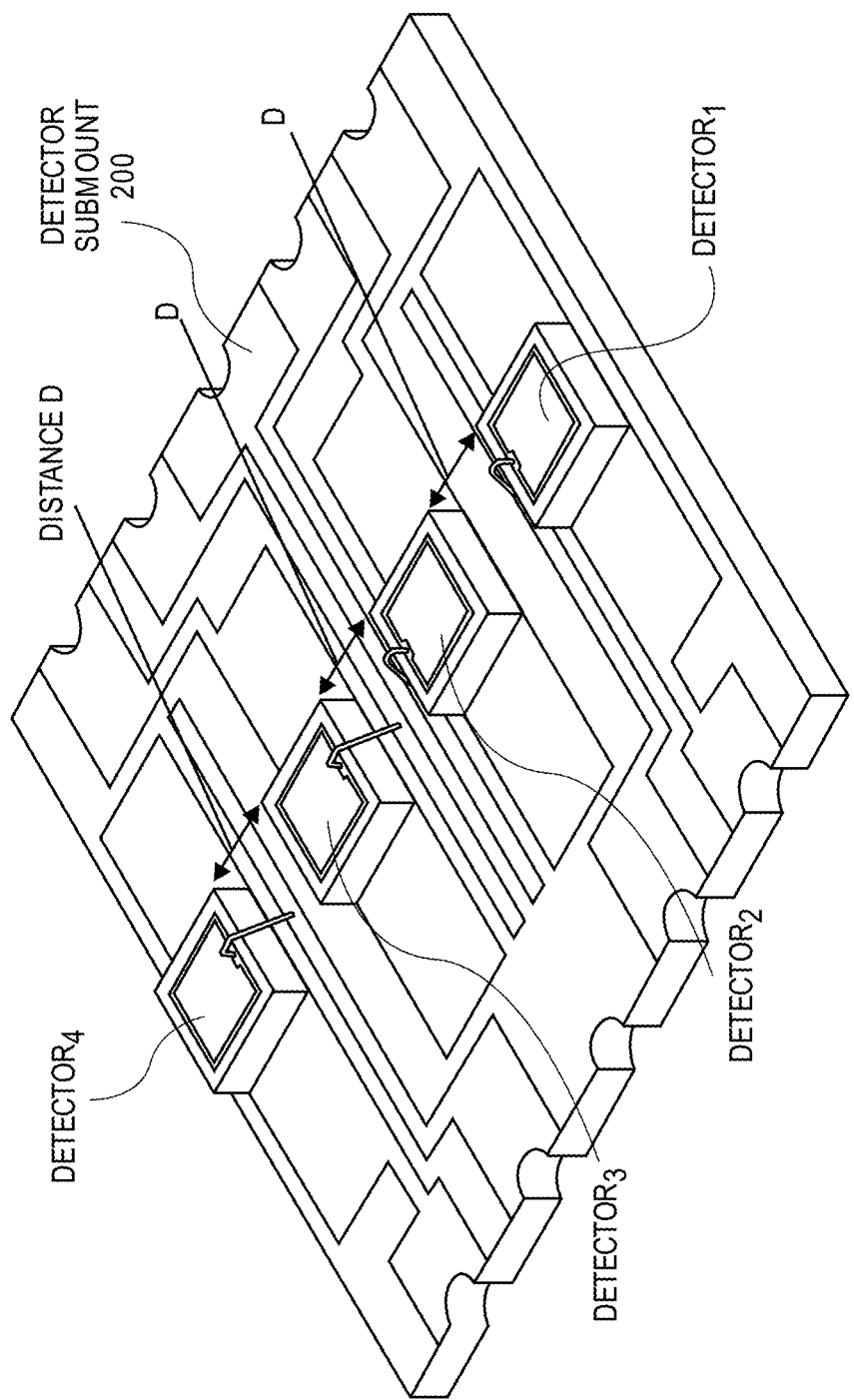
FIGS. 12B through 12D illustrate exemplary arrangements of detectors that may be employed in an embodiment of the sensor, according to some embodiments of the disclosure.
Figure 12C:
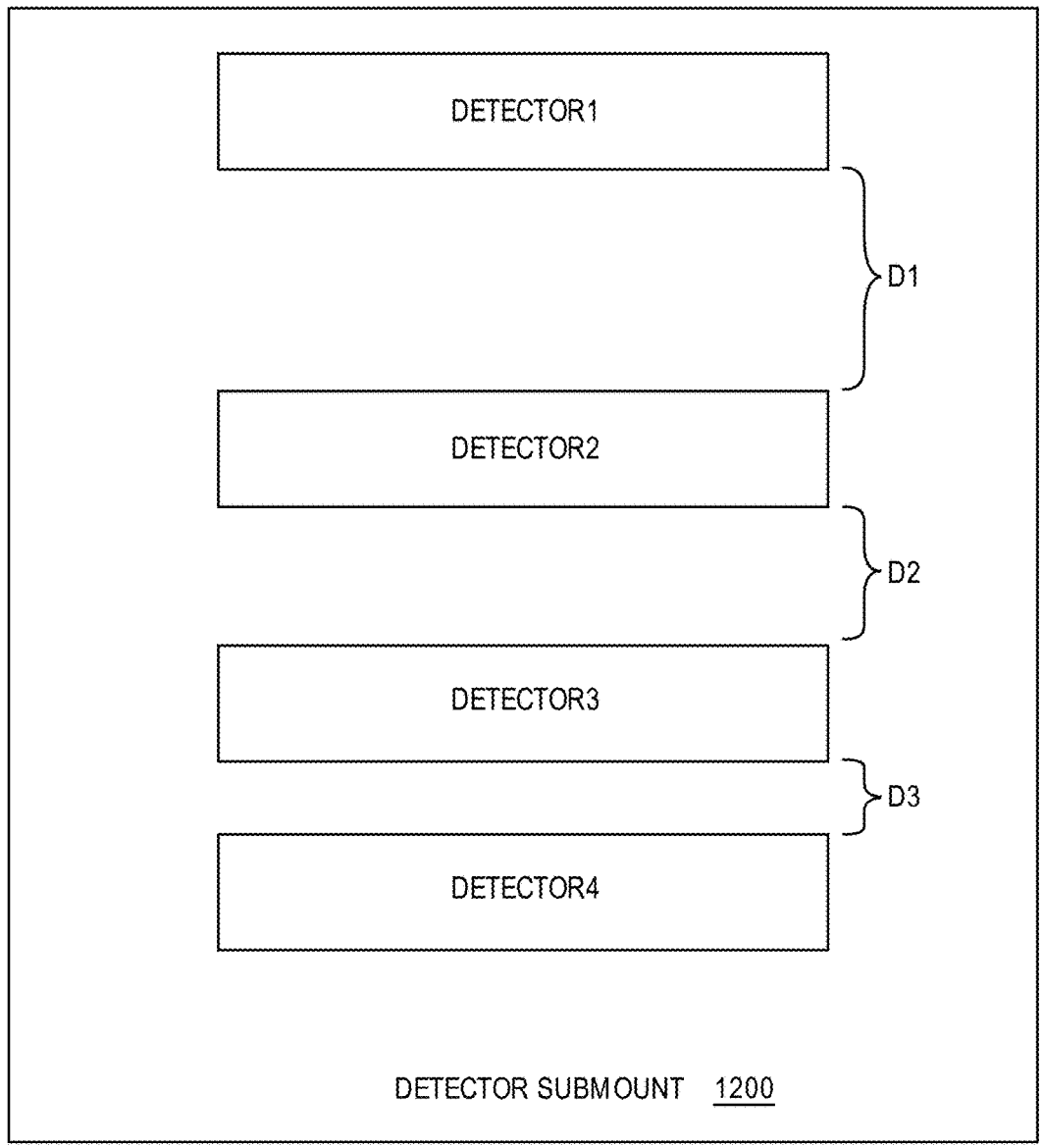
Figure 12D:
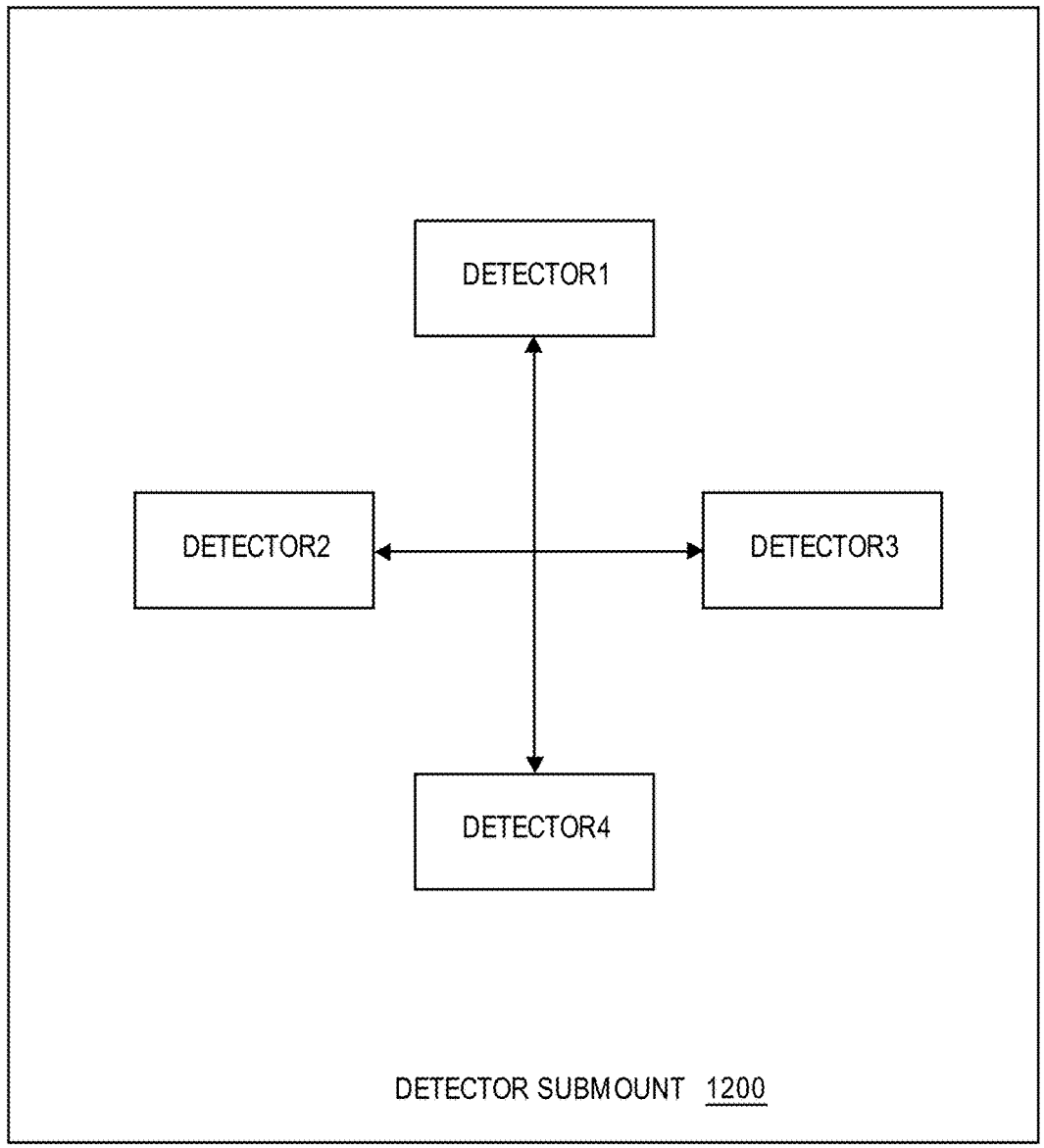

FIGS. 12B through 12D illustrate a simplified view of exemplary arrangements and spatial configurations of photodiodes for detectors 106. As shown, detectors 106 may comprise photodiode detectors 1-4 that are arranged in a grid pattern on detector submount 1200 to capture light at different quadrants from measurement site 102.

As noted, other patterns of photodiodes may also be employed in embodiments of the present disclosure, including, for example, stacked or other configurations recognizable to an artisan from the disclosure herein. For example, detectors 106 may be arranged in a linear array, a logarithmic array, a two-dimensional array, and the like. Furthermore, an artisan will recognize from the disclosure herein that any number of detectors 106 may be employed by embodiments of the present disclosure.

For example, as shown in FIG. 12B, detectors 106 may comprise photodiode detectors 1-4 that are arranged in a substantially linear configuration on submount 1200. In this embodiment shown, photodiode detectors 1-4 are substantially equally spaced apart (e.g., where the distance D is substantially the same between detectors 1-4).

In FIG. 12C, photodiode detectors 1-4 may be arranged in a substantially linear configuration on submount 1200, but may employ a substantially progressive, substantially logarithmic, or substantially semi-logarithmic spacing (e.g., where distances D1>D2>D3). This arrangement or pattern may be useful for use on a patient's finger and where the thickness of the finger gradually increases.

In FIG. 12D, a different substantially grid pattern on submount 1200 of photodiode detectors 1-4 is shown. As noted, other patterns of detectors may also be employed in embodiments of the present invention.

FIGS. 12E through 12H illustrate several embodiments of photodiodes that may be used in detectors 106. As shown in these figures, a photodiode 1202 of detector 106 may comprise a plurality of active areas 1204, These active areas 204 may be coupled together via a common cathode 1206 or anode 1208 in order to provide a larger effective detection area.

Figure 12E:
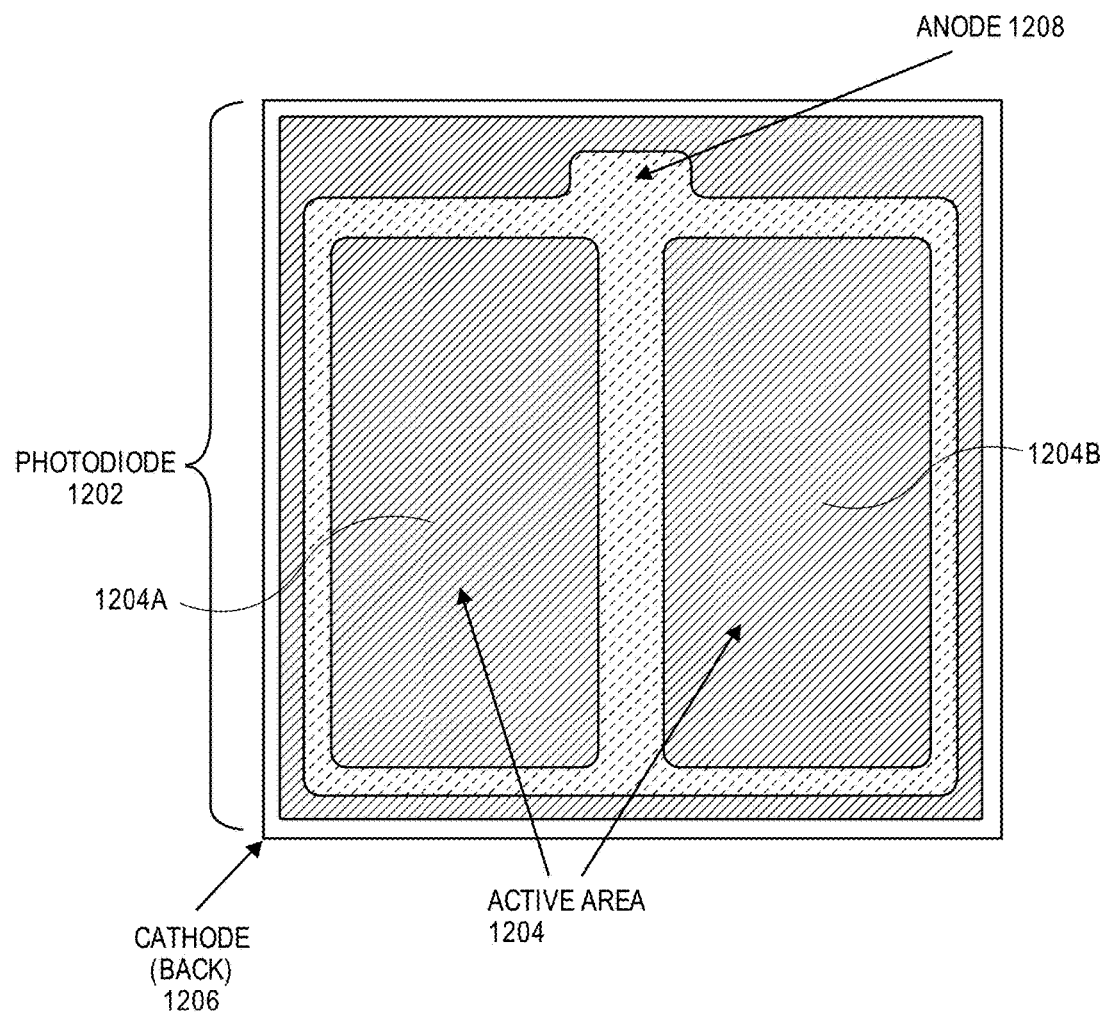
FIGS. 12E through 12H illustrate exemplary structures of photodiodes that may be employed in embodiments of the detectors, according to some embodiments of the disclosure.
Figure 12F:
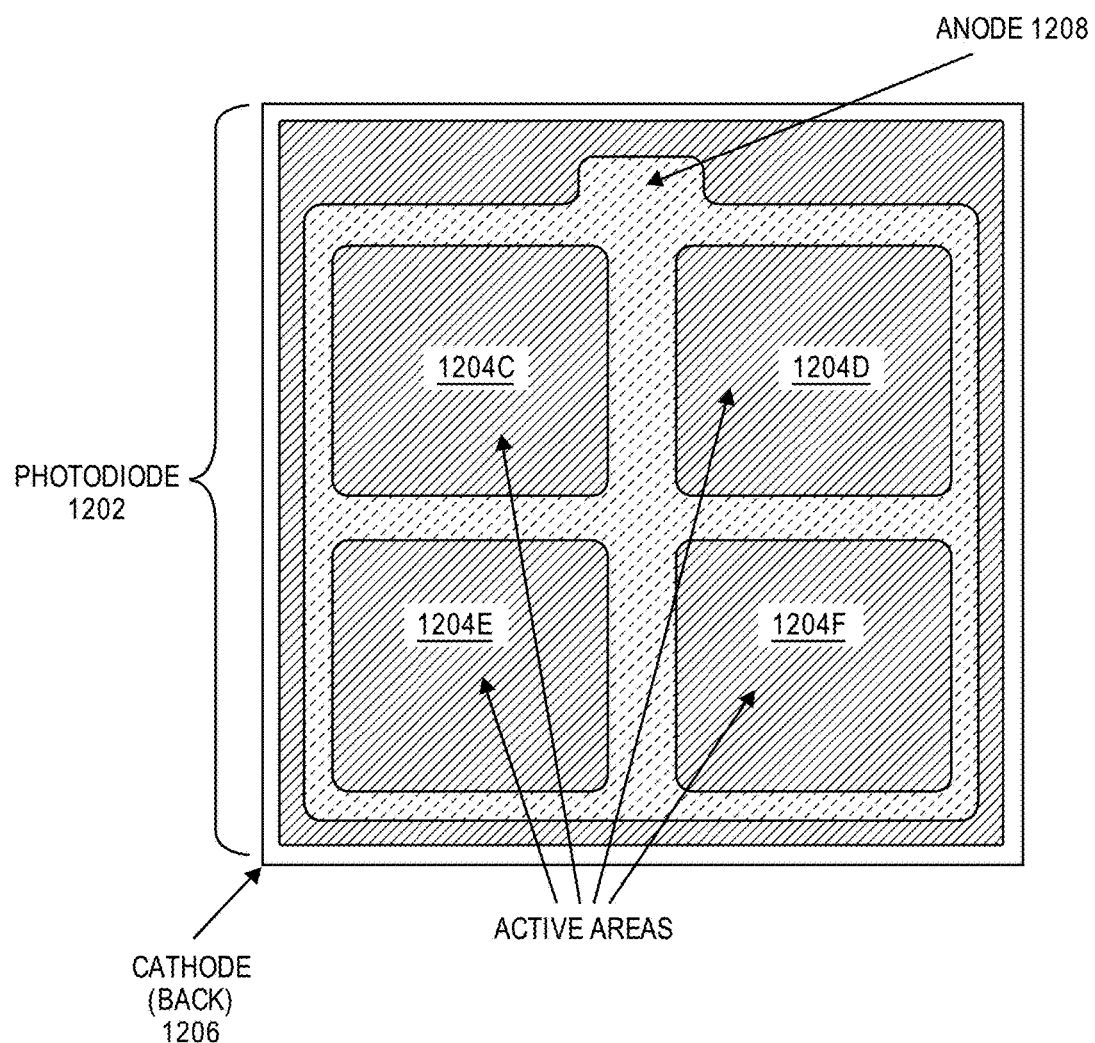
Figure 12G:
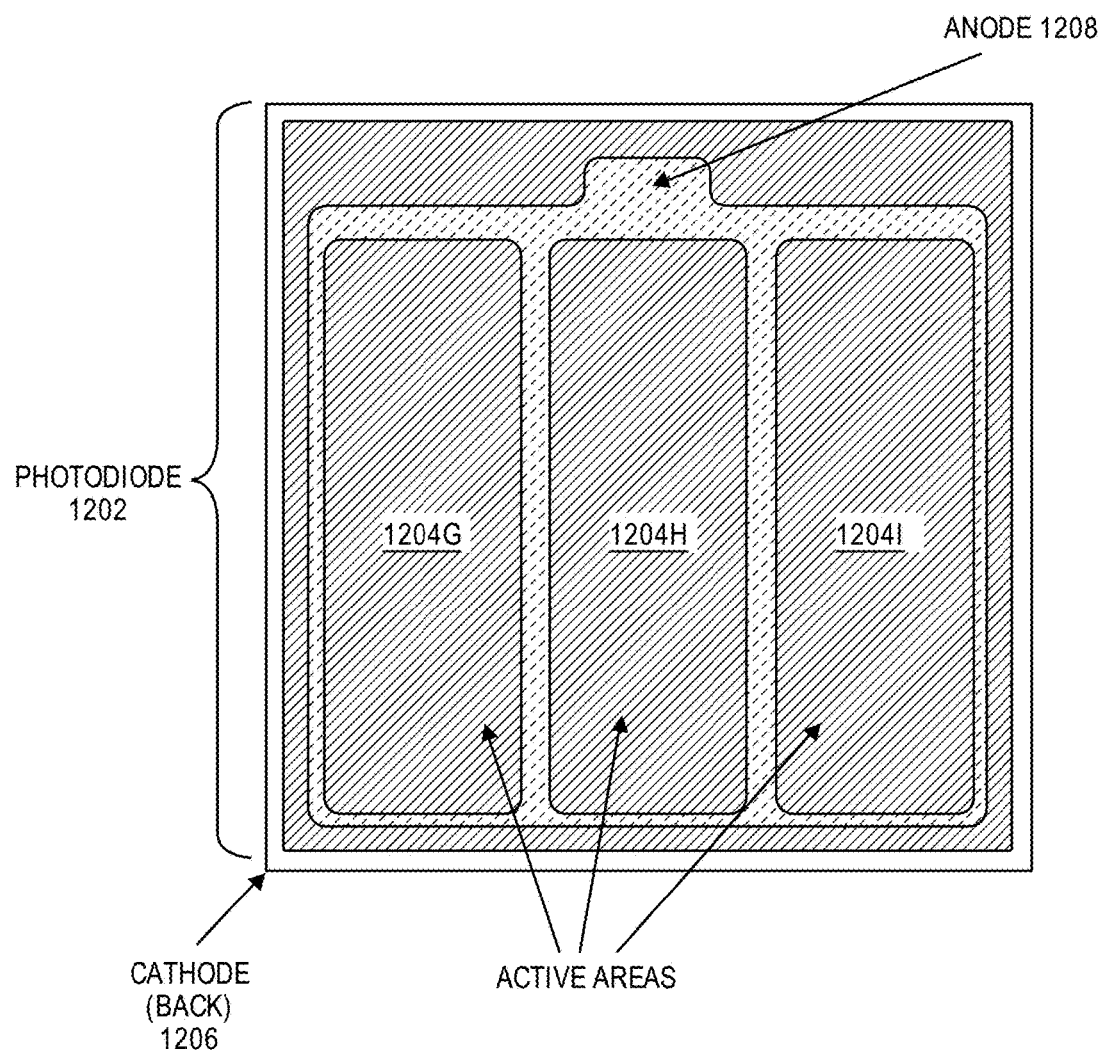
Figure 12H:
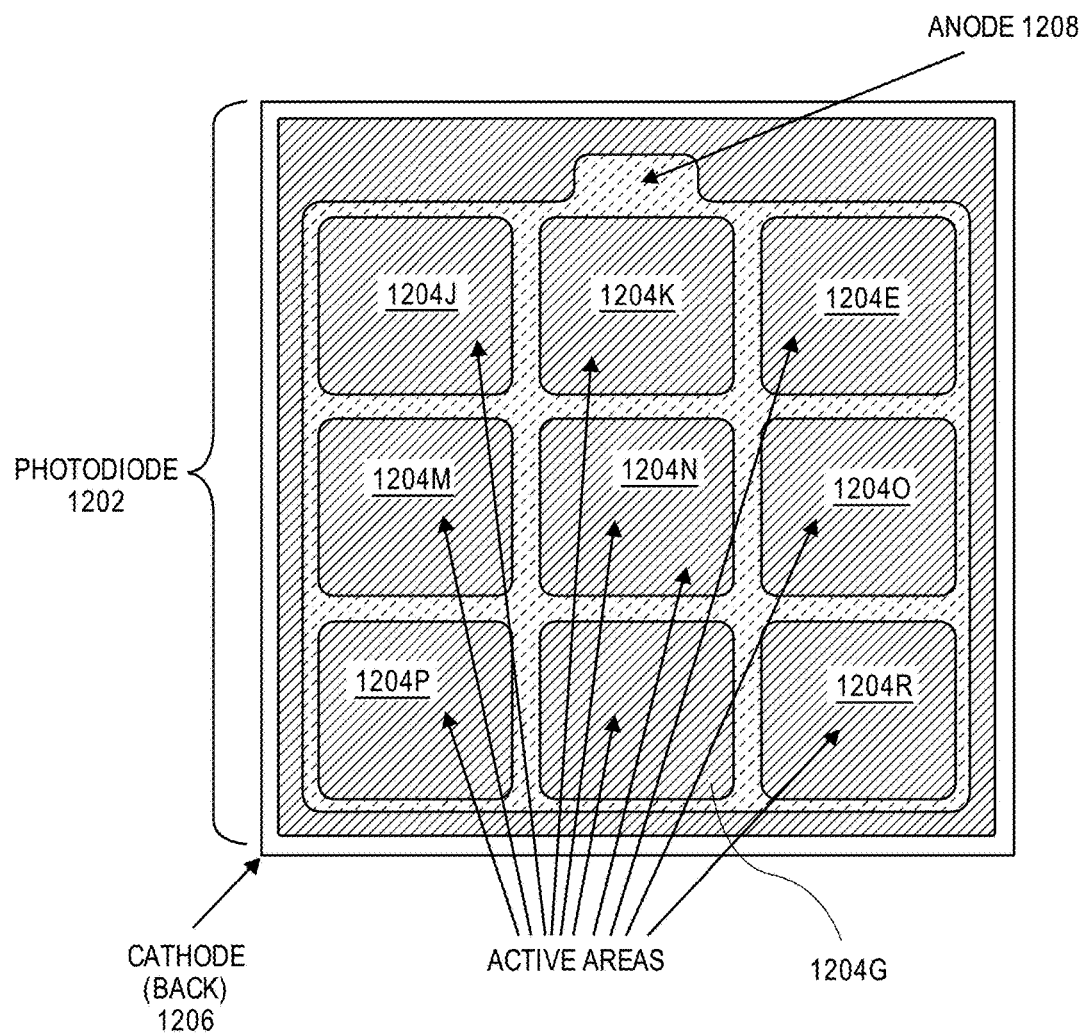

In particular, as shown in FIG. 12E, photodiode 1202 may comprise two (2) active areas 1204$a$ and 1204$b$. In FIG. 12F, photodiode 1202 may comprise four (4) active areas 1204$c$-$f$. In FIG. 12G, photodiode 1202 may comprise three (3) active areas 1204$g$-$i$. In FIG. 12H, photodiode 1202 may comprise nine (9) active areas 1204$j$-$r$. The use of smaller active areas may be useful because smaller active areas can be easier to fabricate and can be fabricated with higher purity. However, one skilled in the art will recognize that various sizes of active areas may be employed in the photodiode 1202.

Figure 13:
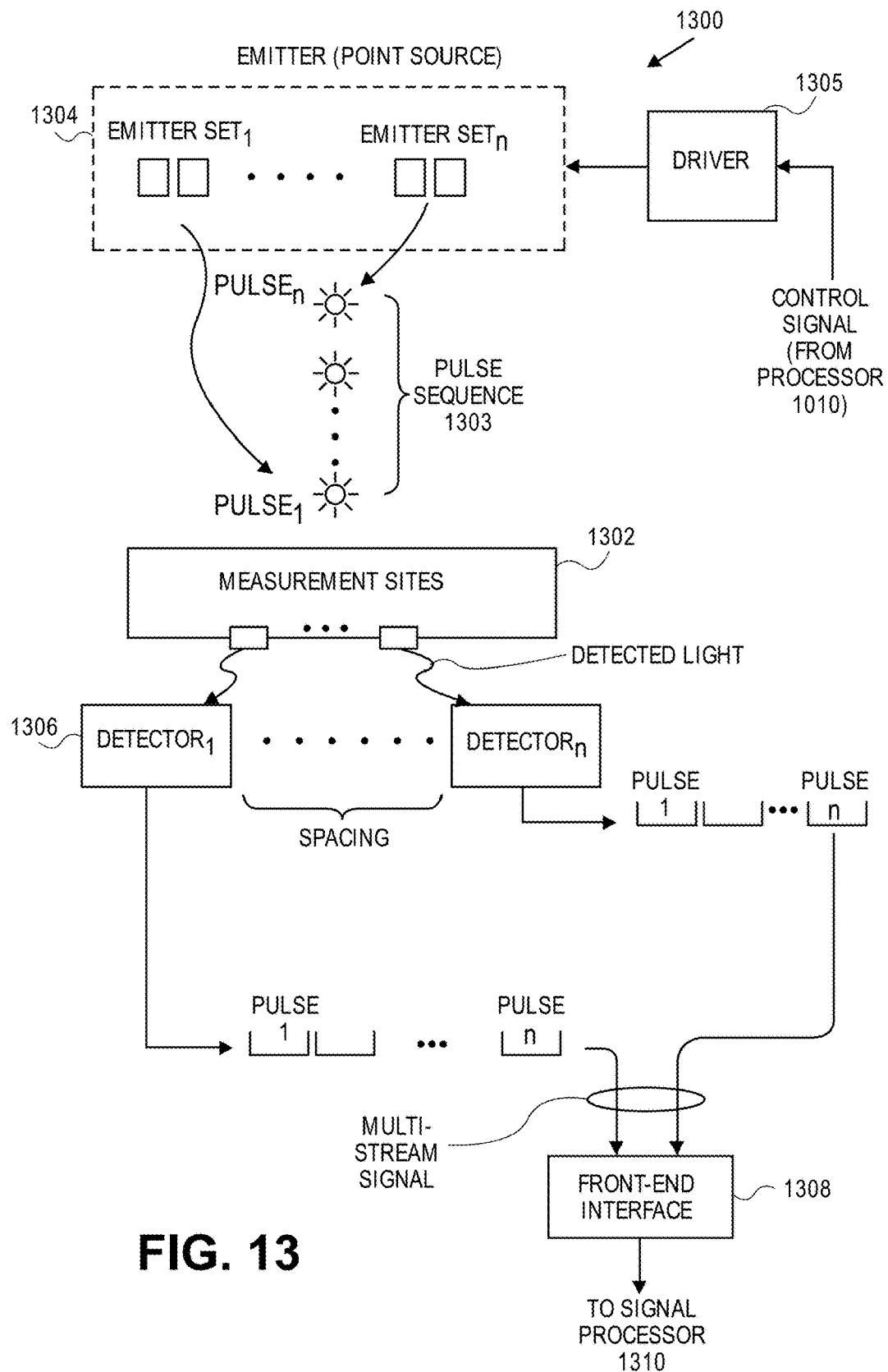
FIG. 13 illustrates an example multi-stream operation of the system of FIG. 1, according to an embodiment of the disclosure.

FIG. 13 illustrates an example multi-stream process 1300. The multi-stream process 1300 can be implemented by the data collection system 100 and/or by any of the sensors described above. As shown, a control signal from a signal processor 1310 controls a driver 1305. In response, an emitter 1304 generates a pulse sequence 1303 from its emitter (e.g., its LEDs) into a measurement site or sites 1302. As described above, in some embodiments, the pulse sequence 1303 is controlled to have a variation of about 10 parts per million or less. Of course, depending on the analyte desired, the tolerated variation in the pulse sequence 1303 can be greater (or smaller).

In response to the pulse sequence 1300, detectors 1 to n (n being an integer) in a detector 1306 capture optical radiation from the measurement site 1302 and provide respective streams of output signals. Each signal from one of detectors 1-n can be considered a stream having respective time slots corresponding to the optical pulses from emitter sets 1-n in the emitter 1304. Although n emitters and n detectors are shown, the number of emitters and detectors need not be the same in certain implementations.

A front end interface 1308 can accept these multiple streams from detectors 1-n and deliver one or more signals or composite signal(s) back to the signal processor 1310. A stream from the detectors 1-n can thus include measured light intensities corresponding to the light pulses emitted from the emitter 1304.

The signal processor 1310 can then perform various calculations to measure the amount of glucose and other analytes based on these multiple streams of signals. In order to help explain how the signal processor 1310 can measure analytes like glucose, a primer on the spectroscopy employed in these embodiments will now be provided.

Spectroscopy is premised upon the Beer-Lambert law. According to this law, the properties of a material, e.g., glucose present in a measurement site, can be deterministically calculated from the absorption of light traveling through the material. Specifically, there is a logarithmic relation between the transmission of light through a material and the concentration of a substance and also between the transmission and the length of the path traveled by the light. As noted, this relation is known as the Beer-Lambert law.

The Beer-Lambert law is usually written as:

Absorbance $A=m*b*c$, where:

m is the wavelength-dependent molar absorptivity coefficient (usually expressed in units of $M^{-1}$ $cm^{-1}$);

b is the mean path length; and c is the analyte concentration (e.g., the desired parameter).

In spectroscopy, instruments attempt to obtain the analyte concentration (c) by relating absorbance (A) to transmittance (T). Transmittance is a proportional value defined as:

$T=I/I_o$, where:

I is the light intensity measured by the instrument from the measurement site; and $I_o$ is the initial light intensity from the emitter.

Absorbance (A) can be equated to the transmittance (T) by the equation:

$A=-\log T$

Therefore, substituting equations from above:

$A=-\log(I/I_o)$

In view of this relationship, spectroscopy thus relies on a proportional-based calculation of $-\log(I/I_o)$ and solving for analyte concentration (c).

Typically, in order to simplify the calculations, spectroscopy will use detectors that are at the same location in order to keep the path length (b) a fixed, known constant. In addition, spectroscopy will employ various mechanisms to definitively know the transmission power ($I_o$), such as a photodiode located at the light source. This architecture can be viewed as a single channel or single stream sensor, because the detectors are at a single location.

However, this scheme can encounter several difficulties in measuring analytes, such as glucose. This can be due to the high overlap of absorption of light by water at the wavelengths relevant to glucose as well as other factors, such as high self-noise of the components.

Embodiments of the present disclosure can employ a different approach that in part allows for the measurement of analytes like glucose. Some embodiments can employ a bulk, non-pulsatile measurement in order to confirm or validate a pulsatile measurement. In addition, both the non-pulsatile and pulsatile measurements can employ, among other things, the multi-stream operation described above in order to attain sufficient SNR. In particular, a single light source having multiple emitters can be used to transmit light to multiple detectors having a spatial configuration.

A single light source having multiple emitters can allow for a range of wavelengths of light to be used. For example, visible, infrared, and near infrared wavelengths can be employed. Varying powers of light intensity for different wavelengths can also be employed.

Secondly, the use of multiple-detectors in a spatial configuration allow for a bulk measurement to confirm or validate that the sensor is positioned correctly. This is because the multiple locations of the spatial configuration can provide, for example, topology information that indicates where the sensor has been positioned. Currently available sensors do not provide such information. For example, if the bulk measurement is within a predetermined range of values, then this can indicate that the sensor is positioned correctly in order to perform pulsatile measurements for analytes like glucose. If the bulk measurement is outside of a certain range or is an unexpected value, then this can indicate that the sensor should be adjusted, or that the pulsatile measurements can be processed differently to compensate, such as using a different calibration curve or adjusting a calibration curve. This feature and others allow the embodiments to achieve noise cancellation and noise reduction, which can be several times greater in magnitude that what is achievable by currently available technology.

In order to help illustrate aspects of the multi-stream measurement approach, the following example derivation is provided. Transmittance (T) can be expressed as:

$T=e^{-m*b*c}$

In terms of light intensity, this equation can also be rewritten as:

$I/I_o=e^{-m*b*c}$

Or, at a detector, the measured light (I) can be expressed as:

$I=I_o*e^{-m*b*c}$

As noted, in the present disclosure, multiple detectors (1 to n) can be employed, which results in $I_1 \ldots I_n$ streams of measurements. Assuming each of these detectors have their own path lengths, $b_1 \ldots b_n$, from the light source, the measured light intensities can be expressed as:

$I_n=I_o*e^{-m*b_n*c}$

The measured light intensities at any two different detectors can be referenced to each other. For example:

$I_1/I_n=(I_o*e^{-mb_1c})/(I_o*e^{-mb_nc})$

As can be seen, the terms, $I_o$, cancel out and, based on exponent algebra, the equation can be rewritten as:

$I_1/I_n=e^{-m(b_1-b_n)c}$

From this equation, the analyte concentration (c) can now be derived from bulk signals $l_1 \ldots l_n$ and knowing the respective mean path lengths $b_1$ and $b_n$. This scheme also allows for the cancelling out of $l_o$, and thus, noise generated by the emitter 1304 can be cancelled out or reduced. In addition, since the scheme employs a mean path length difference, any changes in mean path length and topological variations from patient to patient are easily accounted. Furthermore, this bulk-measurement scheme can be extended across multiple wavelengths. This flexibility and other features allow embodiments of the present disclosure to measure blood analytes like glucose.

For example, as noted, the non-pulsatile, bulk measurements can be combined with pulsatile measurements to more accurately measure analytes like glucose. In particular, the non-pulsatile, bulk measurement can be used to confirm or validate the amount of glucose, protein, etc. in the pulsatile measurements taken at the tissue at the measurement site(s) 1302. The pulsatile measurements can be used to measure the amount of glucose, hemoglobin, or the like that is present in the blood. Accordingly, these different measurements can be combined to thus determine analytes like blood glucose.

Figure 14A:
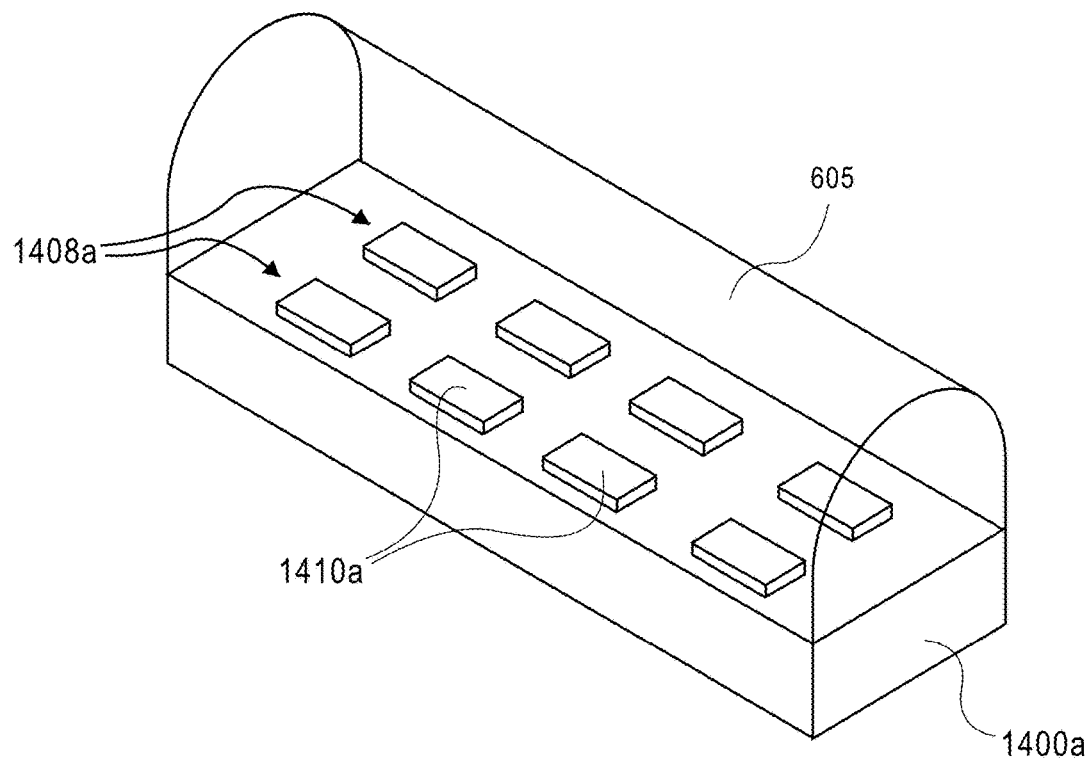
FIG. 14A illustrates another example detector portion having a partially cylindrical protrusion that can be employed in an embodiment of a sensor, according to an embodiment of the disclosure.

FIG. 14A illustrates an embodiment of a detector submount 1400*a* positioned beneath the partially cylindrical protrusion 605 of FIG. 6 (or alternatively, the protrusion 605*b*). The detector submount 1400*a* includes two rows 1408*a* of detectors 1410*a*. The partially cylindrical protrusion 605 can facilitate reducing the number and/or size of detectors used in a sensor because the protrusion 605 can act as a lens that focuses light onto a smaller area.

To illustrate, in some sensors that do not include the partially cylindrical protrusion 605, sixteen detectors can be used, including four rows of four detectors each. Multiple rows of detectors can be used to measure certain analytes, such as glucose or total hemoglobin, among others. Multiple rows of detectors can also be used to detect light piping (e.g., light that bypasses the measurement site). However, using more detectors in a sensor can add cost, complexity, and noise to the sensor.

Figure 14B:
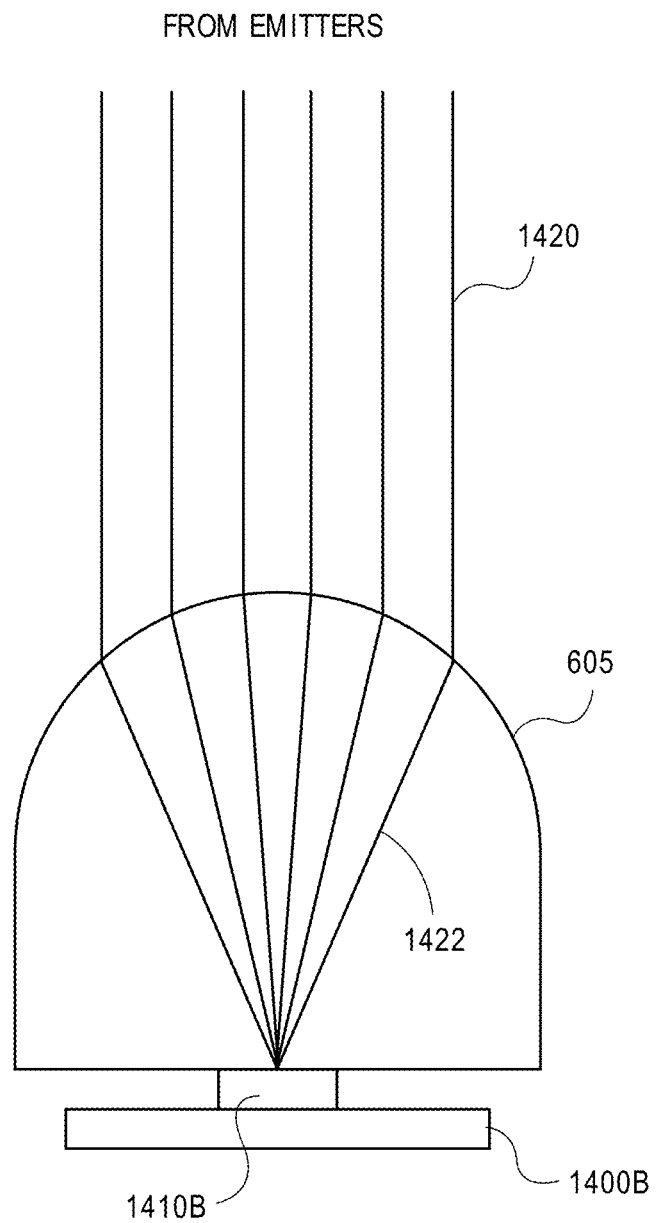
FIG. 14B depicts a front elevation view of the partially cylindrical protrusion of FIG. 14A.

Applying the partially cylindrical protrusion 605 to such a sensor, however, could reduce the number of detectors or rows of detectors used while still receiving the substantially same amount of light, due to the focusing properties of the protrusion 605 (see FIG. 14B). This is the example situation illustrated in FIG. 14—two rows 1408*a* of detectors 1410*a* are used instead of four. Advantageously, in certain embodiments, the resulting sensor can be more cost effective, have less complexity, and have an improved SNR, due to fewer and/or smaller photodiodes.

In other embodiments, using the partially cylindrical protrusion 605 can allow the number of detector rows to be reduced to one or three rows of four detectors. The number of detectors in each row can also be reduced. Alternatively, the number of rows might not be reduced but the size of the detectors can be reduced. Many other configurations of detector rows and sizes can also be provided.

FIG. 14B depicts a front elevation view of the partially cylindrical protrusion 605 (or alternatively, the protrusion 605*b*) that illustrates how light from emitters (not shown) can be focused by the protrusion 605 onto detectors. The protrusion 605 is placed above a detector submount 1400*b* having one or more detectors 1410*b* disposed thereon. The submount 1400*b* can include any number of rows of detectors 1410, although one row is shown.

Light, represented by rays 1420, is emitted from the emitters onto the protrusion 605. These light rays 1420 can be attenuated by body tissue (not shown). When the light rays 1420 enter the protrusion 605, the protrusion 605 acts as a lens to refract the rays into rays 1422. This refraction is caused in certain embodiments by the partially cylindrical shape of the protrusion 605. The refraction causes the rays 1422 to be focused or substantially focused on the one or more detectors 1410*b*. Since the light is focused on a smaller area, a sensor including the protrusion 605 can include fewer detectors to capture the same amount of light compared with other sensors.

Figure 14C:
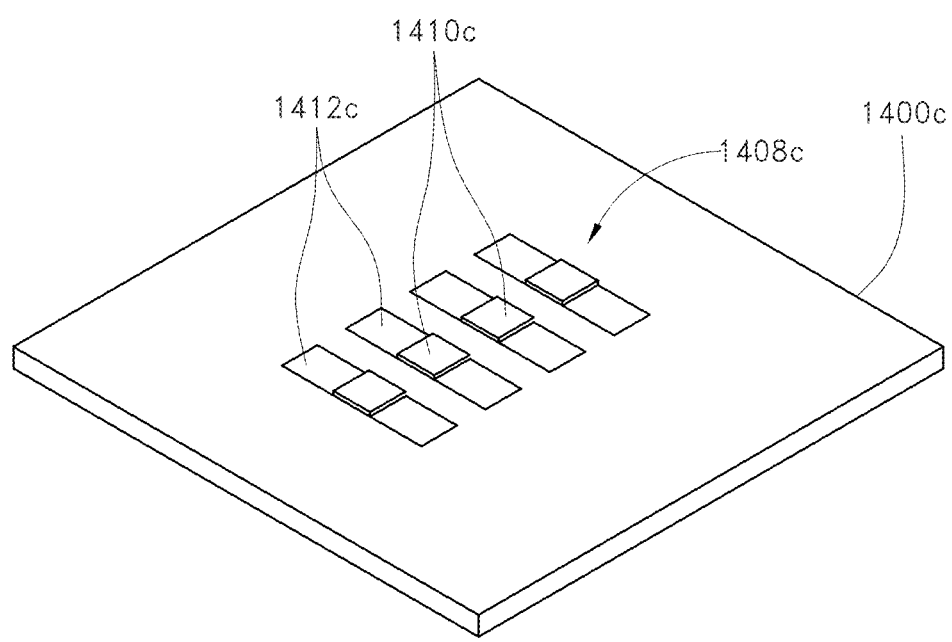
FIGS. 14C through 14E illustrate embodiments of a detector submount.

FIG. 14C illustrates another embodiment of a detector submount 1400*c*, which can be disposed under the protrusion 605*b* (or alternatively, the protrusion 605). The detector submount 1400*c* includes a single row 1408*c* of detectors 1410*c*. The detectors are electrically connected to conductors 1412*c*, which can be gold, silver, copper, or any other suitable conductive material.

Figure 14D:
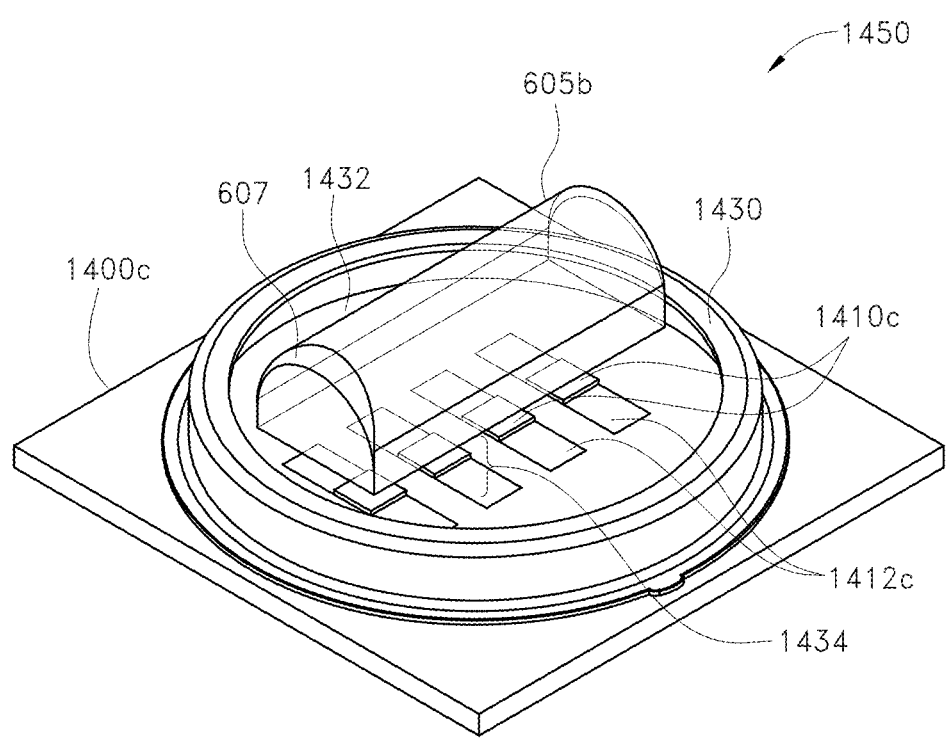
Figure 14E:
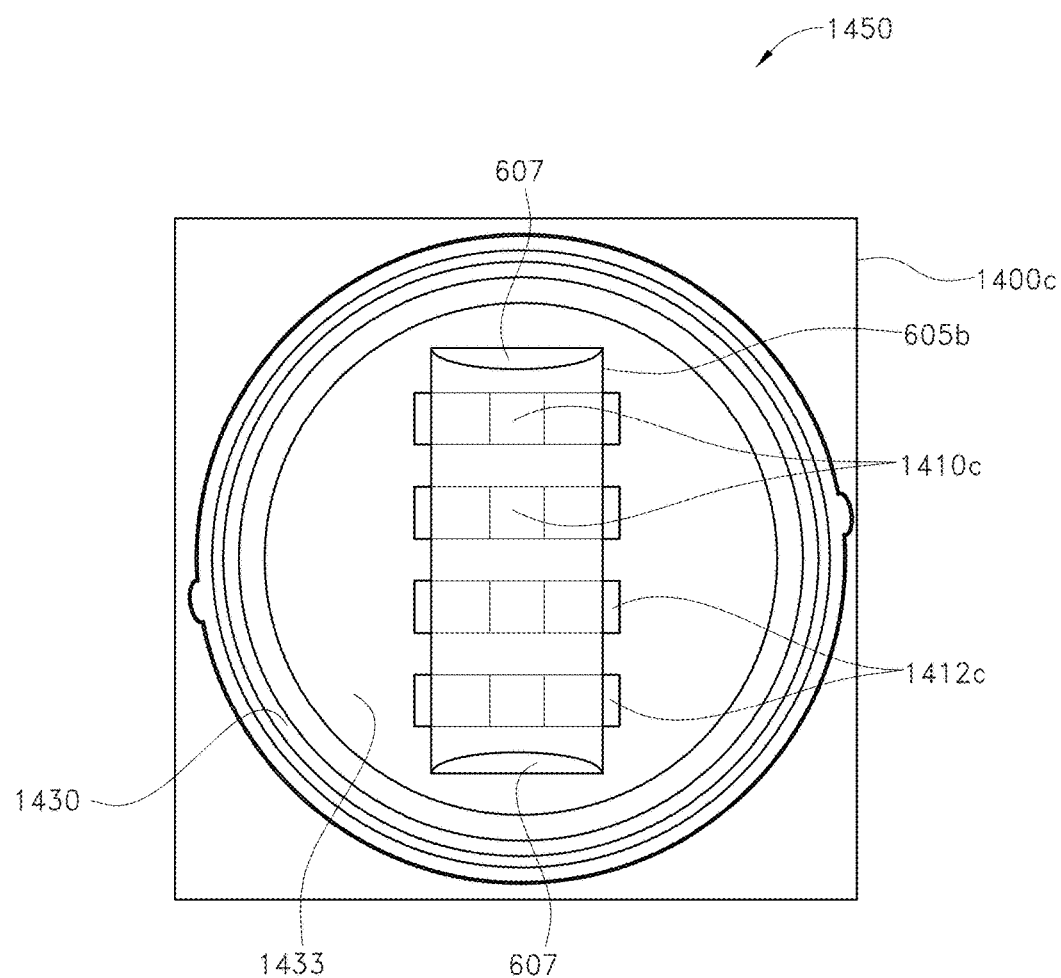

The detector submount 1400*c* is shown positioned under the protrusion 605*b* in a detector subassembly 1450 illustrated in FIG. 14D. A top-down view of the detector subassembly 1450 is also shown in FIG. 14E. In the detector subassembly 1450, a cylindrical housing 1430 is disposed on the submount 1400*c*. The cylindrical housing 1430 includes a transparent cover 1432, upon which the protrusion 605*b* is disposed. Thus, as shown in FIG. 14D, a gap 1434 exists between the detectors 1410*c* and the protrusion 605*b*. The height of this gap 1434 can be chosen to increase or maximize the amount of light that impinges on the detectors 1410*c*.

The cylindrical housing 1430 can be made of metal, plastic, or another suitable material. The transparent cover 1432 can be fabricated from glass or plastic, among other materials. The cylindrical housing 1430 can be attached to the submount 1400*c* at the same time or substantially the same time as the detectors 1410*c* to reduce manufacturing costs. A shape other than a cylinder can be selected for the housing 1430 in various embodiments.

In certain embodiments, the cylindrical housing 1430 (and transparent cover 1432) forms an airtight or substantially airtight or hermetic seal with the submount 1400*c*. As a result, the cylindrical housing 1430 can protect the detectors 1410*c* and conductors 1412*c* from fluids and vapors that can cause corrosion. Advantageously, in certain embodiments, the cylindrical housing 1430 can protect the detectors 1410*c* and conductors 1412*c* more effectively than currently-available resin epoxies, which are sometimes applied to solder joints between conductors and detectors.

In embodiments where the cylindrical housing 1430 is at least partially made of metal, the cylindrical housing 1430 can provide noise shielding for the detectors 1410*c*. For example, the cylindrical housing 1430 can be soldered to a ground connection or ground plane on the submount 1400*c*, which allows the cylindrical housing 1430 to reduce noise. In another embodiment, the transparent cover 1432 can include a conductive material or conductive layer, such as conductive glass or plastic. The transparent cover 1432 can include any of the features of the noise shields 790 described above.

The protrusion 605*b* includes the chamfered edges 607 described above with respect to FIG. 6E. These chamfered edges 607 can allow a patient to more comfortably slide a finger over the protrusion 605*b* when inserting the finger into the sensor 301*f*.

Figure 14F:
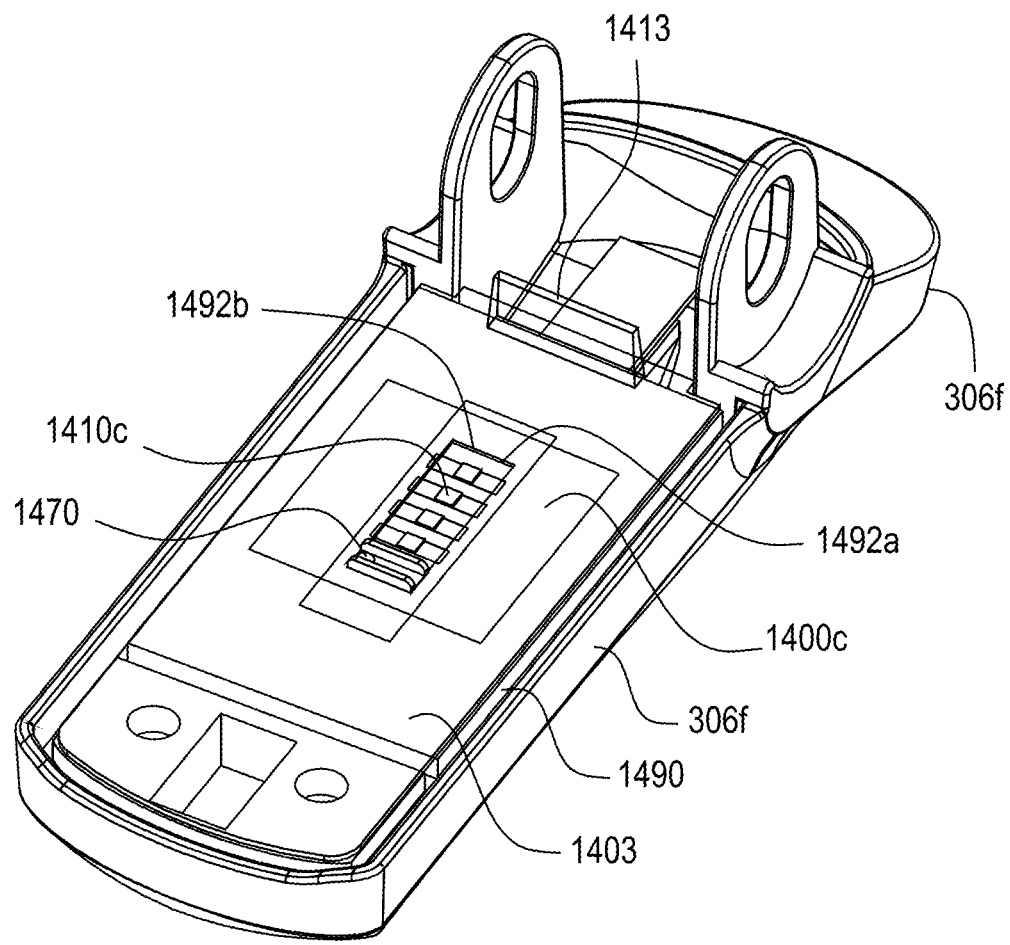
FIGS. 14F through 14H illustrate embodiment of portions of a detector shell.

FIG. 14F illustrates a portion of the detector shell 306*f*, which includes the detectors 1410*c* on the substrate 1400*c*. The substrate 1400*c* is enclosed by a shielding enclosure 1490, which can include the features of the shielding enclosures 790*a*, 790*b* described above (see also FIG. 17). The shielding enclosure 1490 can be made of metal. The shielding enclosure 1490 includes a window 1492*a* above the detectors 1410*c*, which allows light to be transmitted onto the detectors 1410*c*.

A noise shield 1403 is disposed above the shielding enclosure 1490. The noise shield 1403, in the depicted embodiment, includes a window 1492*a* corresponding to the window 1492*a*. Each of the windows 1492*a*, 1492*b* can include glass, plastic, or can be an opening without glass or plastic. In some embodiments, the windows 1492*a*, 1492*b* may be selected to have different sizes or shapes from each other.

The noise shield 1403 can include any of the features of the conductive glass described above. In the depicted embodiment, the noise shield 1403 extends about three-quarters of the length of the detector shell 306*f*. In other embodiments, the noise shield 1403 could be smaller or larger. The noise shield 1403 could, for instance, merely cover the detectors 1410*c*, the submount 1400*c*, or a portion thereof. The noise shield 1403 also includes a stop 1413 for positioning a measurement site within the sensor 301*f*. Advantageously, in certain embodiments, the noise shield 1403 can reduce noise caused by light piping.

A thermistor 1470 is also shown. The thermistor 1470 is attached to the submount 1400*c* and protrudes above the noise shield 1403. As described above, the thermistor 1470 can be employed to measure a temperature of a measurement site. Such a temperature can be helpful in correcting for wavelength drift due to changes in water absorption, which can be temperature dependent, thereby providing more accurate data useful in detecting blood analytes like glucose.

In the depicted embodiment, the detectors 1410*c* are not enclosed in the cylindrical housing 1430. In an alternative embodiment, the cylindrical housing 1430 encloses the detectors 1410*c* and is disposed under the noise shield 1403. In another embodiment, the cylindrical housing 1430 encloses the detectors 1410*c* and the noise shield 1403 is not used. If both the cylindrical housing 1403 and the noise shield 1403 are used, either or both can have noise shielding features.

Figure 14G:
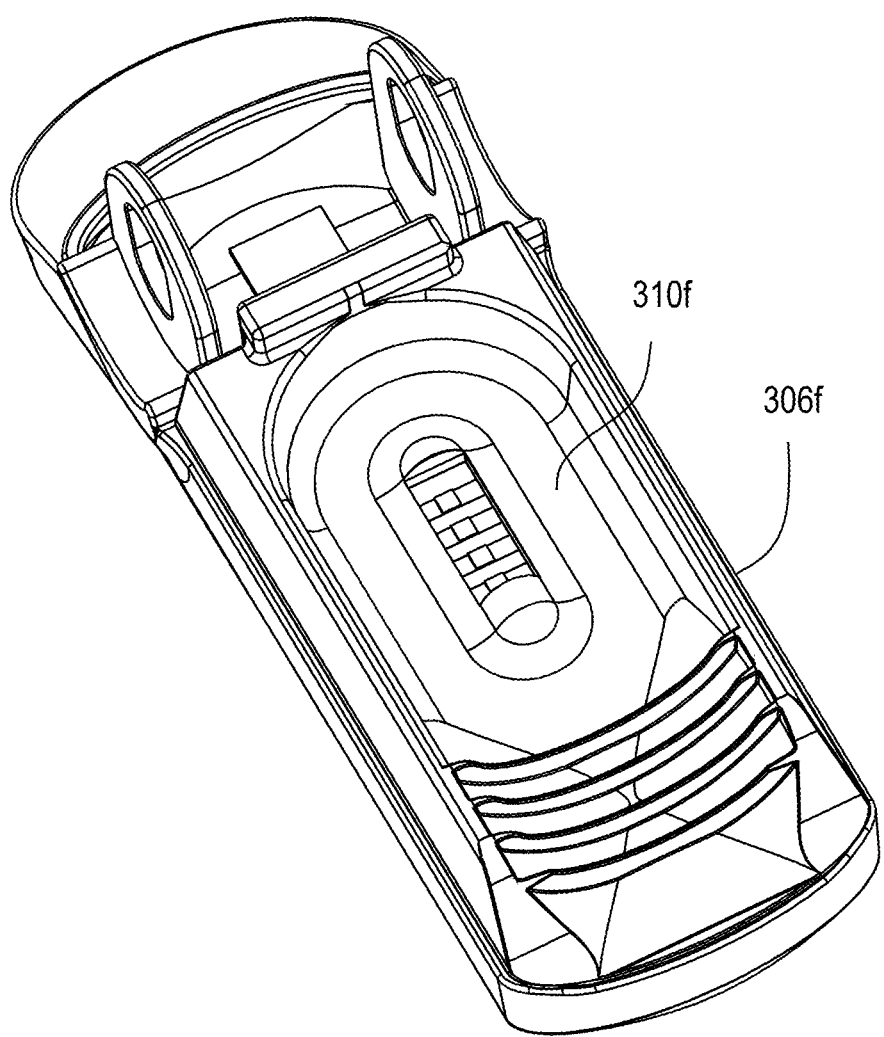
Figure 14H:
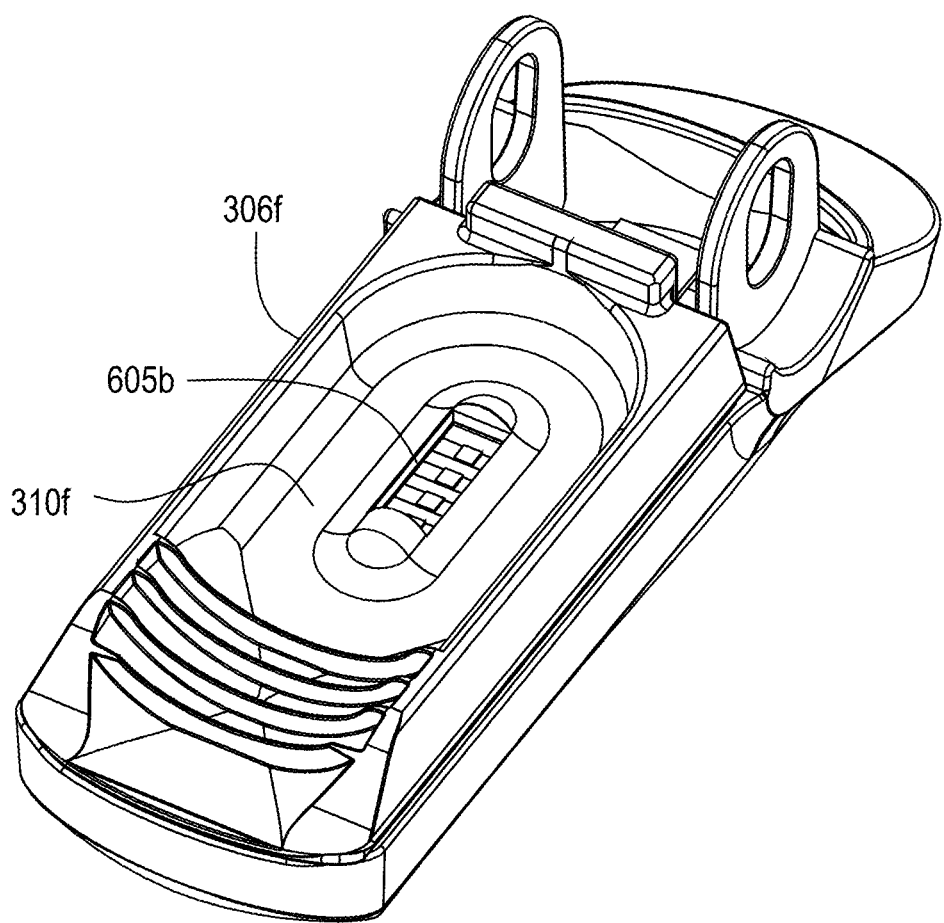

FIG. 14G illustrates the detector shell 306*f* of FIG. 14F, with the finger bed 310*f* disposed thereon. FIG. 14H illustrates the detector shell 306*f* of FIG. 14G, with the protrusion 605*b* disposed in the finger bed 310*f*.

Figure 14I:
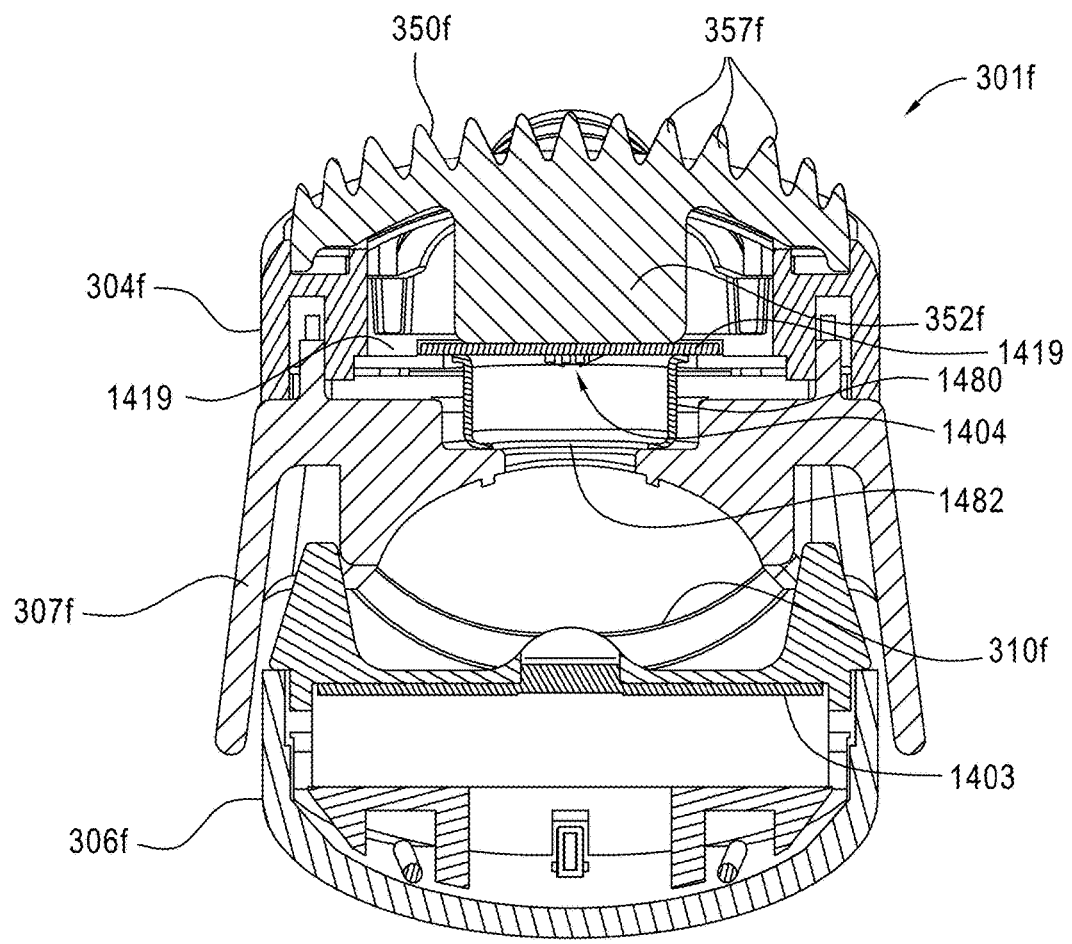
FIG. 14I illustrates a cutaway view of an embodiment of a sensor.

FIG. 14I illustrates a cutaway view of the sensor 301*f*. Not all features of the sensor 301*f* are shown, such as the protrusion 605*b*. Features shown include the emitter and detector shells 304*f*, 306*f*, the flaps 307*f*, the heat sink 350*f* and fins 351*f*, the finger bed 310*f*, and the noise shield 1403.

In addition to these features, emitters 1404 are depicted in the emitter shell 304*f*. The emitters 1404 are disposed on a submount 1401, which is connected to a circuit board 1419. The emitters 1404 are also enclosed within a cylindrical housing 1480. The cylindrical housing 1480 can include all of the features of the cylindrical housing 1430 described above. For example, the cylindrical housing 1480 can be made of metal, can be connected to a ground plane of the submount 1401 to provide noise shielding, and can include a transparent cover 1482.

The cylindrical housing 1480 can also protect the emitters 1404 from fluids and vapors that can cause corrosion. Moreover, the cylindrical housing 1480 can provide a gap between the emitters 1404 and the measurement site (not shown), which can allow light from the emitters 1404 to even out or average out before reaching the measurement site.

The heat sink 350*f*, in addition to including the fins 351*f*, includes a protuberance 352*f* that extends down from the fins 351*f* and contacts the submount 1401. The protuberance 352*f* can be connected to the submount 1401, for example, with thermal paste or the like. The protuberance 352*f* can sink heat from the emitters 1404 and dissipate the heat via the fins 351*f*.

Figure 15A:
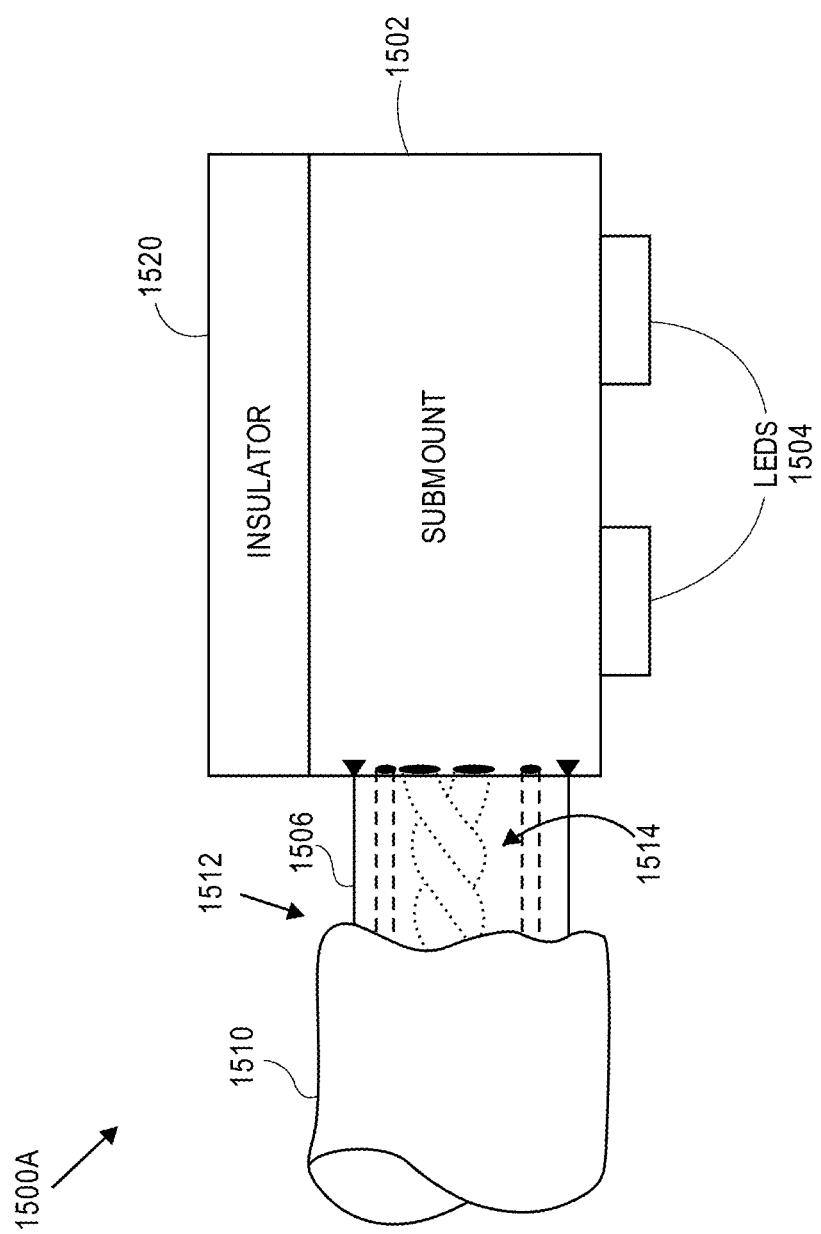
FIGS. 15A through 15F illustrate embodiments of sensors that include heat sink features.
Figure 15B:
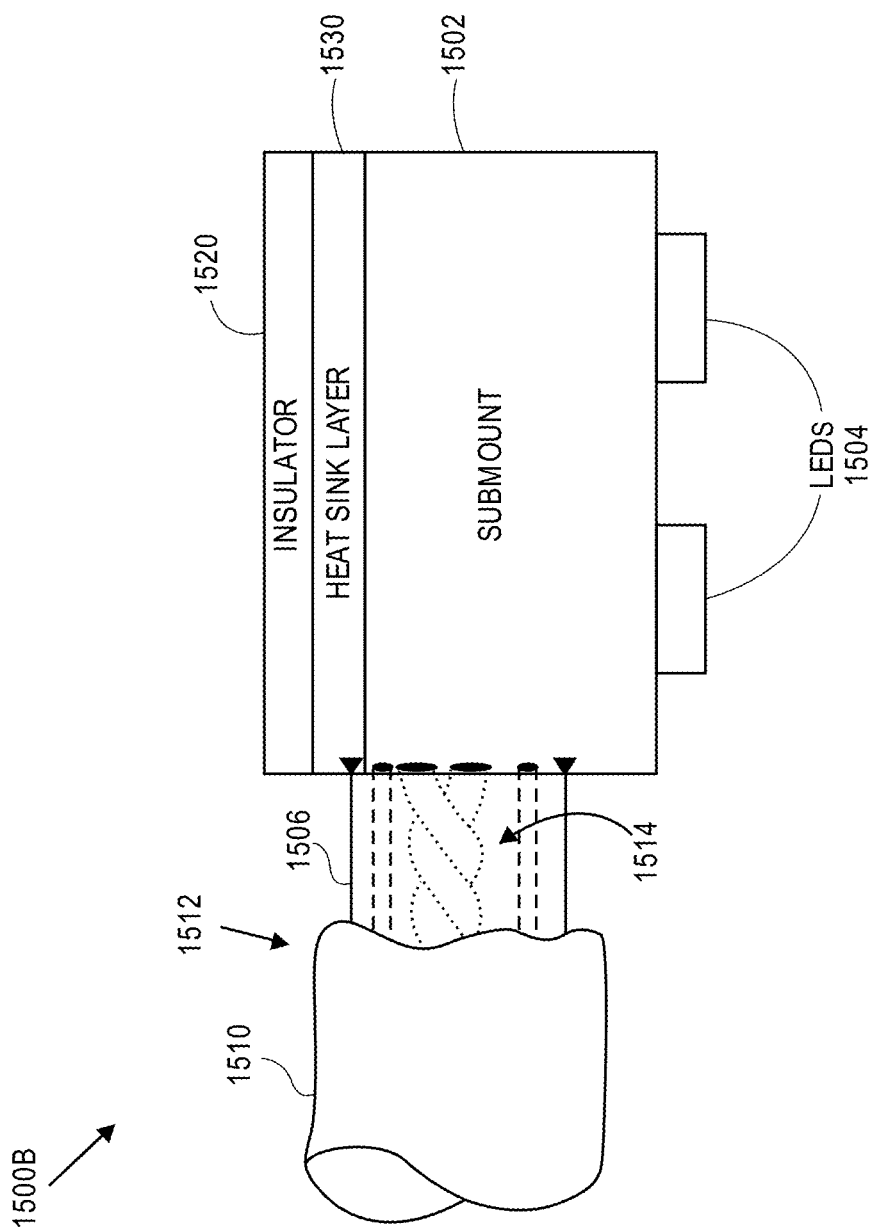

FIGS. 15A and 15B illustrate embodiments of sensor portions 1500A, 1500B that include alternative heat sink features to those described above. These features can be incorporated into any of the sensors described above. For example, any of the sensors above can be modified to use the heat sink features described below instead of or in addition to the heat sink features of the sensors described above.

The sensor portions 1500A, 1500B shown include LED emitters 1504; however, for ease of illustration, the detectors have been omitted. The sensor portions 1500A, 1500B shown can be included, for example, in any of the emitter shells described above.

The LEDs 1504 of the sensor portions 1500A, 1500B are connected to a substrate or submount 1502. The submount 1502 can be used in place of any of the submounts described above. The submount 1502 can be a non-electrically conducting material made of any of a variety of materials, such as ceramic, glass, or the like. A cable 1512 is attached to the submount 1502 and includes electrical wiring 1514, such as twisted wires and the like, for communicating with the LEDs 1504. The cable 1512 can correspond to the cables 212 described above.

Although not shown, the cable 1512 can also include electrical connections to a detector. Only a portion of the cable 1512 is shown for clarity. The depicted embodiment of the cable 1512 includes an outer jacket 1510 and a conductive shield 1506 disposed within the outer jacket 1510. The conductive shield 1506 can be a ground shield or the like that is made of a metal such as braided copper or aluminum. The conductive shield 1506 or a portion of the conductive shield 1506 can be electrically connected to the submount 1502 and can reduce noise in the signal generated by the sensor 1500A, 1500B by reducing RF coupling with the wires 1514. In alternative embodiments, the cable 1512 does not have a conductive shield. For example, the cable 1512 could be a twisted pair cable or the like, with one wire of the twisted pair used as a heat sink.

Referring specifically to FIG. 15A, in certain embodiments, the conductive shield 1506 can act as a heat sink for the LEDs 1504 by absorbing thermal energy from the LEDs 1504 and/or the submount 1502. An optional heat insulator 1520 in communication with the submount 1502 can also assist with directing heat toward the conductive shield 1506. The heat insulator 1520 can be made of plastic or another suitable material. Advantageously, using the conductive shield 1506 in the cable 1512 as a heat sink can, in certain embodiments, reduce cost for the sensor.

Referring to FIG. 15B, the conductive shield 1506 can be attached to both the submount 1502 and to a heat sink layer 1530 sandwiched between the submount 1502 and the optional insulator 1520. Together, the heat sink layer 1530 and the conductive shield 1506 in the cable 1512 can absorb at least part of the thermal energy from the LEDs and/or the submount 1502.

Figure 15C:
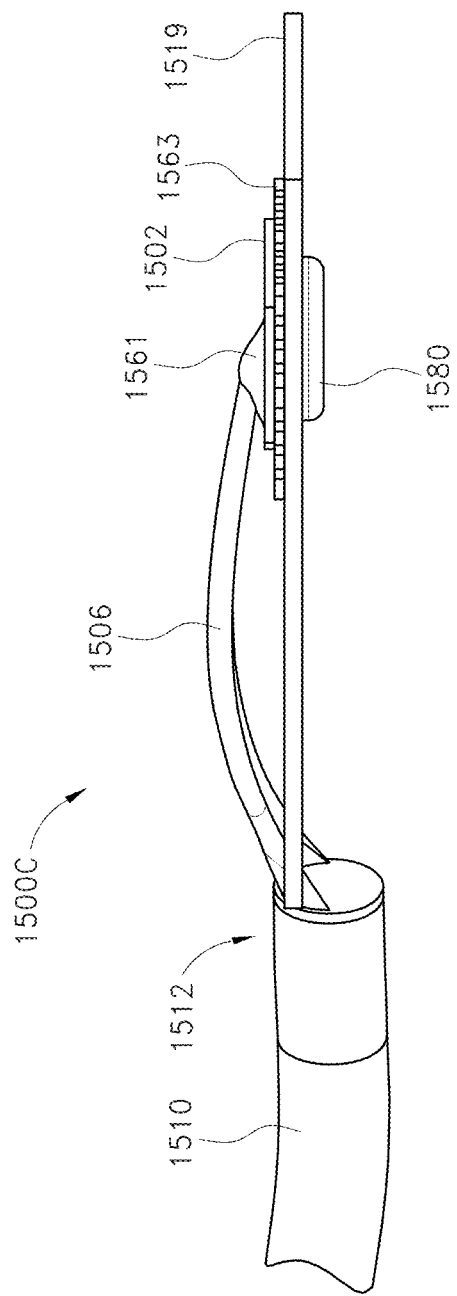
Figure 15D:
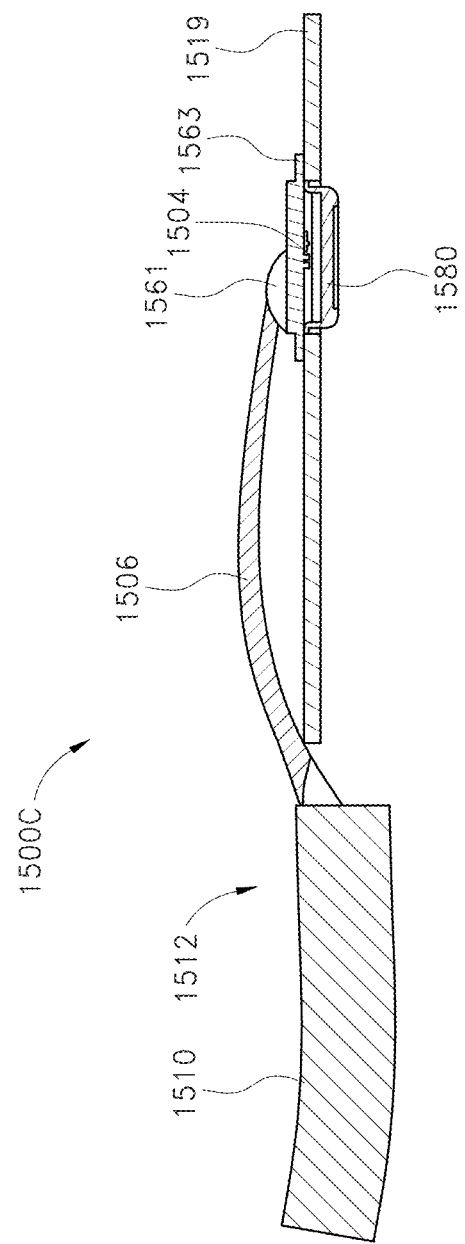

FIGS. 15C and 15D illustrate implementations of a sensor portion 1500C that includes the heat sink features of the sensor portion 1500A described above with respect to FIG. 15A. The sensor portion 1500C includes the features of the sensor portion 1500A, except that the optional insulator 1520 is not shown. FIG. 15D is a side cutaway view of the sensor portion 1500C that shows the emitters 1504.

The cable 1512 includes the outer jacket 1510 and the conductive shield 1506. The conductive shield 1506 is soldered to the submount 1502, and the solder joint 1561 is shown. In some embodiments, a larger solder joint 1561 can assist with removing heat more rapidly from the emitters 1504. Various connections 1563 between the submount 1502 and a circuit board 1519 are shown. In addition, a cylindrical housing 1580, corresponding to the cylindrical housing 1480 of FIG. 14I, is shown protruding through the circuit board 1519. The emitters 1504 are enclosed in the cylindrical housing 1580.

Figure 15E:
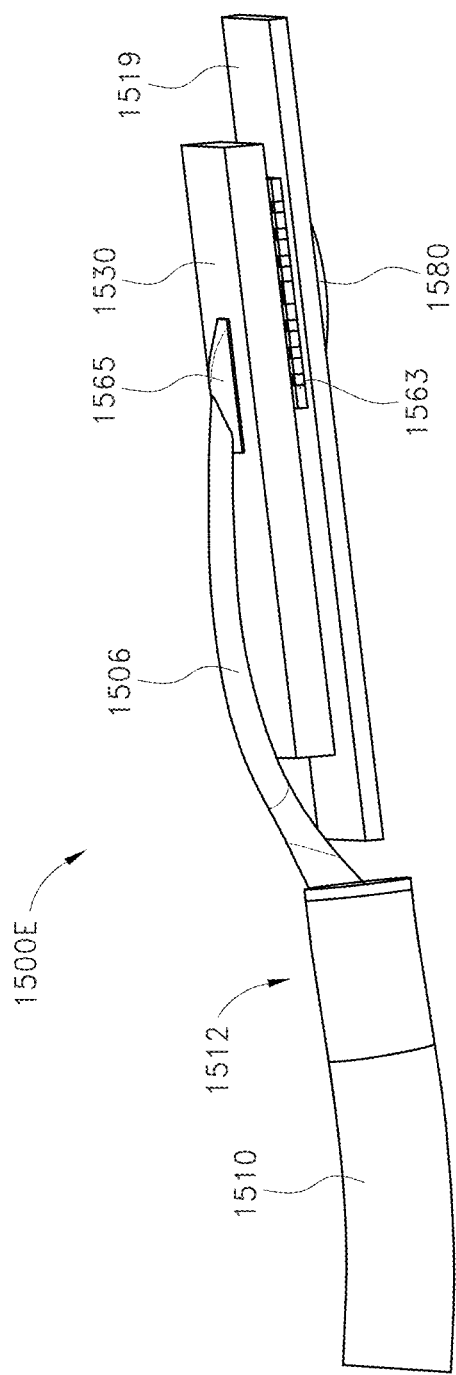
Figure 15F:
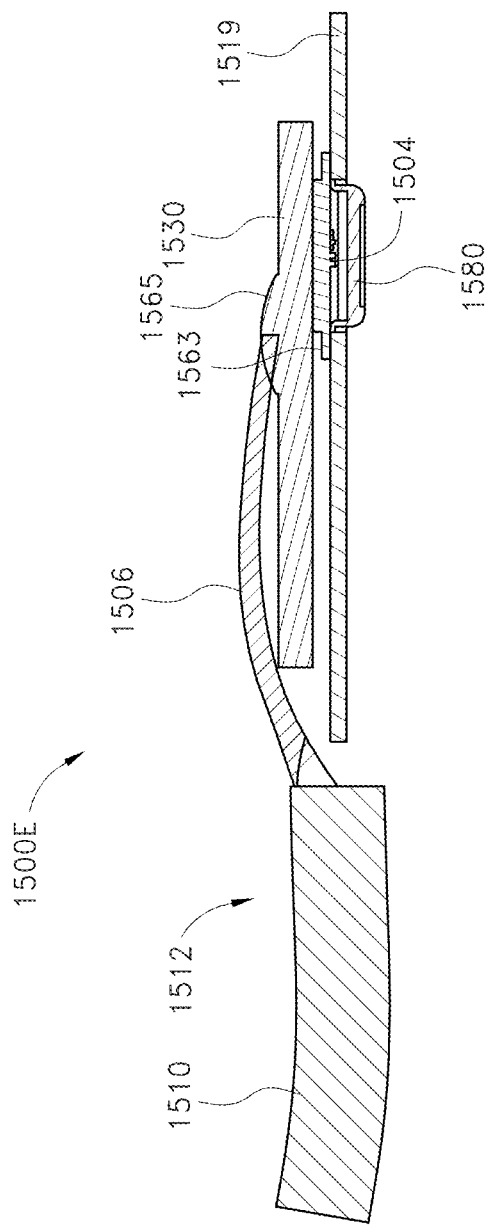

FIGS. 15E and 15F illustrate implementations of a sensor portion 1500E that includes the heat sink features of the sensor portion 1500B described above with respect to FIG. 15B. The sensor portion 1500E includes the heat sink layer 1530. The heat sink layer 1530 can be a metal plate, such as a copper plate or the like. The optional insulator 1520 is not shown. FIG. 15F is a side cutaway view of the sensor portion 1500E that shows the emitters 1504.

In the depicted embodiment, the conductive shield 1506 of the cable 1512 is soldered to the heat sink layer 1530 instead of the submount 1502. The solder joint 1565 is shown. In some embodiments, a larger solder joint 1565 can assist with removing heat more rapidly from the emitters 1504. Various connections 1563 between the submount 1502 and a circuit board 1519 are shown. In addition, the cylindrical housing 1580 is shown protruding through the circuit board 1519. The emitters 1504 are enclosed in the cylindrical housing 1580.

Figure 15G:
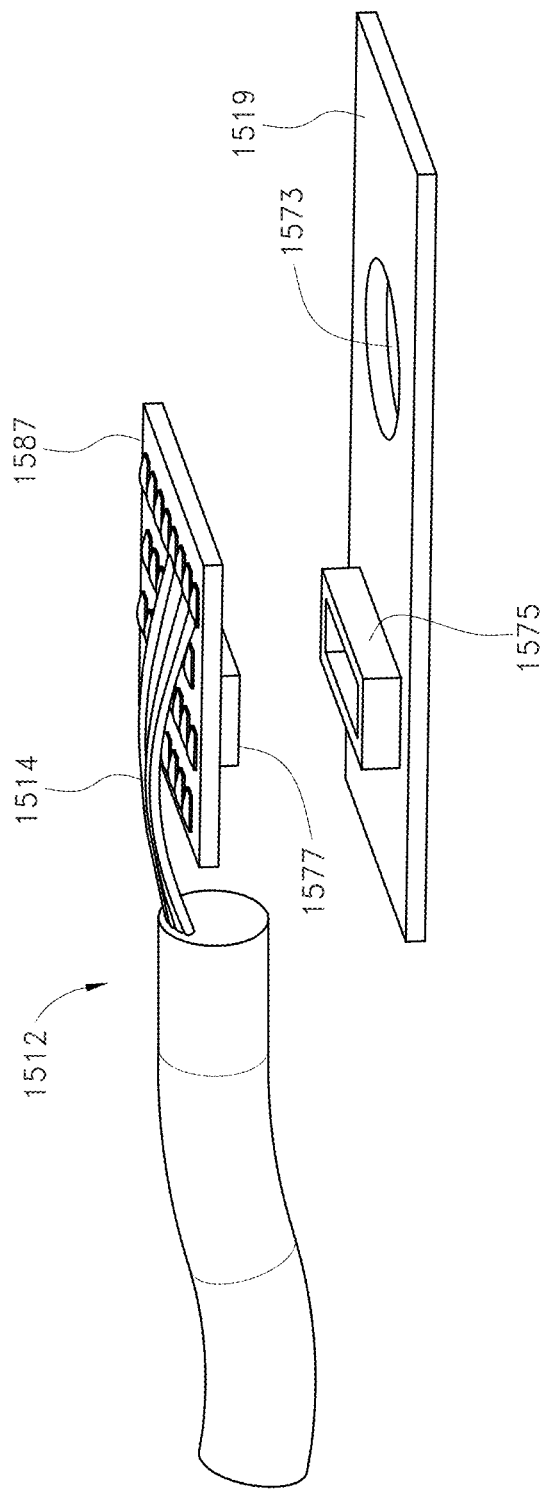

FIGS. 15G and 15H illustrate embodiments of connector features that can be used with any of the sensors described above with respect to FIGS. 1 through 15F. Referring to FIG. 15G, the circuit board 1519 includes a female connector 1575 that mates with a male connector 1577 connected to a daughter board 1587. The daughter board 1587 includes connections to the electrical wiring 1514 of the cable 1512. The connected boards 1519, 1587 are shown in FIG. 15H. Also shown is a hole 1573 that can receive the cylindrical housing 1580 described above.

Advantageously, in certain embodiments, using a daughter board 1587 to connect to the circuit board 1519 can enable connections to be made more easily to the circuit board 1519. In addition, using separate boards can be easier to manufacture than a single circuit board 1519 with all connections soldered to the circuit board 1519.

Figure 15I:
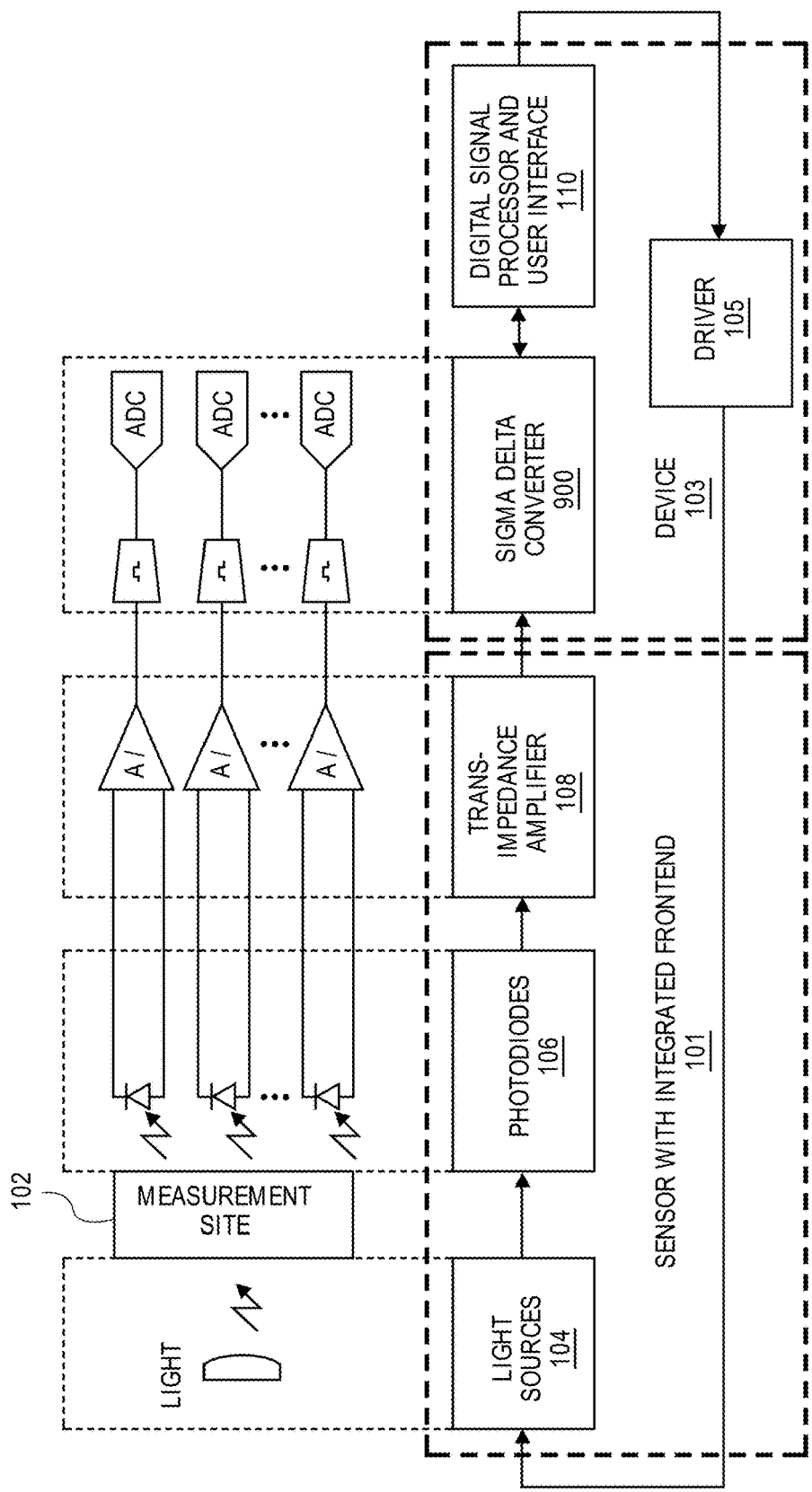
FIG. 15I illustrates an exemplary architecture for a transimpedance-based front-end that may be employed in any of the sensors described herein.

FIG. 15I illustrates an exemplary architecture for front-end interface 108 as a transimpedance-based front-end. As noted, front-end interfaces 108 provide an interface that adapts the output of detectors 106 into a form that can be handled by signal processor 110. As shown in this figure, sensor 101 and front-end interfaces 108 may be integrated together as a single component, such as an integrated circuit. Of course, one skilled in the art will recognize that sensor 101 and front end interfaces 108 may comprise multiple components or circuits that are coupled together.

Front-end interfaces 108 may be implemented using transimpedance amplifiers that are coupled to analog to digital converters in a sigma delta converter. In some embodiments, a programmable gain amplifier (PGA) can be used in combination with the transimpedance-based front-ends. For example, the output of a transimpedance-based front-end may be output to a sigma-delta ADC that comprises a PGA. A PGA may be useful in order to provide another level of amplification and control of the stream of signals from detectors 106. The PGA may be an integrated circuit or built from a set of micro-relays. Alternatively, the PGA and ADC components in converter 900 may be integrated with the transimpedance-based front-end in sensor 101.

Due to the low-noise requirements for measuring blood analytes like glucose and the challenge of using multiple photodiodes in detector 106, the applicants developed a noise model to assist in configuring front-end 108. Conventionally, those skilled in the art have focused on optimizing the impedance of the transimpedance amplifiers to minimize noise.

However, the following noise model was discovered by the applicants:

$$\text{Noise} = \sqrt{aR + bR^2}, \text{ where:}$$

aR is characteristic of the impedance of the transimpedance amplifier; and $bR^2$ is characteristic of the impedance of the photodiodes in detector and the number of photodiodes in detector 106.

The foregoing noise model was found to be helpful at least in part due to the high SNR required to measure analytes like glucose. However, the foregoing noise model was not previously recognized by artisans at least in part because, in conventional devices, the major contributor to noise was generally believed to originate from the emitter or the LEDs. Therefore, artisans have generally continued to focus on reducing noise at the emitter.

However, for analytes like glucose, the discovered noise model revealed that one of the major contributors to noise was generated by the photodiodes. In addition, the amount of noise varied based on the number of photodiodes coupled to a transimpedance amplifier. Accordingly, combinations of various photodiodes from different manufacturers, different impedance values with the transimpedance amplifiers, and different numbers of photodiodes were tested as possible embodiments.

In some embodiments, different combinations of transimpedance to photodiodes may be used. For example, detectors 1-4 (as shown, e.g., in FIG. 12A) may each comprise four photodiodes. In some embodiments, each detector of four photodiodes may be coupled to one or more transimpedance amplifiers. The configuration of these amplifiers may be set according to the model shown in FIG. 15J.

Alternatively, each of the photodiodes may be coupled to its own respective transimpedance amplifier. For example, transimpedance amplifiers may be implemented as integrated circuits on the same circuit board as detectors 1-4. In this embodiment, the transimpedance amplifiers may be grouped into an averaging (or summing) circuit, which are known to those skilled in the art, in order to provide an output stream from the detector. The use of a summing amplifier to combine outputs from several transimpedance amplifiers into a single, analog signal may be helpful in improving the SNR relative to what is obtainable from a single transimpedance amplifier. The configuration of the transimpedance amplifiers in this setting may also be set according to the model shown in FIG. 15J.

As yet another alternative, as noted above with respect to FIGS. 12E through 12H, the photodiodes in detectors 106 may comprise multiple active areas that are grouped together. In some embodiments, each of these active areas may be provided its own respective transimpedance. This form of pairing may allow a transimpedance amplifier to be better matched to the characteristics of its corresponding photodiode or active area of a photodiode.

Figure 15J:
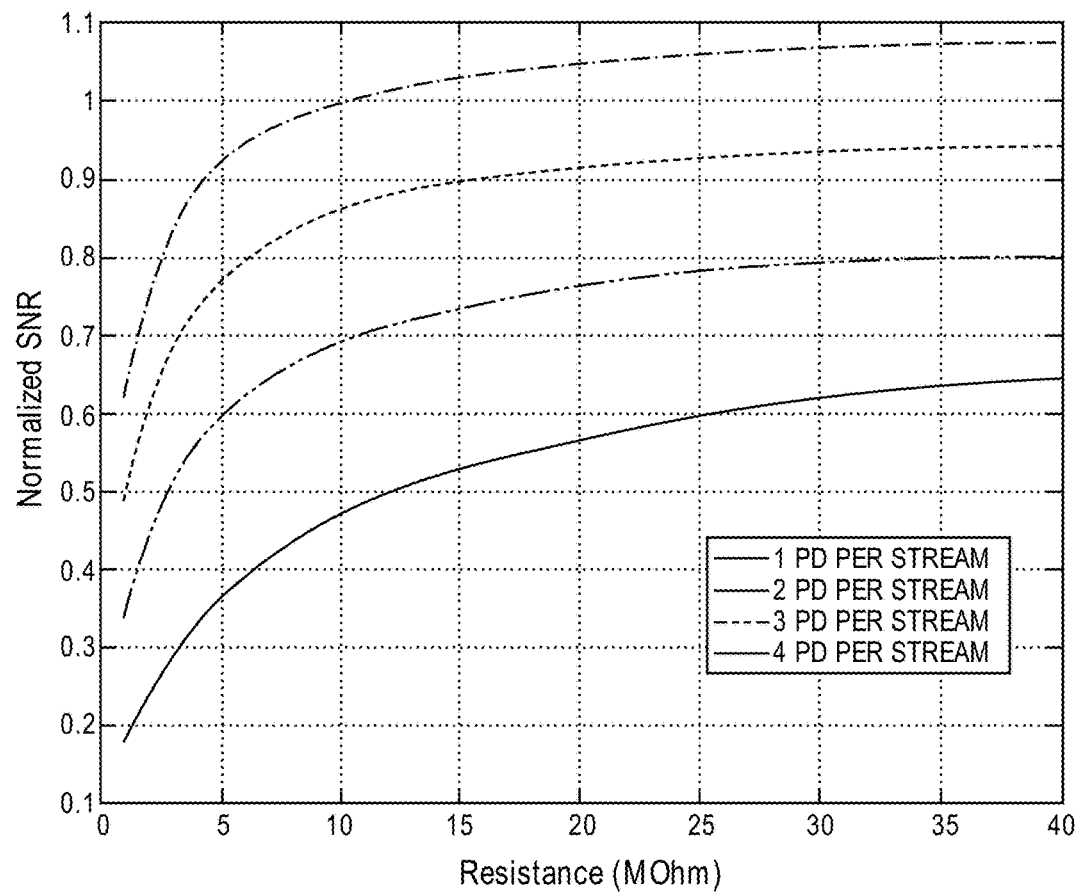
FIG. 15J illustrates an exemplary noise model for configuring the transimpedance-based front-ends shown in FIG. 15I.
Figure 15J:
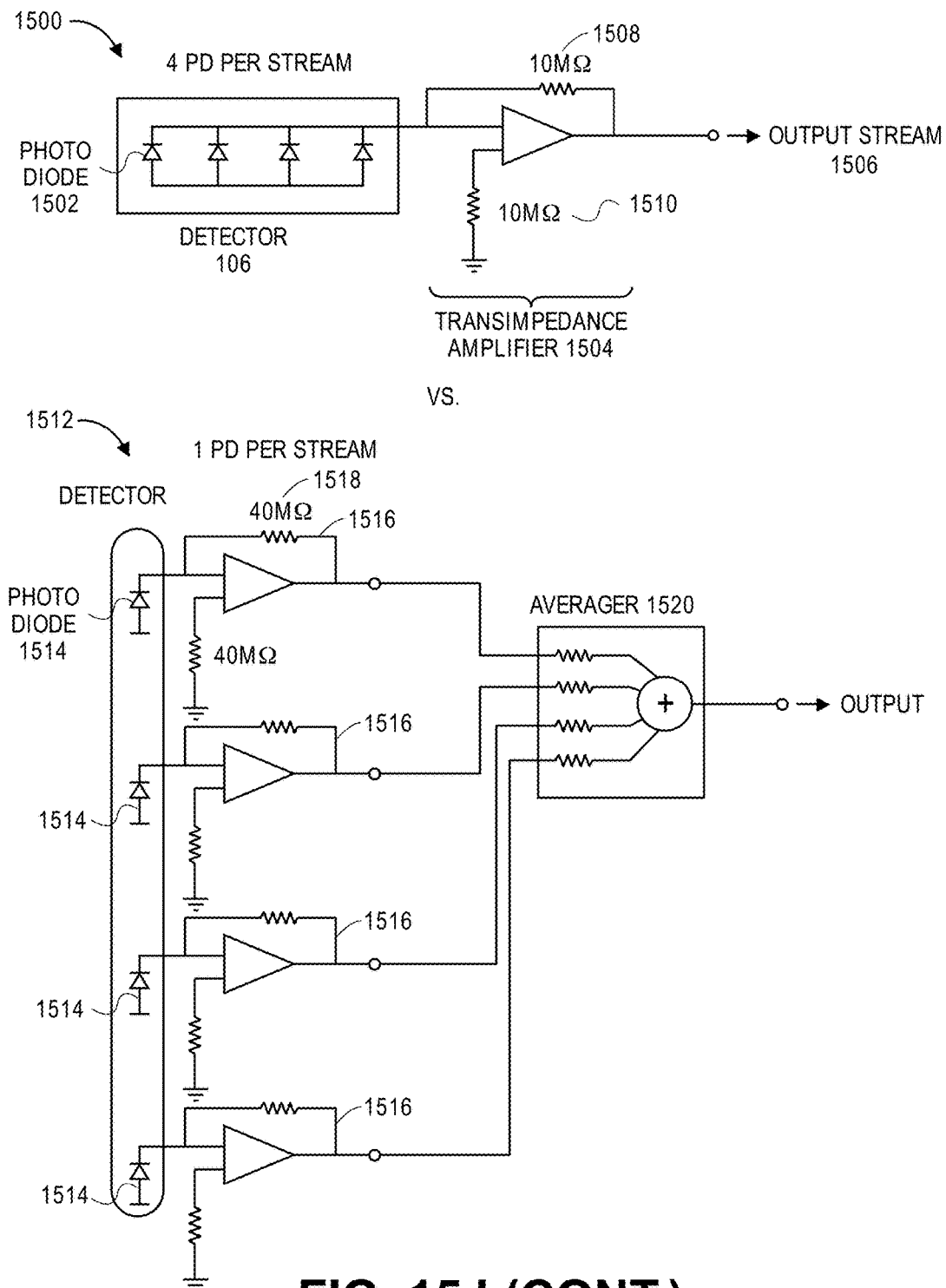

As noted, FIG. 15J illustrates an exemplary noise model that may be useful in configuring transimpedance amplifiers. As shown, for a given number of photodiodes and a desired SNR, an optimal impedance value for a transimpedance amplifier could be determined.

For example, an exemplary "4 PD per stream" sensor 1502 is shown where detector 106 comprises four photodiodes 1502. The photodiodes 1502 are coupled to a single transimpedance amplifier 1504 to produce an output stream 1506. In this example, the transimpedance amplifier comprises 10 MO resistors 1508 and 1510. Thus, output stream 1506 is produced from the four photodiodes (PD) 1502. As shown in the graph of FIG. 15J, the model indicates that resistance values of about 10 MO may provide an acceptable SNR for analytes like glucose.

However, as a comparison, an exemplary "1 PD per stream" sensor 1512 is also shown in FIG. 15J. In particular, sensor 1512 may comprise a plurality of detectors 106 that each comprises a single photodiode 1514. In addition, as shown for this example configuration, each of photodiodes 1514 may be coupled to respective transimpedance amplifiers 1516, e.g., 1 PD per stream. Transimpedance amplifiers are shown having 40 MO resistors 1518. As also shown in the graph of FIG. 15J, the model illustrates that resistance values of 40 MO for resistors 1518 may serve as an alternative to the 4 photodiode per stream architecture of sensor 1502 described above and yet still provide an equivalent SNR.

Moreover, the discovered noise model also indicates that utilizing a 1 photodiode per stream architecture like that in sensor 1512 may provide enhanced performance because each of transimpedance amplifiers 1516 can be tuned or optimized to its respective photodiodes 1518. In some embodiments, an averaging component 1520 may also be used to help cancel or reduce noise across photodiodes 1518.

Figure 15K:
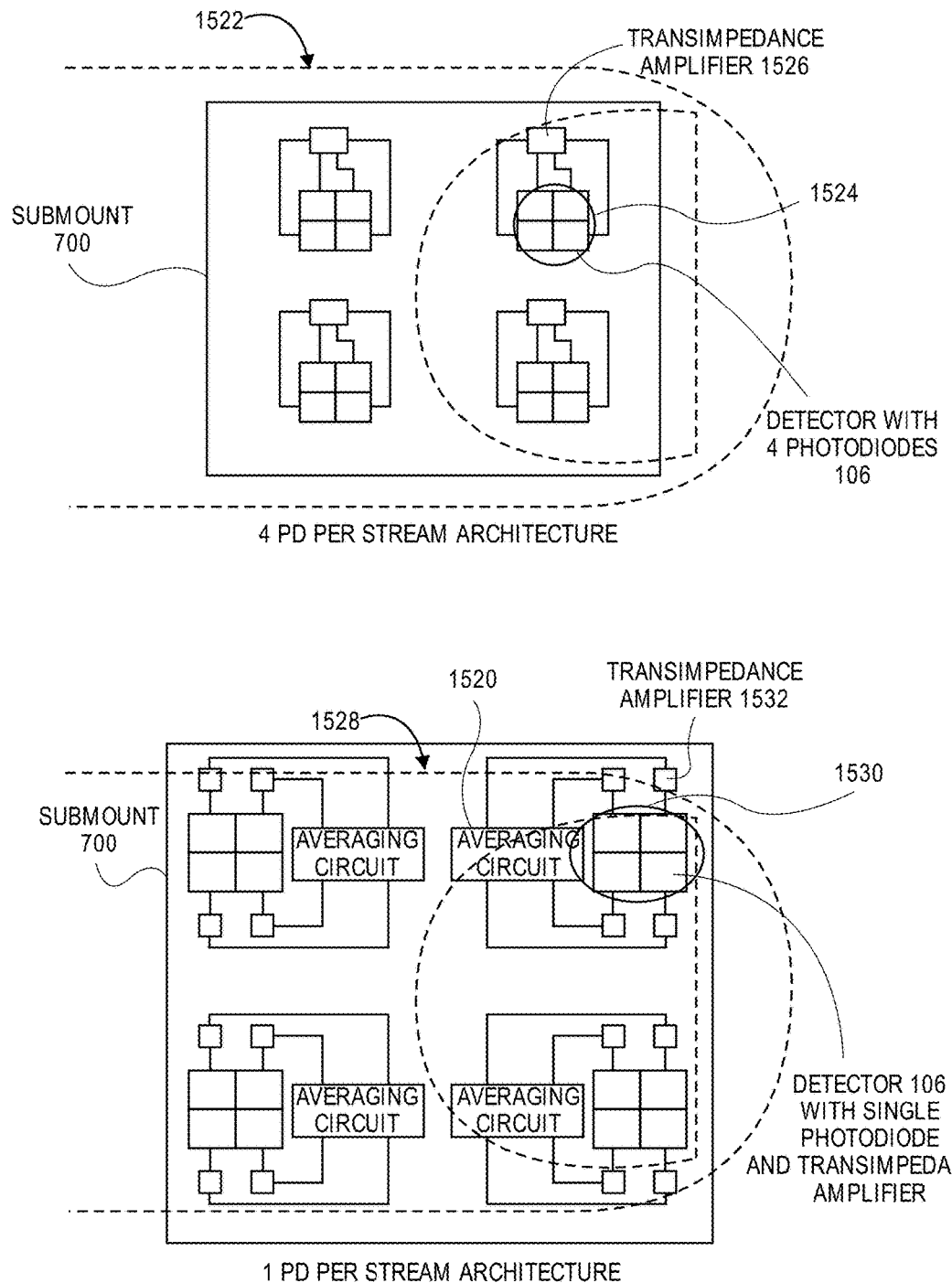
FIG. 15K shows different architectures and layouts for various embodiments of a sensor and its detectors.
Figure 15K:
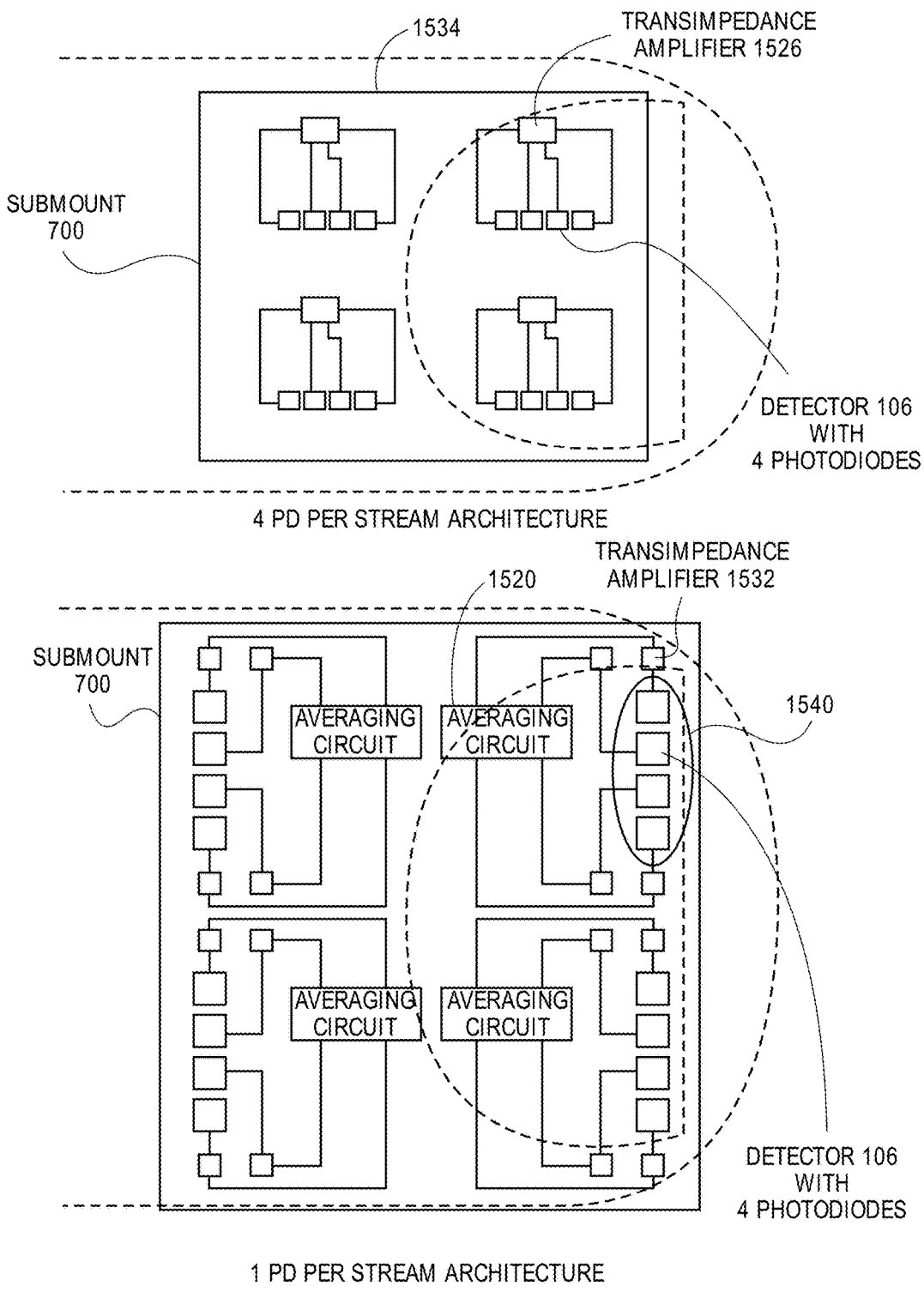
Figure 15K:
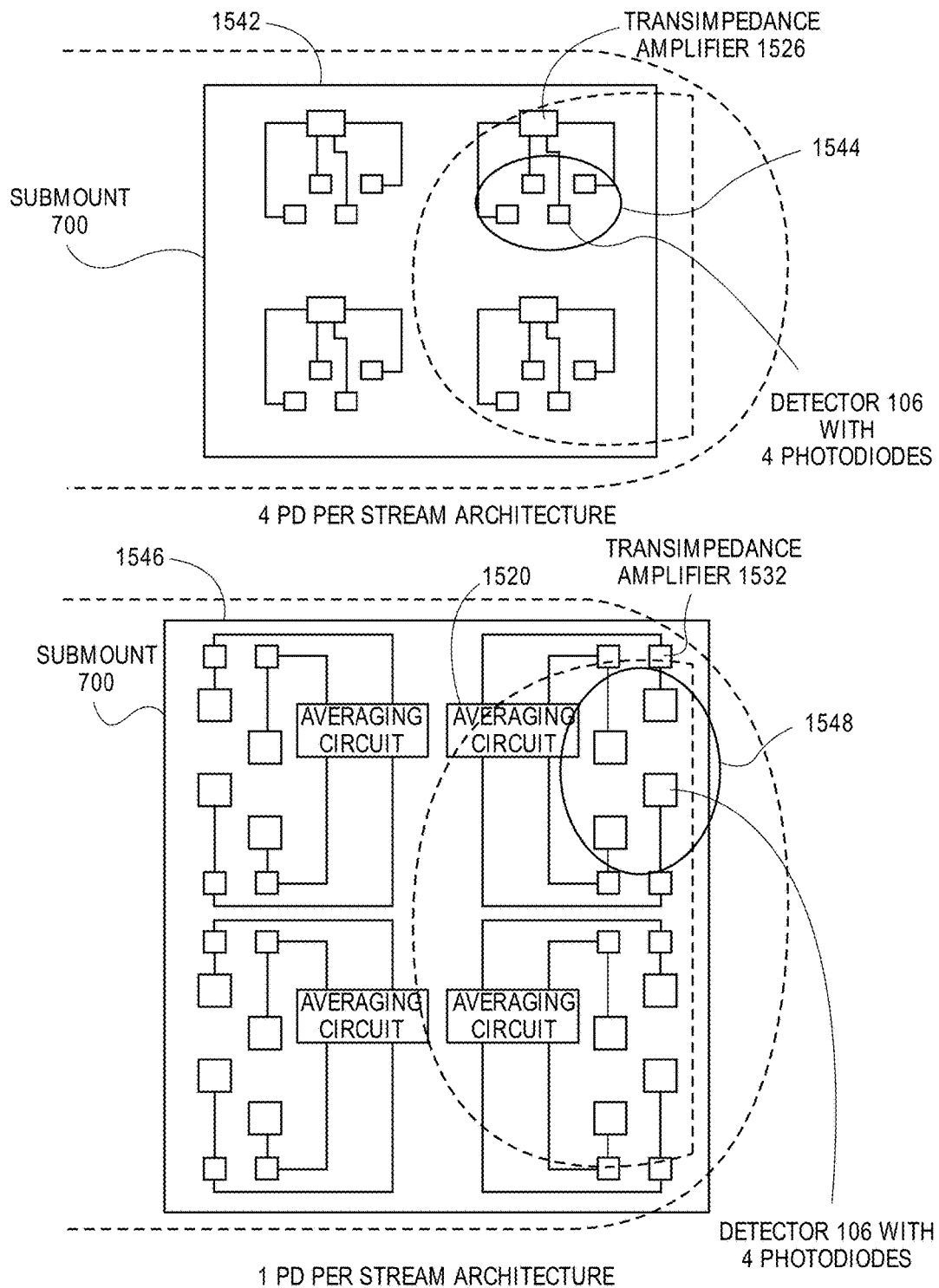

For purposes of illustration, FIG. 15K shows different architectures (e.g., four PD per stream and one PD per stream) for various embodiments of a sensor and how components of the sensor may be laid out on a circuit board or substrate. For example, sensor 1522 may comprise a "4 PD per stream" architecture on a submount 700 in which each detector 106 comprises four (4) photodiodes 1524. As shown for sensor 1522, the output of each set of four photodiodes 1524 is then aggregated into a single transimpedance amplifier 1526 to produce a signal.

As another example, a sensor 1528 may comprise a "1 PD per stream" architecture on submount 700 in which each detector 106 comprises four (4) photodiodes 1530. In sensor 1528, each individual photodiode 1530 is coupled to a respective transimpedance amplifier 1532. The output of the amplifiers 1532 may then be aggregated into averaging circuit 1520 to produce a signal.

As noted previously, one skilled in the art will recognize that the photodiodes and detectors may be arranged in different fashions to optimize the detected light. For example, sensor 1534 illustrates an exemplary "4 PD per stream" sensor in which the detectors 106 comprise photodiodes 1536 arranged in a linear fashion. Likewise, sensor 1538 illustrates an exemplary "1 PD per stream" sensor in which the detectors comprise photodiodes 1540 arranged in a linear fashion.

Alternatively, sensor 1542 illustrates an exemplary "4 PD per stream" sensor in which the detectors 106 comprise photodiodes 1544 arranged in a two-dimensional pattern, such as a zig-zag pattern. Sensor 1546 illustrates an exemplary "1 PD per stream" sensor in which the detectors comprise photodiodes 1548 also arranged in a zig-zag pattern.

Figure 15L:
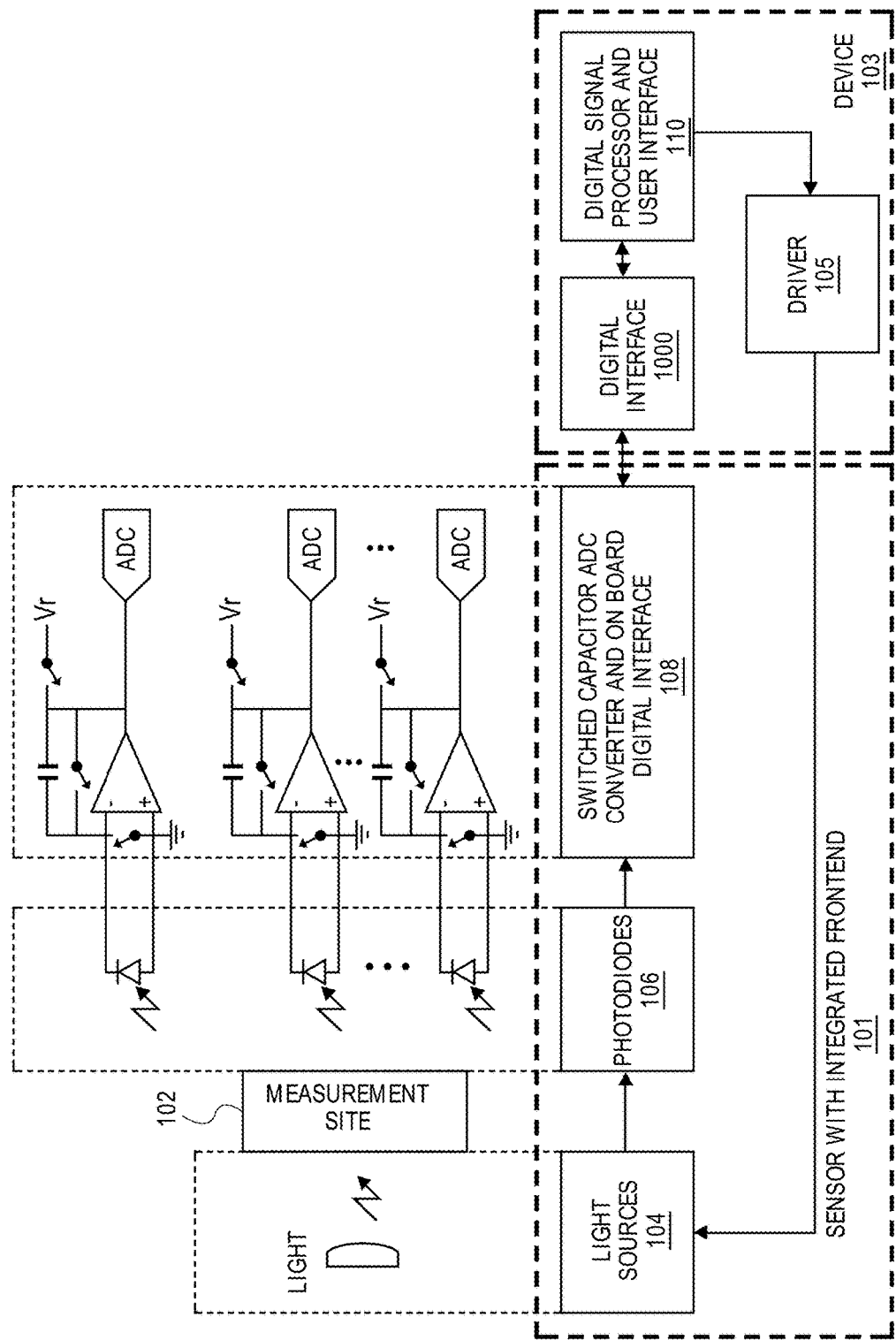
FIG. 15L illustrates an exemplary architecture for a switched-capacitor-based front-end that may be employed in any of the sensors described herein.

FIG. 15L illustrates an exemplary architecture for a switched-capacitor-based front-end. As shown, front-end interfaces 108 may be implemented using switched capacitor circuits and any number of front-end interfaces 108 may be implemented. The output of these switched capacitor circuits may then be provided to a digital interface 1000 and signal processor 110. Switched capacitor circuits may be useful in system 100 for their resistor free design and analog averaging properties. In particular, the switched capacitor circuitry provides for analog averaging of the signal that allows for a lower smaller sampling rate (e.g., 2 KHz sampling for analog versus 48 KHz sampling for digital designs) than similar digital designs. In some embodiments, the switched capacitor architecture in front end interfaces 108 may provide a similar or equivalent SNR to other front end designs, such as a sigma delta architecture. In addition, a switched capacitor design in front end interfaces 108 may require less computational power by signal processor 110 to perform the same amount of decimation to obtain the same SNR.

FIGS. 16A and 16B illustrate embodiments of disposable optical sensors 1600. In an embodiment, any of the features described above, such as protrusion, shielding, and/or heat sink features, can be incorporated into the disposable sensors 1600 shown. For instance, the sensors 1600 can be used as the sensors 101 in the system 100 described above with respect to FIG. 1. Moreover, any of the features described above, such as protrusion, shielding, and/or heat sink features, can be implemented in other disposable sensor designs that are not depicted herein.

The sensors 1600 include an adult/pediatric sensor 1610 for finger placement and a disposable infant/neonate sensor 1602 configured for toe, foot or hand placement. Each sensor 1600 has a tape end 1610 and an opposite connector end 1620 electrically and mechanically interconnected via a flexible coupling 1630. The tape end 1610 attaches an emitter and detector to a tissue site. Although not shown, the tape end 1610 can also include any of the protrusion, shielding, and/or heat sink features described above. The emitter illuminates the tissue site and the detector generates a sensor signal responsive to the light after tissue absorption, such as absorption by pulsatile arterial blood flow within the tissue site.

The sensor signal is communicated via the flexible coupling 1630 to the connector end 1620. The connector end 1620 can mate with a cable (not shown) that communicates the sensor signal to a monitor (not shown), such as any of the cables or monitors shown above with respect to FIGS. 2A through 2D. Alternatively, the connector end 1620 can mate directly with the monitor.

Figure 17:
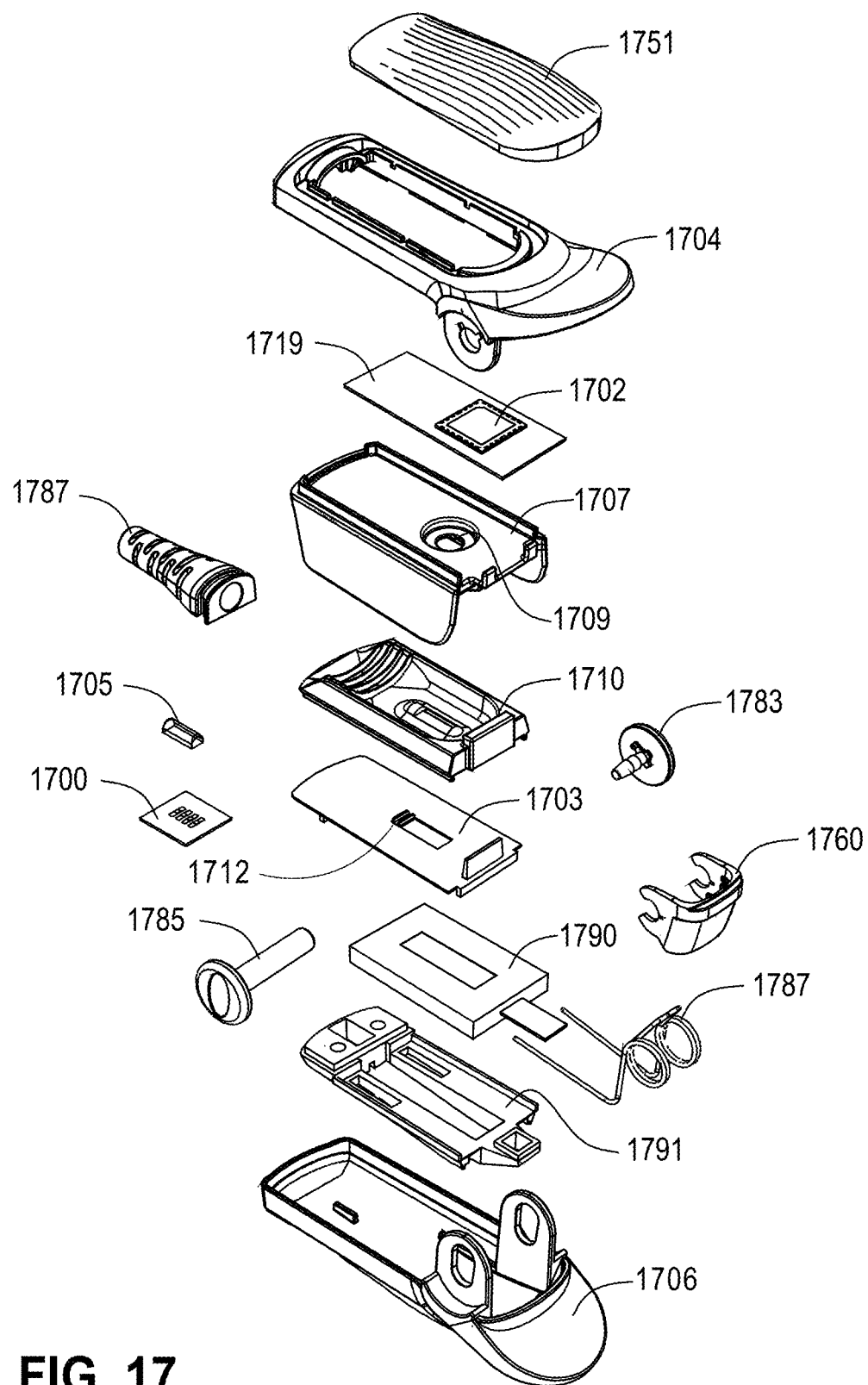
FIG. 17 illustrates an exploded view of certain components of an example sensor.

FIG. 17 illustrates an exploded view of certain of the components of the sensor 301f described above. A heat sink 1751 and a cable 1781 attach to an emitter shell 1704. The emitter shell attaches to a flap housing 1707. The flap housing 1707 includes a receptacle 1709 to receive a cylindrical housing 1480/1580 (not shown) attached to an emitter submount 1702, which is attached to a circuit board 1719.

A spring 1787 attaches to a detector shell 1706 via pins 1783, 1785, which hold the emitter and detector shells 1704, 1706 together. A support structure 1791 attaches to the detector shell 1706, which provides support for a shielding enclosure 1790. A noise shield 1713 attaches to the shielding enclosure 1790. A detector submount 1700 is disposed inside the shielding enclosure 1790. A finger bed 1710 provides a surface for placement of the patient's finger. Finger bed 1710 may comprise a gripping surface or gripping features, which may assist in placing and stabilizing a patient's finger in the sensor. A partially cylindrical protrusion 1705 may also be disposed in the finger bed 1710. As shown, finger bed 1710 attaches to the noise shield 1703. The noise shield 1703 may be configured to reduce noise, such as from ambient light and electromagnetic noise. For example, the noise shield 1703 may be constructed from materials having an opaque color, such as black or a dark blue, to prevent light piping.

Noise shield 1703 may also comprise a thermistor 1712. The thermistor 1712 may be helpful in measuring the temperature of a patient's finger. For example, the thermistor 1712 may be useful in detecting when the patient's finger is reaching an unsafe temperature that is too hot or too cold. In addition, the temperature of the patient's finger may be useful in indicating to the sensor the presence of low perfusion as the temperature drops. In addition, the thermistor 1712 may be useful in detecting a shift in the characteristics of the water spectrum in the patient's finger, which can be temperature dependent.

Moreover, a flex circuit cover 1706 attaches to the pins 1783, 1785. Although not shown, a flex circuit can also be provided that connects the circuit board 1719 with the submount 1700 (or a circuit board to which the submount 1700 is connected). A flex circuit protector 1760 may be provided to provide a barrier or shield to the flex circuit (not shown). In particular, the flex circuit protector 1760 may also prevent any electrostatic discharge to or from the flex circuit. The flex circuit protector 1760 may be constructed from well known materials, such as a plastic or rubber materials.

Figure 18:
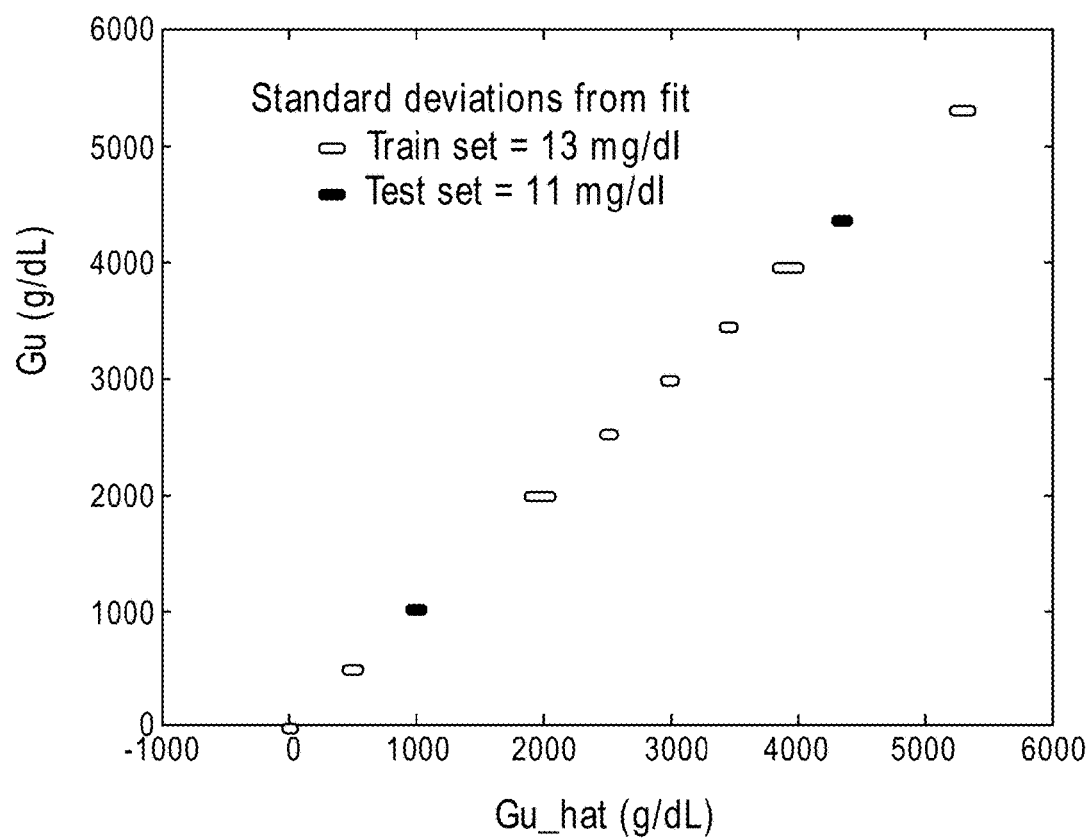
FIGS. 18 through 22 illustrate various results obtained by an exemplary sensor of the disclosure.

FIG. 18 shows the results obtained by an exemplary sensor 101 of the present disclosure that was configured for measuring glucose. This sensor 101 was tested using a pure water ex-vivo sample. In particular, ten samples were prepared that ranged from 0-55 mg/dL. Two samples were used as a training set and eight samples were then used as a test population. As shown, embodiments of the sensor 101 were able to obtain at least a standard deviation of 13 mg/dL in the training set and 11 mg/dL in the test population.

Figure 19:
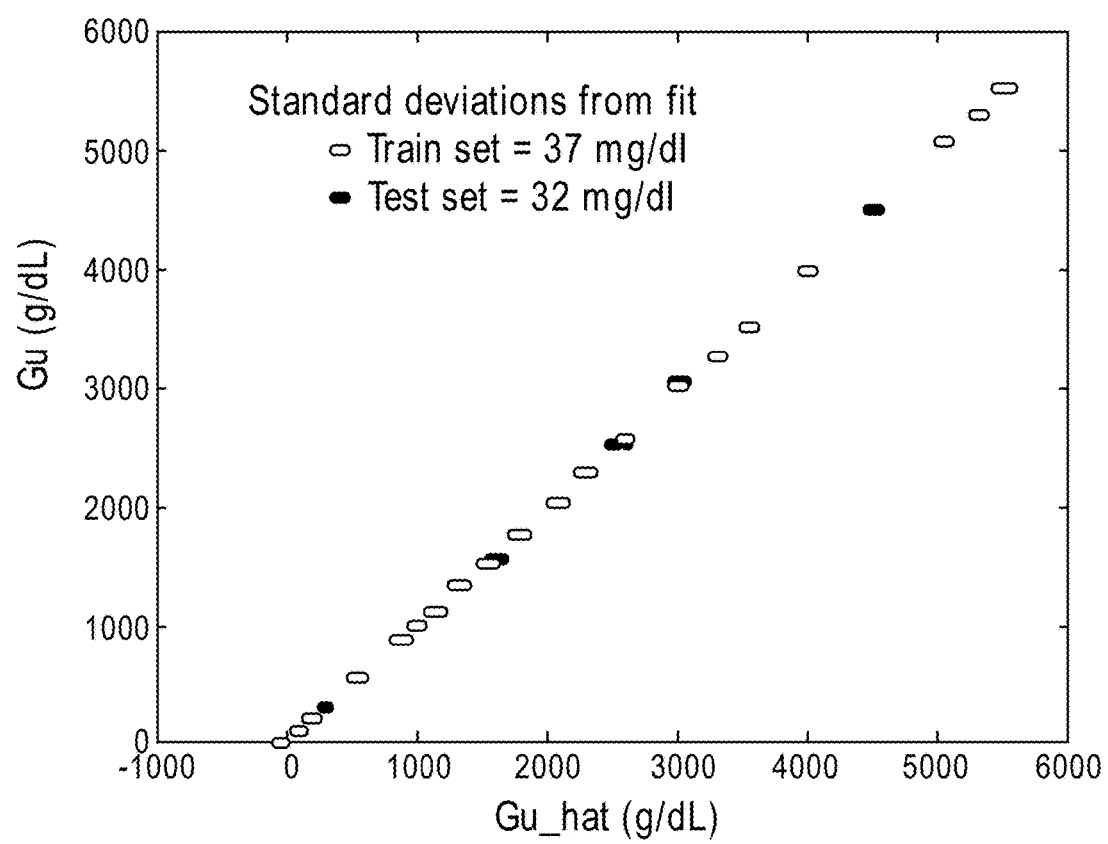

FIG. 19 shows the results obtained by an exemplary sensor 101 of the present disclosure that was configured for measuring glucose. This sensor 101 was tested using a turbid ex-vivo sample. In particular, 25 samples of water/glucose/Lyposin were prepared that ranged from 0-55 mg/dL. Five samples were used as a training set and 20 samples were then used as a test population. As shown, embodiments of sensor 101 were able to obtain at least a standard deviation of 37 mg/dL in the training set and 32 mg/dL in the test population.

Figure 20:
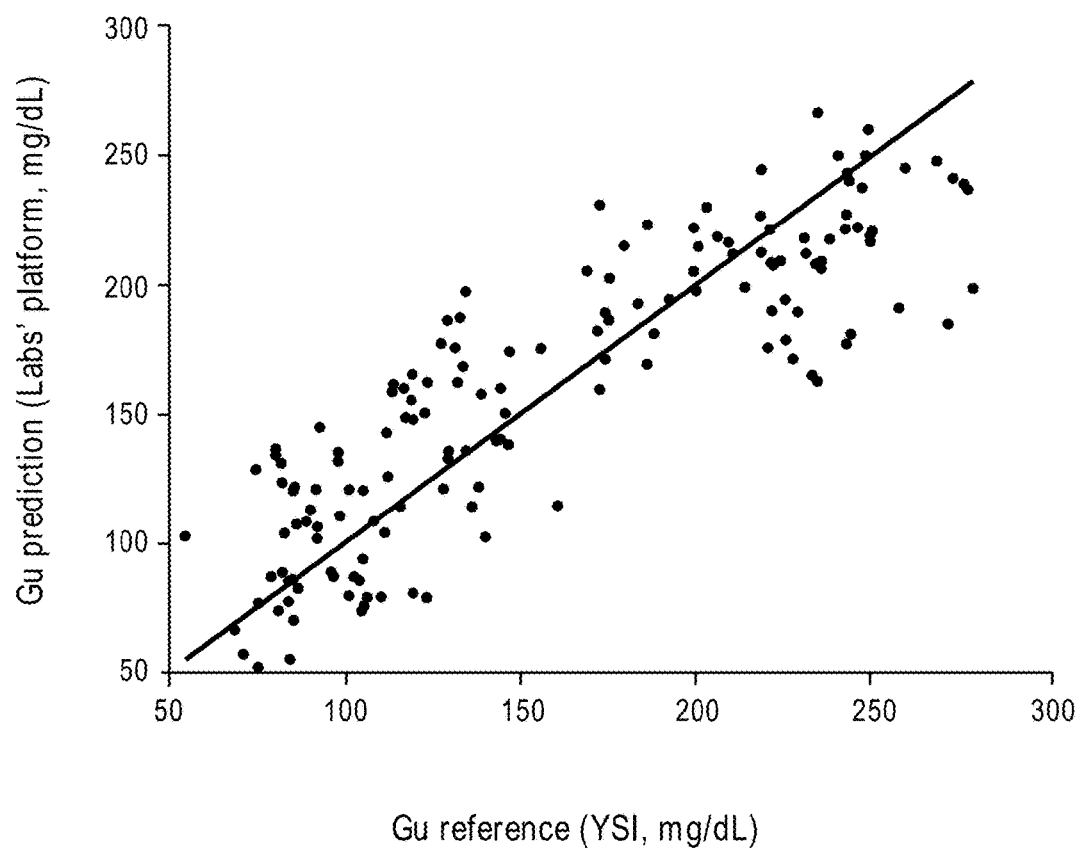
Figure 21:
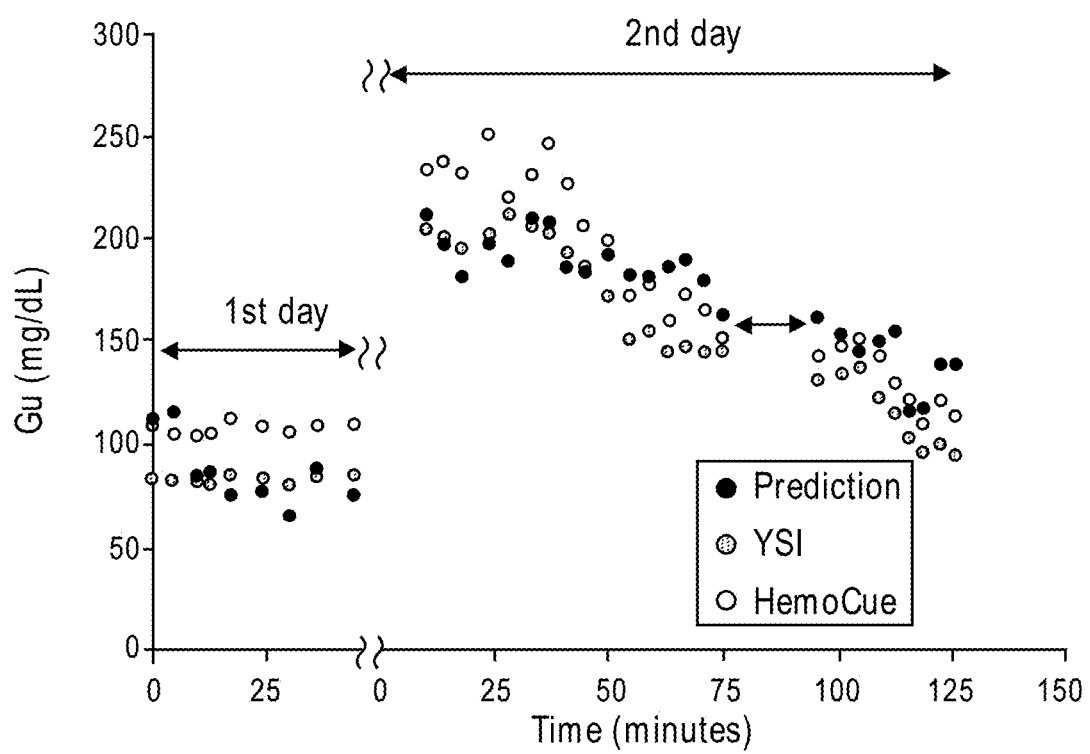
Figure 22:
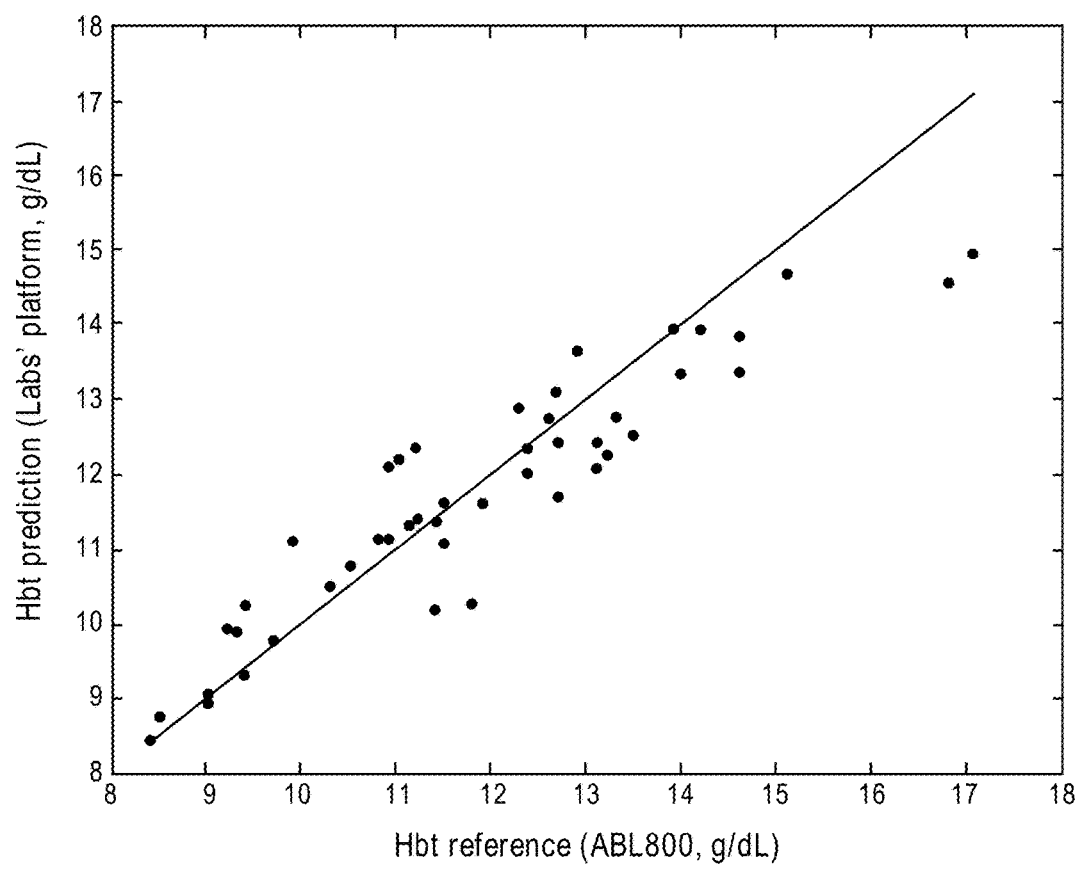

FIGS. 20 through 22 shows other results that can be obtained by an embodiment of system 100. In FIG. 20, 150 blood samples from two diabetic adult volunteers were collected over a 10-day period. Invasive measurements were taken with a YSI glucometer to serve as a reference measurement. Noninvasive measurements were then taken with an embodiment of system 100 that comprised four LEDs and four independent detector streams. As shown, the system 100 obtained a correlation of about 85% and Arms of about 31 mg/dL.

In FIG. 21, 34 blood samples were taken from a diabetic adult volunteer collected over a 2-day period. Invasive measurements were also taken with a glucometer for comparison. Noninvasive measurements were then taken with an embodiment of system 100 that comprised four LEDs in emitter 104 and four independent detector streams from detectors 106. As shown, the system 100 was able to attain a correlation of about 90% and Arms of about 22 mg/dL.

The results shown in FIG. 22 relate to total hemoglobin testing with an exemplary sensor 101 of the present disclosure. In particular, 47 blood samples were collected from nine adult volunteers. Invasive measurements were then taken with a CO-oximeter for comparison. Noninvasive measurements were taken with an embodiment of system 100 that comprised four LEDs in emitter 104 and four independent detector channels from detectors 106. Measurements were averaged over 1 minute. As shown, the testing resulted in a correlation of about 93% and Arms of about 0.8 mg/dL.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While certain embodiments of the inventions disclosed herein have been described, these embodiments have been presented by way of example only, and are not intended to limit the scope of the inventions disclosed herein. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein.

What is claimed is:

1. A noninvasive optical physiological sensing system comprising:
    a platform including a planar surface;
    a housing including a raised edge portion extending from and enclosing at least a portion of the planar surface;
    at least four detectors arranged on the planar surface of the platform and within the housing, wherein the at least four detectors are arranged in a grid pattern such that a first detector and a second detector are arranged across from each other on opposite sides of a central point along a first axis, and a third detector and a fourth detector are arranged across from each other on opposite sides of the central point along a second axis which is perpendicular to the first axis; and
    the housing including a protruding light permeable cover.

2. The noninvasive optical physiological sensing system of claim 1, wherein the protruding light permeable cover is joined to the housing along the raised edge portion of the housing, and wherein the protruding light permeable cover and the housing together hermetically seal the at least four detectors.

3. The noninvasive optical physiological sensing system of claim 2, wherein the housing is a cylindrical housing protrusion.

4. The noninvasive optical physiological sensing system of claim 2, wherein the protruding light permeable cover comprises a convex lens.

5. The noninvasive optical physiological sensing system of claim 3, wherein the protruding light permeable cover is comprised of a rigid material.

6. The noninvasive optical physiological sensing system of claim 5, wherein the protruding light permeable cover is configured to be positioned between the at least four detectors and tissue of a user when the noninvasive optical physiological sensing system is worn by the user.

7. The noninvasive optical physiological sensing system of claim 6, wherein the protruding light permeable cover is configured to conform tissue of the user to at least a portion of an external surface shape of the protruding light permeable cover when the noninvasive optical physiological sensing system is worn by the user.

8. The noninvasive optical physiological sensing system of claim 7, wherein the raised edge portion creates a gap between the planar surface and the protruding light permeable cover.

9. The noninvasive optical physiological sensing system of claim 7, wherein the housing provides noise shielding for the at least four detectors.

10. The noninvasive optical physiological sensing system of claim 9, wherein the protruding light permeable cover comprises a conductive layer configured to shield the at least four detectors from noise.

11. The noninvasive optical physiological sensing system of claim 1, wherein the physiological parameter is pulse rate.

12. The noninvasive optical physiological sensing system of claim 1, wherein the physiological parameter is at least one of: glucose, oxygen, oxygen saturation, methemoglobin, total hemoglobin, carboxyhemoglobin, or carbon monoxide.

13. The noninvasive optical physiological sensing system of claim 1, wherein the noninvasive optical physiological sensing system is a disposable or a reusable sensing system.

14. The noninvasive optical physiological sensing system of claim 1, wherein the first detector is arranged spaced apart from the second detector, and the third detector arranged spaced apart from the fourth detector.

15. The noninvasive optical physiological sensing system of claim 14, wherein the noninvasive optical physiological sensing system provides a variation in optical path length to the at least four detectors.

16. The noninvasive optical physiological sensing system of claim 1 further comprising a touch-screen display.

17. The noninvasive optical physiological sensing system of claim 1 further comprising:
 a processor configured to:
  receive one or more signals from the at least four detectors, the one or more signals indicative of a physiological parameter of a wearer of the noninvasive optical physiological sensing system; and
  output information indicative of measurements of the physiological parameter to a mobile phone.

18. The noninvasive optical physiological sensing system of claim 17, wherein at least the processor is housed in a mobile monitoring device comprising a touch-screen display.

19. A noninvasive optical physiological sensing system comprising:
 a platform forming a base of a housing, the housing including a raised wall protruding from the platform;
 at least four detectors arranged on the platform and within the raised wall, the at least four detectors spaced apart from each other and configured to output one or more signals responsive to light from one or more light emitters attenuated by body tissue, the one or more signals indicative of a physiological parameter of a wearer of the noninvasive optical physiological sensing system; and
 a light permeable cover arranged above at least a portion of the platform, the light permeable cover protruding above the raised wall.

20. The noninvasive optical physiological sensing system of claim 19, wherein the light permeable cover is comprised of a rigid material.

21. The noninvasive optical physiological sensing system of claim 20, wherein the light permeable cover is configured to be positioned between the at least four detectors and tissue of a user when the noninvasive optical physiological sensing system is worn by the user.

22. The noninvasive optical physiological sensing system of claim 21, wherein the light permeable cover is configured to conform tissue of the user to at least a portion of an external surface shape of the light permeable cover when the noninvasive optical physiological sensing system is worn by the user.

23. The noninvasive optical physiological sensing system of claim 22, wherein the physiological parameter is at least one of: glucose, oxygen, oxygen saturation, methemoglobin, total hemoglobin, carboxyhemoglobin, or carbon monoxide.

24. The noninvasive optical physiological sensing system of claim 22, wherein the physiological parameter is pulse rate.

25. The noninvasive optical physiological measurement sensing system of claim 24, wherein a first detector is arranged across a central axis from a second detector and a third detector is arranged across the central axis from a fourth detector, wherein the first, second, third and fourth detectors form a cross pattern about the central axis.

26. The noninvasive optical physiological sensing system of claim 25, wherein the noninvasive optical physiological sensing system provides a variation in optical path length to the at least four detectors.

27. The noninvasive optical physiological sensing system of claim 26, wherein the noninvasive optical physiological sensing system is comprised as part of a mobile monitoring device.

28. The noninvasive optical physiological sensing system of claim 27, wherein the mobile monitoring device includes a touch-screen display.

29. A physiological monitoring system comprising:
 the noninvasive optical physiological sensing system of claim 19; and
 a processor configured to receive the one or more signals and communicate physiological measurement information to a mobile phone.

* * * * *

UNITED STATES PATENT AND TRADEMARK OFFICE
CERTIFICATE OF CORRECTION

PATENT NO. : 10,299,708 B1
APPLICATION NO. : 16/261366
DATED : May 28, 2019
INVENTOR(S) : Jeroen Poeze et al.

It is certified that error appears in the above-identified patent and that said Letters Patent is hereby corrected as shown below:

In the Specification

In Column 20 at Line 62, Change "$l=l_o$" to --$I=I_o$--.

In Column 20 at Line 62, Change "$l_o$" to --$I_o$--.

In Column 21 at Line 3, Change "$l=l_o$" to --$I/I_o$--.

In Column 21 at Line 8, Change "$l=l_o$" to --$I_1=I_o$--.

In Column 21 at Line 13, Change "$l_1$" to --$I_1$--.

In Column 33 at Line 45, Change "$T=I/l_o$," to --$T=I/I_o$,--.

In Column 33 at Line 48 (approx.), Change "$l_o$" to --$I_o$--.

In Column 33 at Line 55 (approx.), Change "$A=-\log(I/l_o)$" to --$A=-\log(I/I_o)$--.

In Column 33 at Line 58, Change "$-\log(l/l_o)$" to -- $-\log(I/I_o)$--.

In Column 33 at Line 64, Change "$(l_o)$," to --$(I_o)$,--.

In Column 34 at Line 47 (approx.), Change "$I/l_o$" to --$I/I_o$--.

In Column 34 at Line 52 (approx.), Change "$l=l_o$" to --$I=I_o$--.

In Column 34 at Line 54 (approx.), Change "$l_1 \ldots l_n$" to --$I_1 \ldots I_n$--.

In Column 34 at Line 59 (approx.), Change "$l_n=l_o$" to --$I_n=I_o$--.

Signed and Sealed this
Twenty-second Day of October, 2019

Andrei Iancu
*Director of the United States Patent and Trademark Office*

CERTIFICATE OF CORRECTION (continued)
U.S. Pat. No. 10,299,708 B1

In Column 34 at Line 63 (approx.), Change "$l_1/\ln = (l_o * e^{-mb_1 c})/(l_o * e^{-mb_n c})$" to --$I_1/I_n = (I_o * e^{-mb_1 c})/(I_o * e^{-mb_n c})$--.

In Column 34 at Line 64 (approx.), Change "$l_o$," to --$I_o$,--.

In Column 34 at Line 66 (approx.), Change "$l_1/l_n$" to --$I_1/I_n$--.

In Column 35 at Line 2, Change "$l_1 \ldots l_n$" to --$I_1 \ldots I_n$--.

In Column 35 at Line 4, Change "$l_o$" to --$I_o$--.

In Column 41 at Line 8, Change "MO" to --MΩ--.

In Column 41 at Line 11, Change "MO" to --MΩ--.

In Column 41 at Line 20, Change "MO" to --MΩ--.

In Column 41 at Line 22, Change "MO" to --MΩ--.

In the Claims

In Column 44 at Lines 58-59 (approx.), In Claim 3, change "housing protrusion." to --housing.--.